US009255223B2

(12) United States Patent
Jansen et al.

(10) Patent No.: US 9,255,223 B2
(45) Date of Patent: Feb. 9, 2016

(54) POLYMERIZABLE COMPOUNDS AND LIQUID CRYSTAL MEDIA

(75) Inventors: Axel Jansen, Darmstadt (DE); Thorsten Kodek, Trebur (DE); Helmut Haensel, Muehltal (DE); Erdal Durmaz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 21 days.

(21) Appl. No.: 13/574,362

(22) PCT Filed: Dec. 23, 2010

(86) PCT No.: PCT/EP2010/007911
§ 371 (c)(1),
(2), (4) Date: Jul. 20, 2012

(87) PCT Pub. No.: WO2011/088882
PCT Pub. Date: Jul. 28, 2011

(65) Prior Publication Data
US 2012/0298916 A1 Nov. 29, 2012

(30) Foreign Application Priority Data
Jan. 21, 2010 (DE) .......................... 10 2010 005 225

(51) Int. Cl.
C07C 69/75 (2006.01)
C09K 19/54 (2006.01)
C09K 19/30 (2006.01)
C09K 19/02 (2006.01)
C09K 19/04 (2006.01)

(52) U.S. Cl.
CPC ............ *C09K 19/3003* (2013.01); *C07C 69/75* (2013.01); *C09K 19/3001* (2013.01); *C09K 19/0275* (2013.01); *C09K 19/54* (2013.01); *C09K 2019/0448* (2013.01); *C09K 2019/548* (2013.01)

(58) Field of Classification Search
CPC .. C09K 19/0275; C09K 19/54; C09K 19/542; C09K 2019/544; C09K 2019/548; C09K 2019/0448; C07C 69/75
USPC ............ 428/1.1; 252/299.61, 299.62, 299.63, 252/299.66, 299.67; 560/95, 127, 128
See application file for complete search history.

(56) References Cited

U.S. PATENT DOCUMENTS 5,164,111 A * 11/1992 Dorsch et al. ............ 252/299.01
7,060,200 B1 6/2006 Farrand et al.
7,125,500 B2 10/2006 Farrand et al.
7,440,160 B2 10/2008 Heckmeier et al.
2011/0287274 A1 * 11/2011 Mijolovic et al. ............ 428/521

FOREIGN PATENT DOCUMENTS

DE        36 21 581       1/1988
DE        19755245 A1 *   6/1999
WO        WO-2004 046805  6/2004
WO        WO-2005 080529  9/2005
WO        WO-2008 061606  5/2008
WO        WO-2008 119427  10/2008

OTHER PUBLICATIONS

CAPLUS 1982:439354.*
CAPLUS 1999: 394050.*
CAPLUS 2009: 553432.*
CAPLUS 2010: 216266.*
Li et al., "Effects of the Structures of Polymerizable Monomers on the Electro-optical Properties of UV Cured Polymer Dispersed Liquid Crystal Films", Journal of Polymer Science, Par B: Polymer Physics vol. 46, pp. 1369-1375.*
The chmeical compound (as ID No. A07,760,925) provided by Auroar fine chemicals catalog, 2015.*
The RN 1507983-56-3 entered Dec. 31, 2013 in STN data base.*
Asahi Glass Co Ltd., "Liquid crystal material for optical device and optical modulation device," Espacnet, Publication Date: Sep. 1, 2005; English Abstract of WO-2005 080529.
Hisakado, Y. et al., "Large Electro-optic kerr effect in polymer-stabilized liquid-crystalline blue phases," Adv. Mater., 2005, vol. 17, No. 1, pp. 96-98.
International Search Report for PCT/EP2010/007911 dated Apr. 11, 2011.
Kikuchi, H. et al., "Polymer-stabilized liquid crystal blue phases," Nature Materials, Sep. 2002, vol. 1, pp. 64-68.
Merck Patent GMBH, "Polymerisierbare fluessigkristallmaterialien," Espacenet, Publication Date: Jan. 7, 1988, English Abstract of DE-3 621 581.
Office Action related to corresponding Taiwanese Patent Application No. 100102140 dated Dec. 11, 2014.
Yukihiro Mitamura et al. "Silver-Catalyzed Diallylation and Dibenzylation of gem-Dibromoalkanes with Grignard Reagents" Synlett (2010), No. 2 , pp. 0309-0312.

* cited by examiner

Primary Examiner — Shean C Wu
(74) Attorney, Agent, or Firm — Millen, White, Zelano & Branigan, P.C.

(57) ABSTRACT

The invention relates to 1,1-disubstituted cyclohexane derivatives containing one or more polymerizable groups, and to liquid-crystalline media comprising at least one compound of the formula I. At least one of the polymerizable groups is located at the geminally substituted position of the cyclohexane ring. The compounds are suitable for the stabilization of liquid-crystalline phases. Examples of polymer-stabilized blue phases are indicated.

20 Claims, No Drawings

POLYMERIZABLE COMPOUNDS AND LIQUID CRYSTAL MEDIA

The present invention relates to polymerisable 1,1-disubstituted cyclohexane derivatives of the formula I, to a process for the preparation thereof, to the use thereof as components in liquid-crystalline media (LC media), and to electro-optical display elements which contain these LC media.

The prior art discloses media for LC display elements which operate in the liquid-crystalline blue phase (blue phase for short) (WO 04/046805 A1, WO 2008/061606 A1). Compared with other display types, significantly shortened response times are thus expected.

The blue phase is generally observed at the transition from the nematic to the optically isotropic state. The medium in the liquid-crystalline blue phase may be blue, as the name suggests, but also colourless. The aim of efforts to date was to extend the temperature range of the blue phase from less than one degree to a range which can be utilised in practice (cf. H. Kikuchi et al., *Nature Materials* (2002), 1(1), 64-68; Kikuchi, H. et al., *Polymeric Materials Science and Engineering*, (2003), 89, 90-91).

WO 2005/080529 A1 describes polymer-stabilised blue phases comprising mono- and multireactive monomers.

In practice, the polymer-stabilised blue phases described to date use, as monomers, a monoreactive non-mesogenic monomer together with a direactive monomer (RM257).

The publication WO 2008/061606 discloses polymerisable cyclohexane derivatives which are substituted in the 1,4-position on the cyclohexane ring. The cyclohexane ring here may be unsubstituted or substituted by methyl or fluorine groups, for example 2, 2,3,3,5,5,6,6-octafluorocyclohexane-1,4-diyl compounds.

Polymerisable liquid-crystal materials of the formula

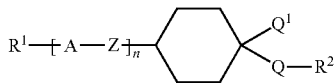

are disclosed in DE 36 21 581, where $Q^1$ can denote alkyl or alkoxy having 1-5 C atoms, F, Cl, Br or CN, for example a CN group, $R^2$ denotes a reactive group, Q denotes a $C_{3-18}$ alkylene, in which $CH_2$ groups may be replaced by —O—, —(CO)—, —(CO)O—, —O(CO)—, —CH=N— or —CH=CH—, and the other radicals describe chains ($R^1$), rings (A) and bridges (Z) in between.

Polymerisable compounds are also used for the stabilisation of the pre-alignment of nematic phases in VA (VA: 'vertical alignment') displays. These so-called PSA-VA (PSA: 'polymer sustained alignment') displays are described, for example, in JP 10-036847 A, EP 1 170 626 A2, U.S. Pat. No. 6,861,107, U.S. Pat. No. 7,169,449, US 2004/0191428 A1, US 2006/0066793 A1 and US 2006/0103804 A1. PSA-OCB displays are described, for example, in T.-J- Chen et al., Jpn. J. Appl. Phys. 45, 2006, 2702-2704 and S. H. Kim, L.-C- Chien, Jpn. J. Appl. Phys. 43, 2004, 7643-7647. PSA-IPS displays are described, for example, in U.S. Pat. No. 6,177, 972 and Appl. Phys. Lett. 1999, 75(21), 3264. PSA-TN displays are described, for example, in Optics Express 2004, 12(7), 1221.

The present invention was based on the object of finding suitable monomers and corresponding polymers for the stabilisation of liquid-crystalline phases, in particular blue phases. The polymer is intended to have the following effects on the properties of the stabilised LC phase:

broad temperature range of the blue phase,
fast response time of the device,
small clearing-point difference on polymerisation,
low operating voltage,
small variation of the operating voltage with temperature,
low hysteresis of the transmission of a cell on changing the operating voltage in order to achieve defined grey shades,
low "memory effect", i.e. a transmission which is little changed after an on/off switching cycle.

In addition, monomer materials which have a good voltage holding ratio (VHR), have high clearing points and are stable to exposure to light and temperature are required. Furthermore, good solubility in LC materials or good miscibility with the LC material is necessary in order to achieve good distribution in the LC host.

The aim of the present invention is, in particular, to provide improved reactive polymerisable compounds which are able to stabilise blue phases and are thus suitable for the preparation of LC materials having improved properties.

This object is achieved in accordance with the invention by compounds of the general formula I.

The invention thus relates firstly to compounds of the formula I

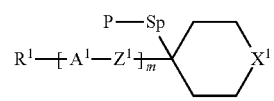

in which
$X^1$ denotes

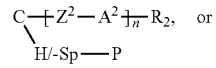

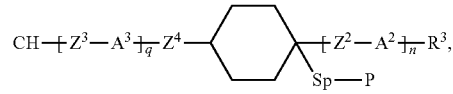

$R^1$ and $R^2$ each, independently of one another, denote a radical -Sp-P, a halogenated or unsubstituted alkyl radical having 1 to 15 C atoms, where, in addition, one or more $CH_2$ groups in these radicals may each be replaced, independently of one another, by —C≡C—, —CH=CH—, —(CO)O—, —O(CO)—, —(CO)— or —O— in such a way that O atoms are not linked directly to one another, F, Cl, Br, CN, SCN, NCS or $SF_5$,
where $R^1$ denotes a group -Sp-P if m=0 and $X^1$ does not contain a group -Sp-P,
$R^3$ independently is defined like $R^2$ or denotes H,
$A^1$, $A^2$ and $A^3$ each, independently of one another, denote:
  a) trans-1,4-cyclohexylene or cyclohexenylene, in which, in addition, one or more non-adjacent $CH_2$ groups may be replaced by —O— and/or —S— and in which H may be substituted by F,
  b) 1,4-phenylene, in which one or two CH groups may be replaced by N and in which, in addition, one or more H atoms may be replaced by Br, Cl, F, CN, methyl, methoxy or a mono- or polyfluorinated methyl or methoxy group,
or
  c) a radical from the group bicyclo[1.1.1]pentane-1,3-diyl, bicyclo [2.2.2]octane-1,4-diyl, spiro[3.3]heptane-2,6- diyl, tetrahydropyran-2,5-diyl, 1,3-dioxane-2,5-diyl, tetrahydrofuran-2,5-diyl, cyclobut-1,3-diyl, piperidine-1,4-diyl, thiophene-2,5-diyl, selenophene-2,5-diyl,

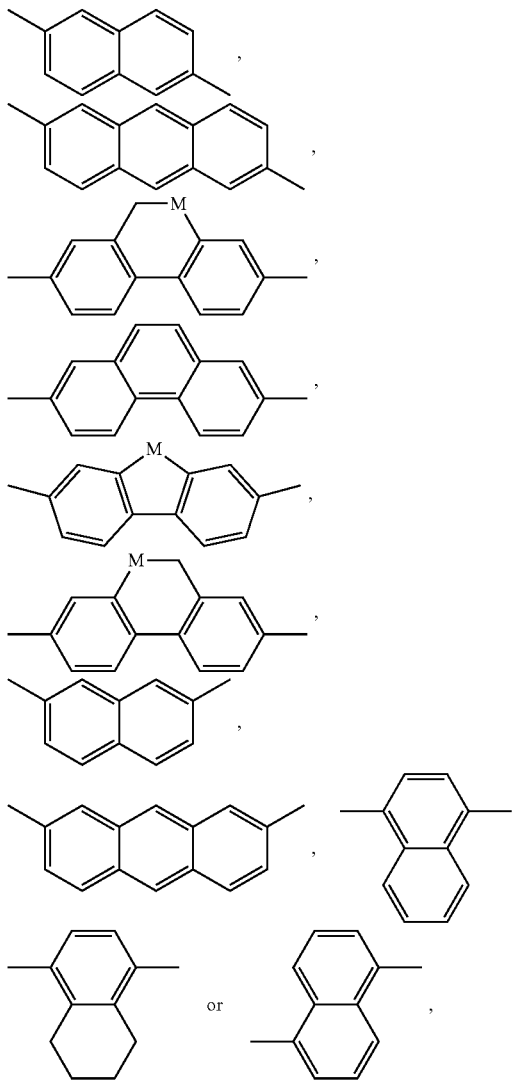

in which one or more hydrogen atoms may be substituted by F, CN, SCN, NCS, SF$_5$, CH$_2$F, OHF$_2$, CF$_3$, OCH$_2$F, OCHF$_2$ or OCF$_3$, one or more double bonds may be replaced by single bonds, one or more CH groups may be replaced by N, M denotes —O—, —S—, —CH$_2$—, —CHY— or —CYY$^1$—, and Y and Y$^1$ denote Cl, F, CN, OCF$_3$ or OF$_3$, Z$^1$, Z$^2$, Z$^3$ or Z$^4$ each, independently of one another, denote a single bond, —O—, —CH$_2$—, —O(CO)CH$_2$, —CH$_2$O—, —CH$_2$OCH$_2$—, —(CO)O—, —OF$_2$O—, —CH$_2$CH$_2$CF$_2$O—, —CF$_2$CF$_2$—, —CH$_2$CF$_2$—, —CH$_2$CH$_2$—, —(CH$_2$)$_4$—, —CH=CH—, —CH=CF—, —CF=CF— or —C≡C—, where asymmetrical bridges may be oriented to both sides, m denotes 0, 1, 2 or 3, preferably 0, 1 or 2, particularly preferably 0 or 1, n denotes 0, 1, 2 or 3, preferably 0, 1 or 2, particularly preferably 0 or 1, q denotes 0, 1, 2 or 3, preferably 0, P denotes a polymerisable group, and Sp denotes a spacer group or a single bond.

The number of polymerisable groups P is therefore one, two, three or four, preferably two, three or four.

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups P are selected from CH$_2$=CW$^1$—COO—, CH$_2$=CW$^1$—CO—,

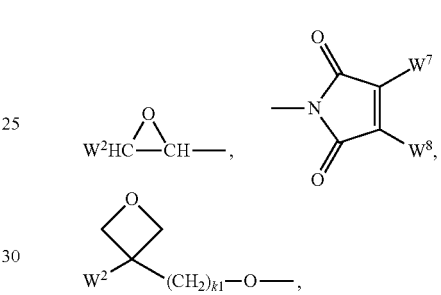

CH$_2$=CW$^2$—(O)$_{k3}$—, CW$^1$=CH—CO—(O)$_{k3}$—, CW$^1$=CH—CO—NH—, CH$_2$=CW$^1$—CO—NH—, CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe(O)$_{k2}$—, CH$_2$=CH—(CO)$_{k1}$-Phe-(O)$_{k2}$—, Phe-CH=CH—, HOOC—, OCN— and W$^4$W$^5$W$^6$Si—, in which W$^1$ denotes H, F, Cl, CN, CF$_3$, phenyl or alkyl having 1 to 5 C atoms, in particular H, F, C$_1$ or CH$_3$, W$^2$ and W$^3$ each, independently of one another, denote H or alkyl having 1 to 5 C atoms, in particular H, methyl, ethyl or n-propyl, W$^4$, W$^5$ and W$^6$ each, independently of one another, denote Cl, oxaalkyl or oxacarbonylalkyl having 1 to 5 C atoms, W$^7$ and W$^8$ each, independently of one another, denote H, Cl or alkyl having 1 to 5 C atoms, Phe denotes 1,4-phenylene, which is optionally substituted by one or more radicals L as defined above, k$_1$, k$_2$ and k$_3$ each, independently of one another, denote 0 or 1, and k$_3$ preferably denotes 1.

Particularly preferred groups P are CH$_2$=CW$^1$—COO—, in particular CH$_2$=CH—COO—, CH$_2$=C(CH$_3$)—COO— and CH$_2$=CF—COO—, furthermore CH$_2$=CH—O—, (CH$_2$=CH)$_2$CH—OCO—, (CH$_2$=CH)$_2$CH—O—,

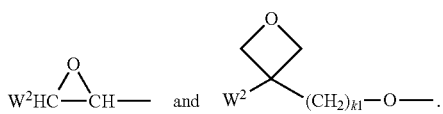

Very particularly preferred groups P are vinyloxy, acrylate, methacrylate, fluoroacrylate, chloroacrylate, oxetane and epoxide, in particular acrylate and methacrylate.

The monomers according to the invention are suitable, depending on the number of polymerisable groups per molecule, for the formation of polymers which are crosslinked to various extents. If they contain only one polymerisable group, they form polymer chains. They preferably contain, at least in some cases, two or more polymerisable groups and serve as crosslinking agents.

The term "spacer group" (or "spacer"), also referred to as "Sp" above and below, is known to the person skilled in the art and is described in the literature, see, for example, M. Barón, *Pure Appl. Chem.* 2001, 73(5), 888, and C. Tschierske, G. Pelzl, S. Diele, *Angew. Chem.* 2004, 116, 6340-6368. Unless indicated otherwise, the term "spacer group" or "spacer" above and below denotes a flexible group which connects a ring group and the polymerisable group(s) in a polymerisable compound to one another.

Preferred spacer groups Sp are selected from the formula Sp'-X, so that the radical P-Sp- conforms to the formula P-Sp'-X—, where Sp' denotes alkylene having 1 to 24, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —$NR^0$—, —$SiR^{00}R^{000}$—, —CO—, —(CO)O—, —O(CO)—, —O(CO)O—, —S(CO)—, —(CO)S—, —$NR^{00}$—CO—O—, —O—CO—$NR^{00}$—, —$NR^{00}$—CO—$NR^{00}$—, —CH═CH— or —C≡C— in such a way that O and/or S atoms are not linked directly to one another, X denotes —O—, —S—, —CO—, —(CO)O—, —O(CO)—, —O(CO)O—, —CO—$NR^{00}$—, —$NR^{00}$—CO—, —$NR^{00}$—CO—$NR^{00}$—, —$OCH_2$—, —$CH_2O$—, —$(CH_2)_2$—O—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH═N—, —N═CH—, —N═N—, —CH═$CR^0$—, —$CY^2$═$CY^3$—, —C≡C—, —CH═CH—(CO)O—, —O(CO)—CH═CH— or a single bond, preferably a single bond, —O—, —O(CO)—, —$(CH_2)_2$—O—, —$CH_2$(CO)O— or —$OCH_2$—, $R^{00}$ and $R^{000}$ each, independently of one another, denote H or alkyl having 1 to 12 C atoms, and $Y^2$ and $Y^3$ each, independently of one another, denote H, F, Cl or CN.

Typical spacer groups Sp' are, for example, —$(CH_2)_{p1}$—, —$(CH_2CH_2O)_{p2}$—, —$CH_2CH_2$—, —$CH_2CH_2$—S—$CH_2CH_2$—, —$CH_2CH_2$—NH—$CH_2CH_2$— or —$(SiR^{00}R^{000}$—O$)_{p1}$—, in which p1 is an integer from 1 to 24, p2 is an integer from 1 to 6, and $R^{00}$ and $R^{000}$ have the meanings indicated above.

Particularly preferred groups —X-Sp'- are —$(CH_2)_{p1}$—, —O—$(CH_2)_{p1}$—, —O(CO)—$(CH_2)_{p1}$—, —$CH_2$—(CO)O—$(CH_2)_{p1}$—, —$(CH_2)_2$—O—$(CH_2)_{p1}$— or —O(CO)O—$(CH_2)_{p1}$—, Particularly preferred groups Sp' are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

The radical $X^1$ preferably denotes one of the following radicals:

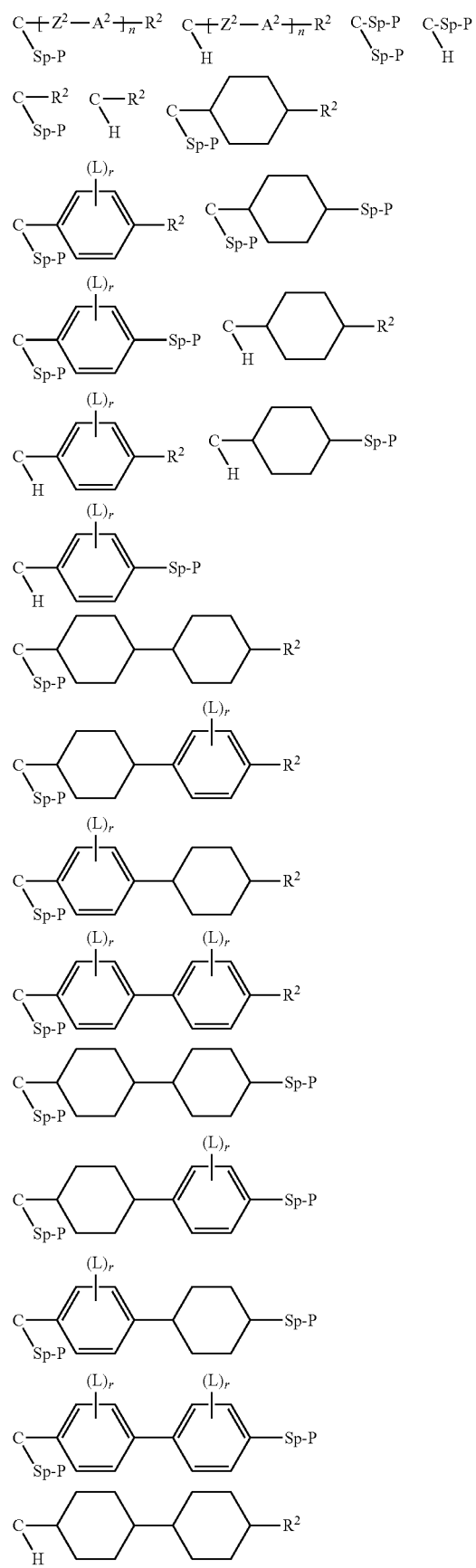

-continued

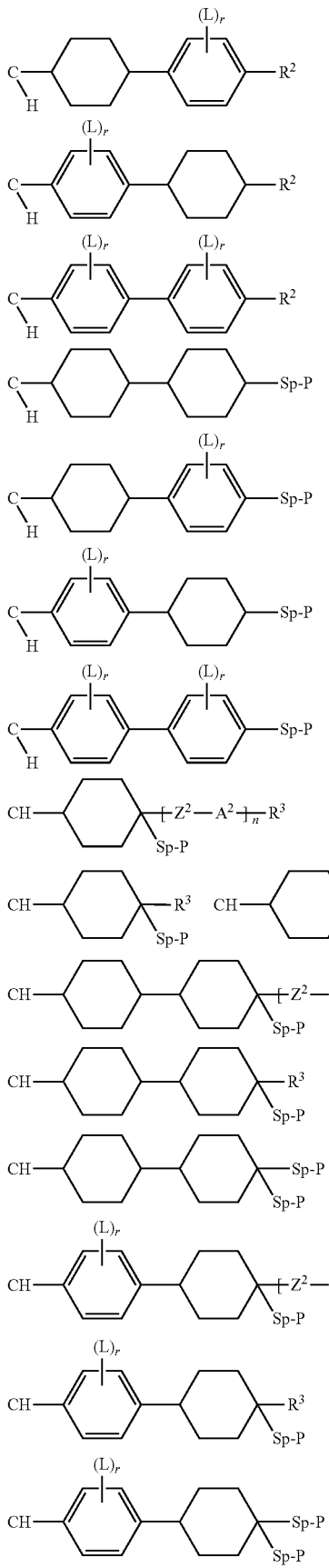

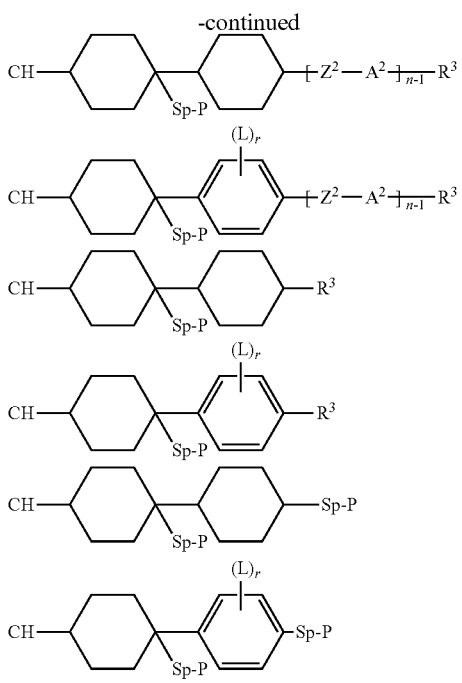

$A^1$ and $A^2$ may adopt different meanings in the formulae if they occur more than once for m>1. The same applies analogously to the groups $Z^1$, $Z^2$ and -Sp-P. The groups -Sp-P are preferably identical to one another.

The groups $R^1$, $R^2$ and $R^3$ preferably denote, independently of one another, a group P-Sp-, alkyl, alkoxy having 1-12 C atoms or an alkenyl radical having 2-12 C atoms.

The compounds of the formula I preferably have the following stereochemistry:

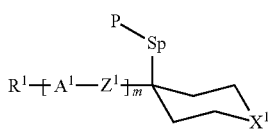

i.e. the group -Sp-P is in the axial arrangement and the radical $R^1$—[$A^1$-$Z^1$]$_m$— is in the equatorial arrangement.

Analogously thereto, the substituent in the radical $X^1$ which is drawn to the right (ending in —$R_2$ or —$R_3$) is preferably in the equatorial arrangement and the substituent drawn to the bottom is preferably in the axial arrangement.

The compounds of the formula I according to the invention are preferably those of the formula IA

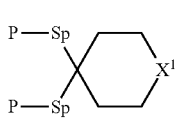

IA in which P, Sp and $X^1$ are as defined for formula I.

The compounds according to the invention are highly suitable as polymerisable components in liquid-crystalline media. The polymer enables the stabilisation of liquid-crystalline phases, in particular blue phases. Compared with conventional monomers, a significant reduction in the operating voltages is observed. At the same time, the tendency towards the formation of hystereses in the transmission (grey values) can be controlled depending on the (rising or falling) operating voltage.

The radicals [P-Sp-] can be in any of the proposed positions. At least two of these radicals are preferably adjacent in the 1,1-position on one of the cyclohexane rings. In the formula I, at least one group from $R^1$ and $R^3$ therefore preferably denotes a radical P-Sp-, or $X^1$ denotes a radical containing two radicals P-Sp- in $R^2$ and the adjacent group.

In a preferred embodiment of the invention, the sum of the variables $m+n+q=0$, 1 or 2, or $m+n=0$, 1 or 2 if q is not present.

In the following formulae and schemes, the radical R on the acrylate group generally denotes a radical which is defined like $W^1$ in the polymerisable radical P, i.e. H, F, Cl, CN, $CF_3$, phenyl or alkyl having 1 to 5 C atoms, in particular the radicals H, F, $C_1$ or $CH_3$. R preferably denotes H or methyl.

Particularly preferred compounds of the formula I are therefore the following illustrative compounds:

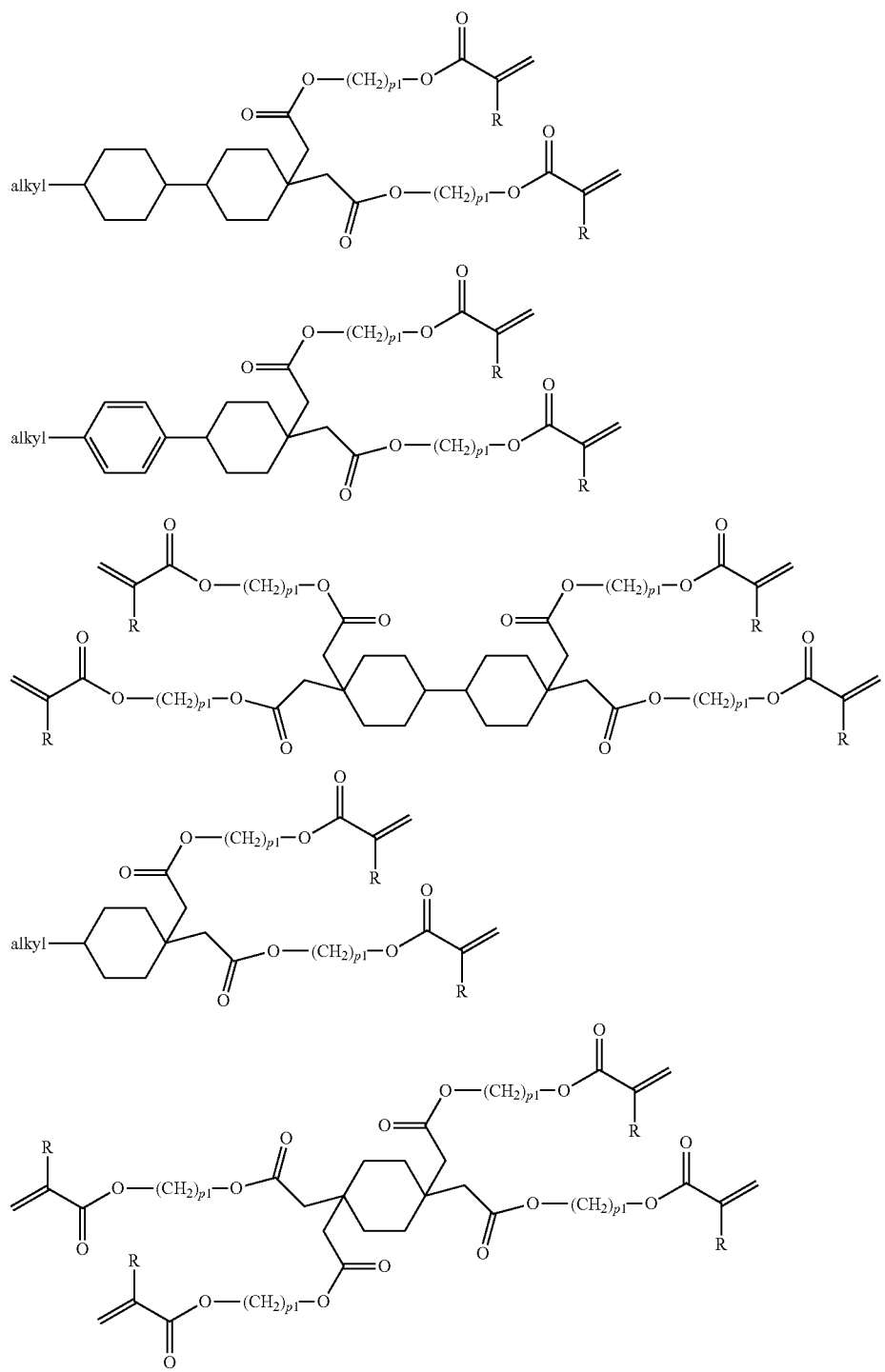

11 12
-continued
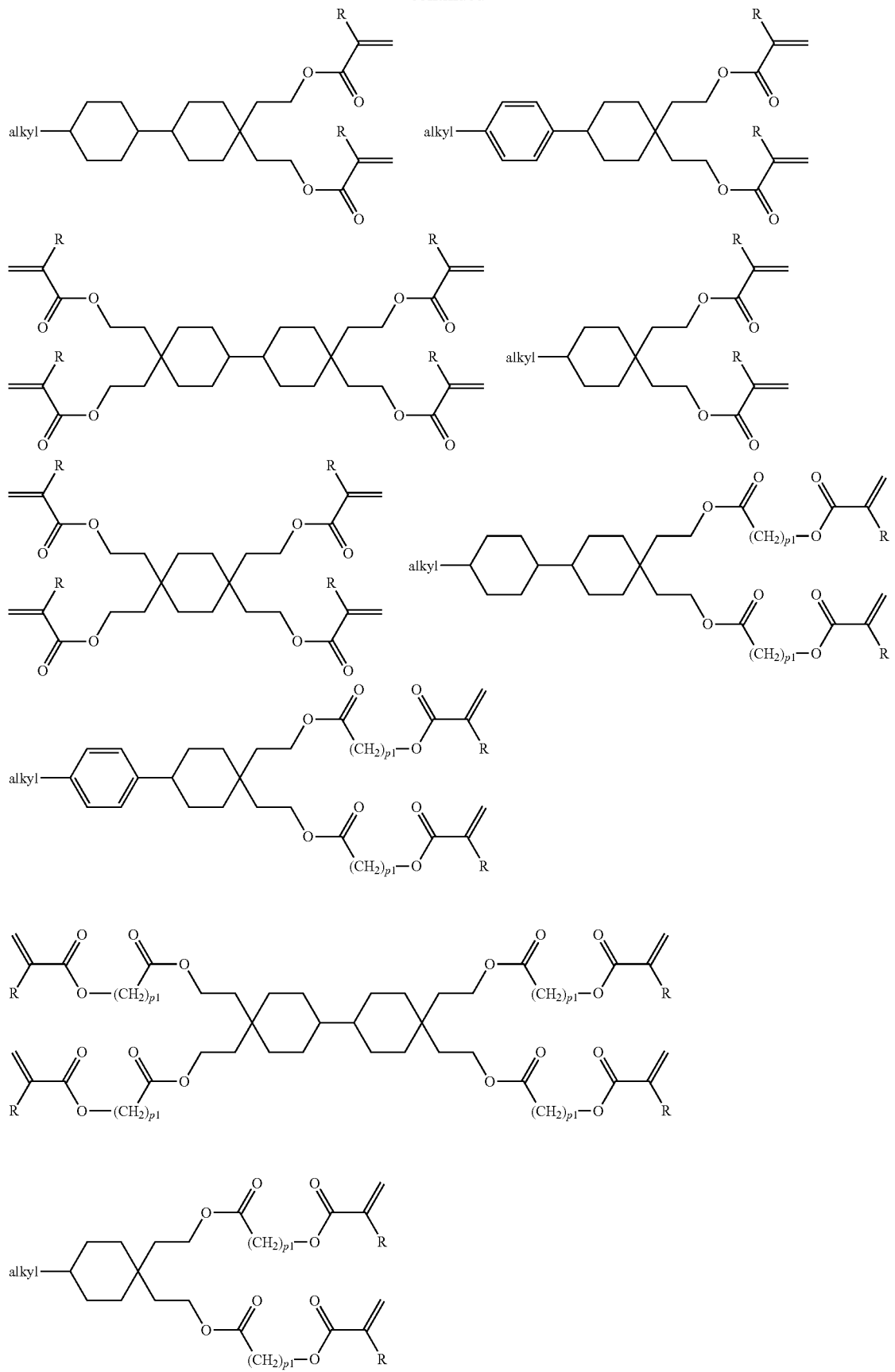

-continued
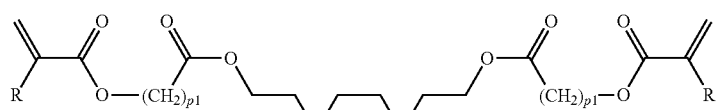
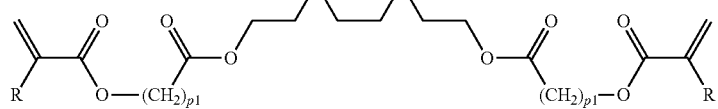
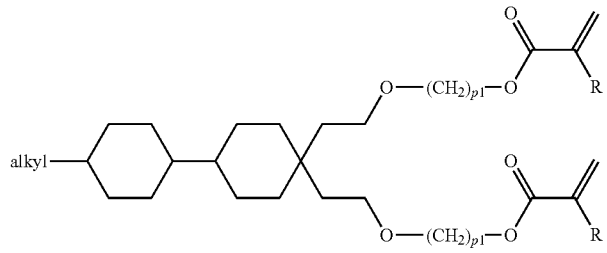
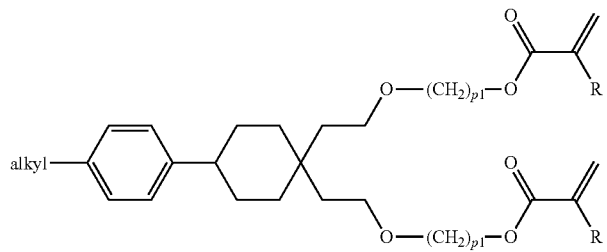
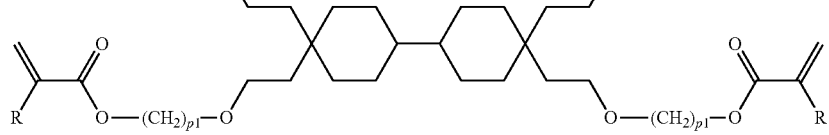
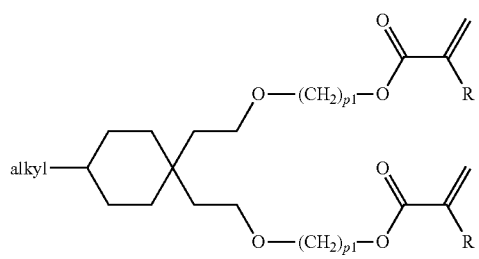

-continued
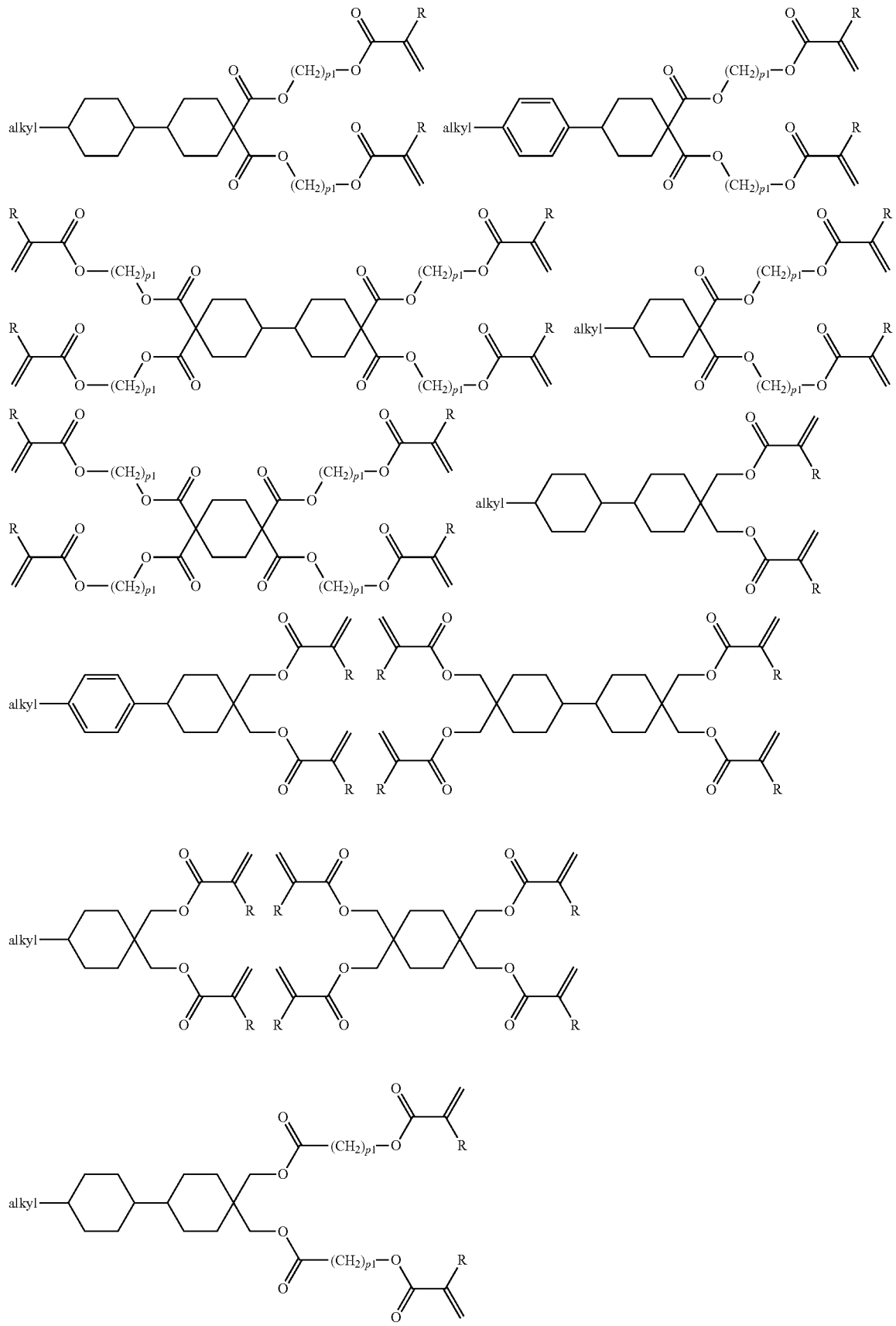

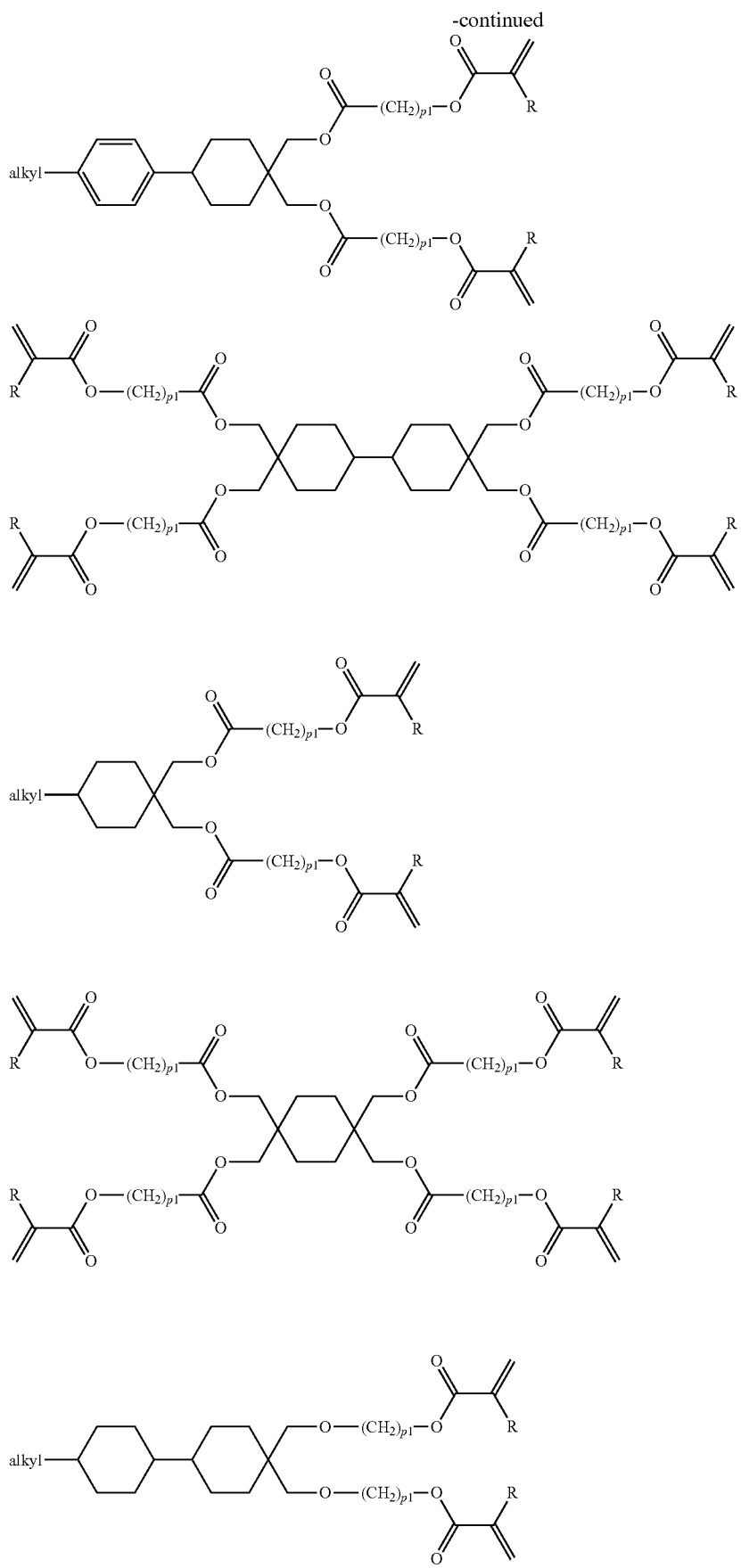

-continued
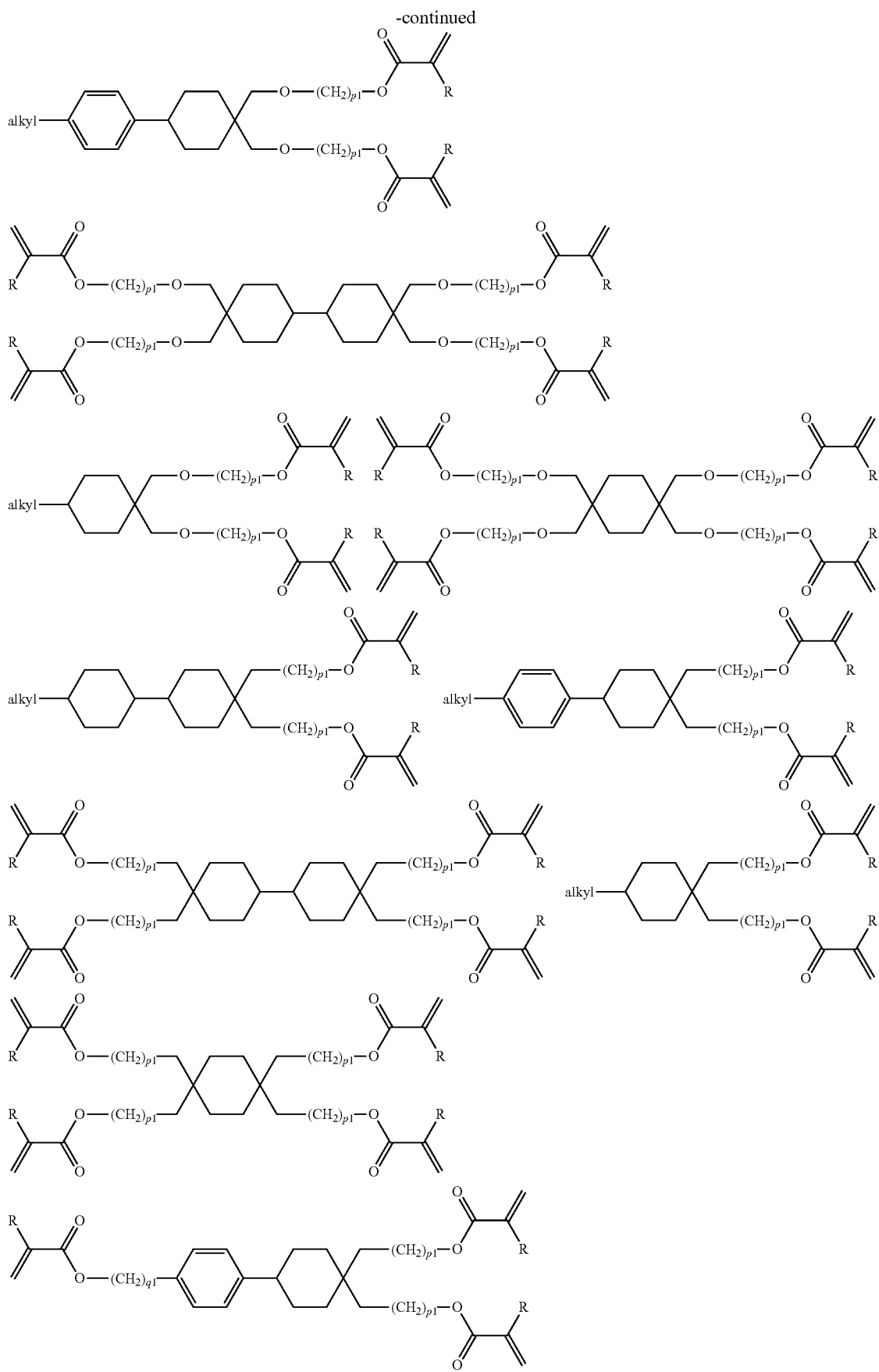

-continued
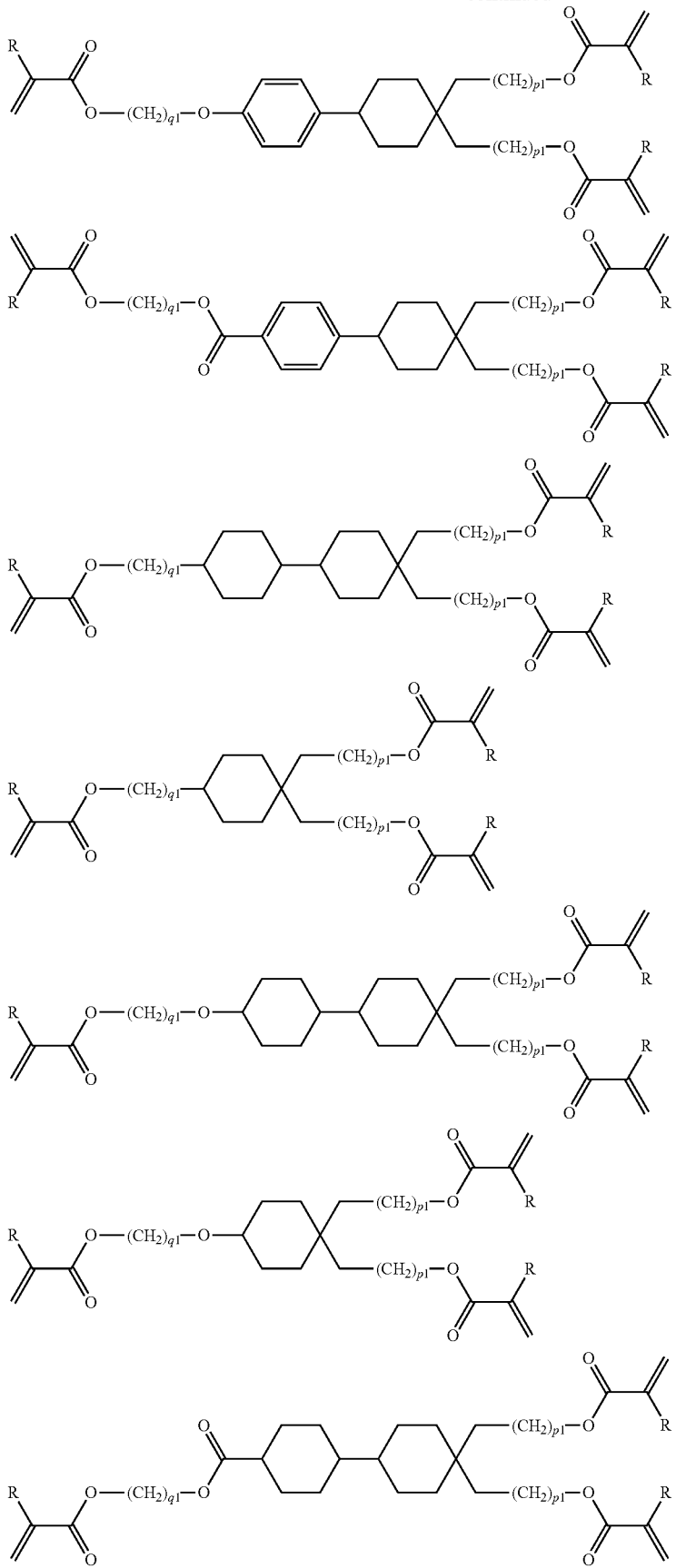

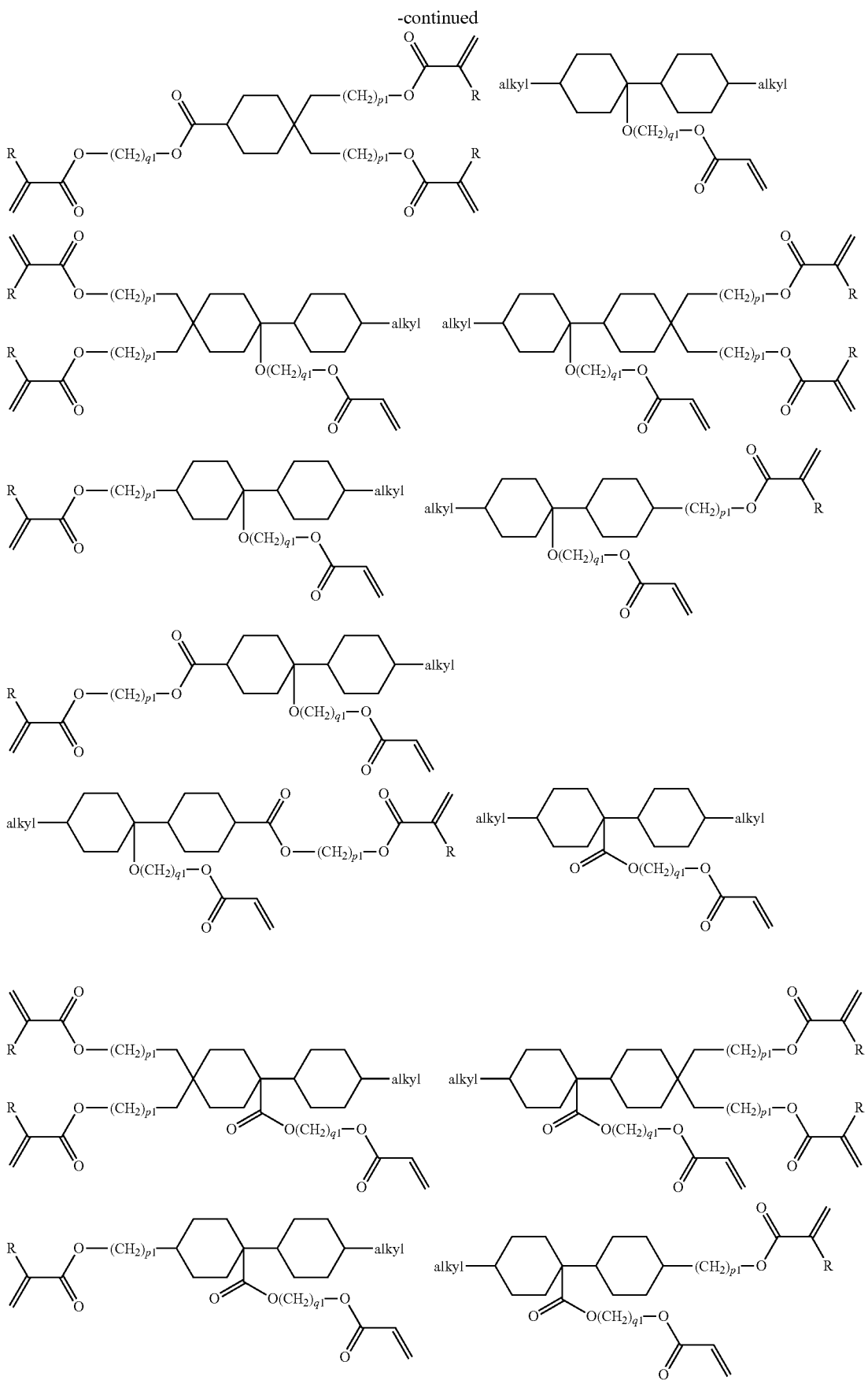

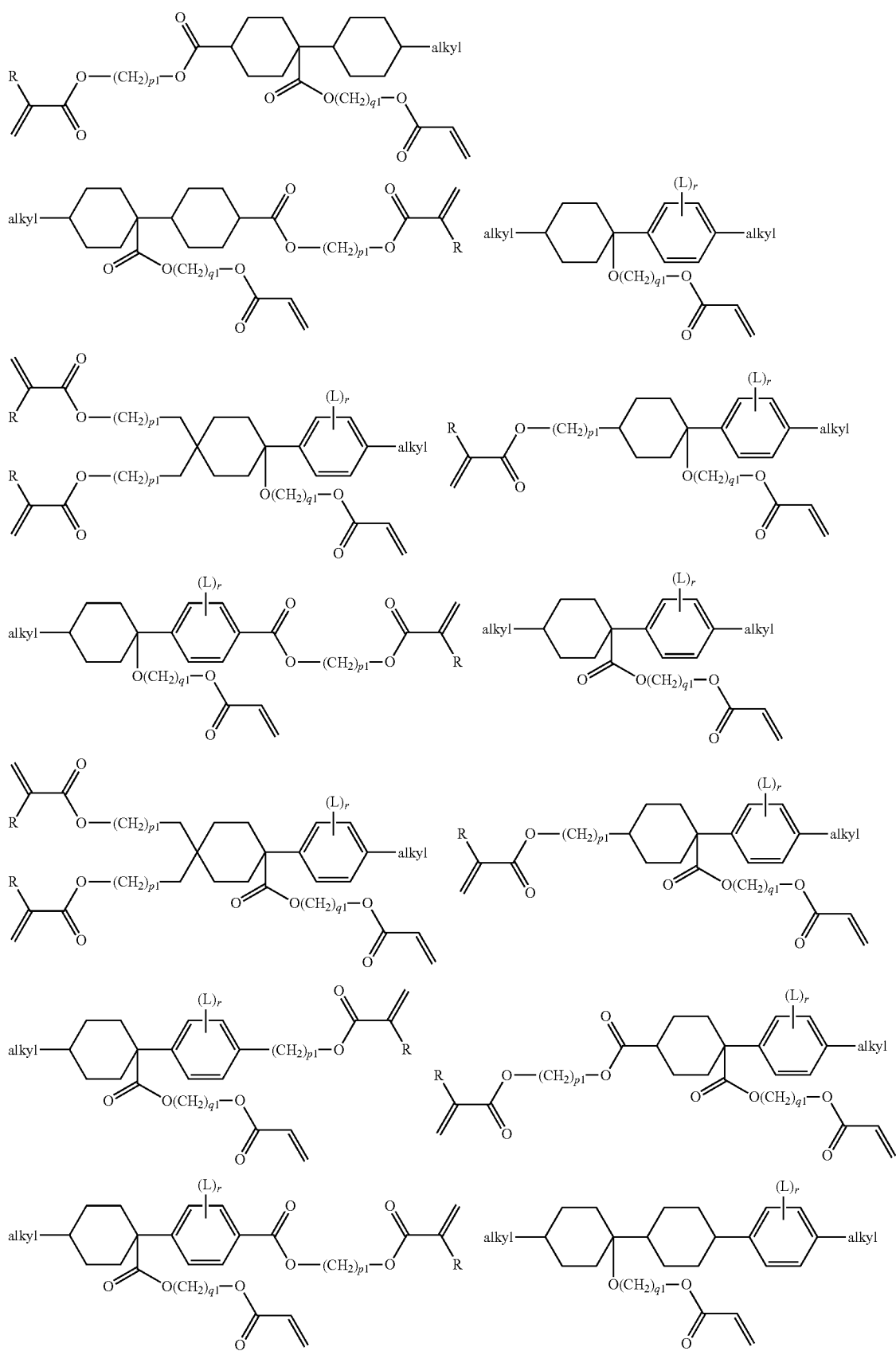

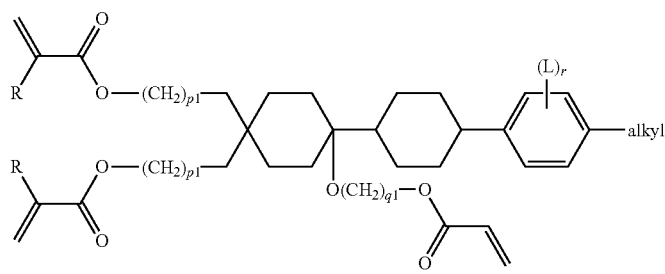
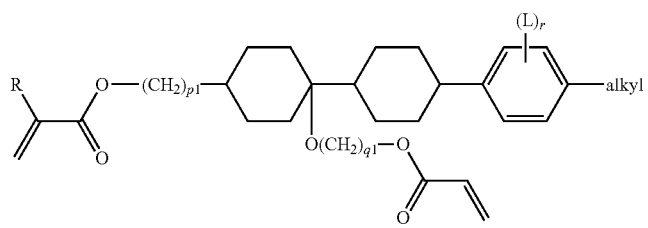
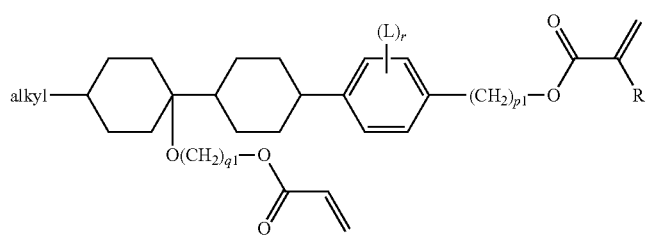
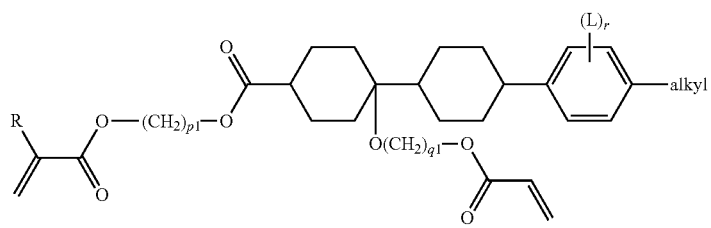
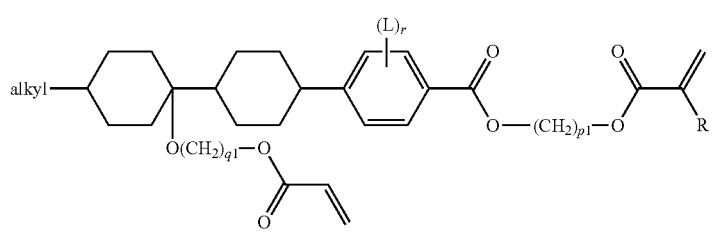
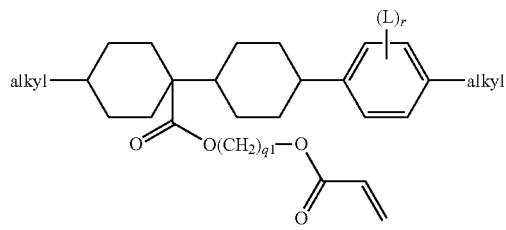
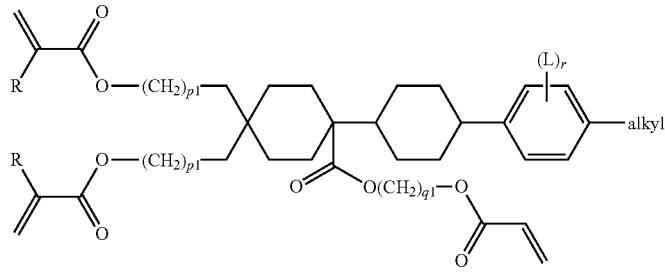

-continued
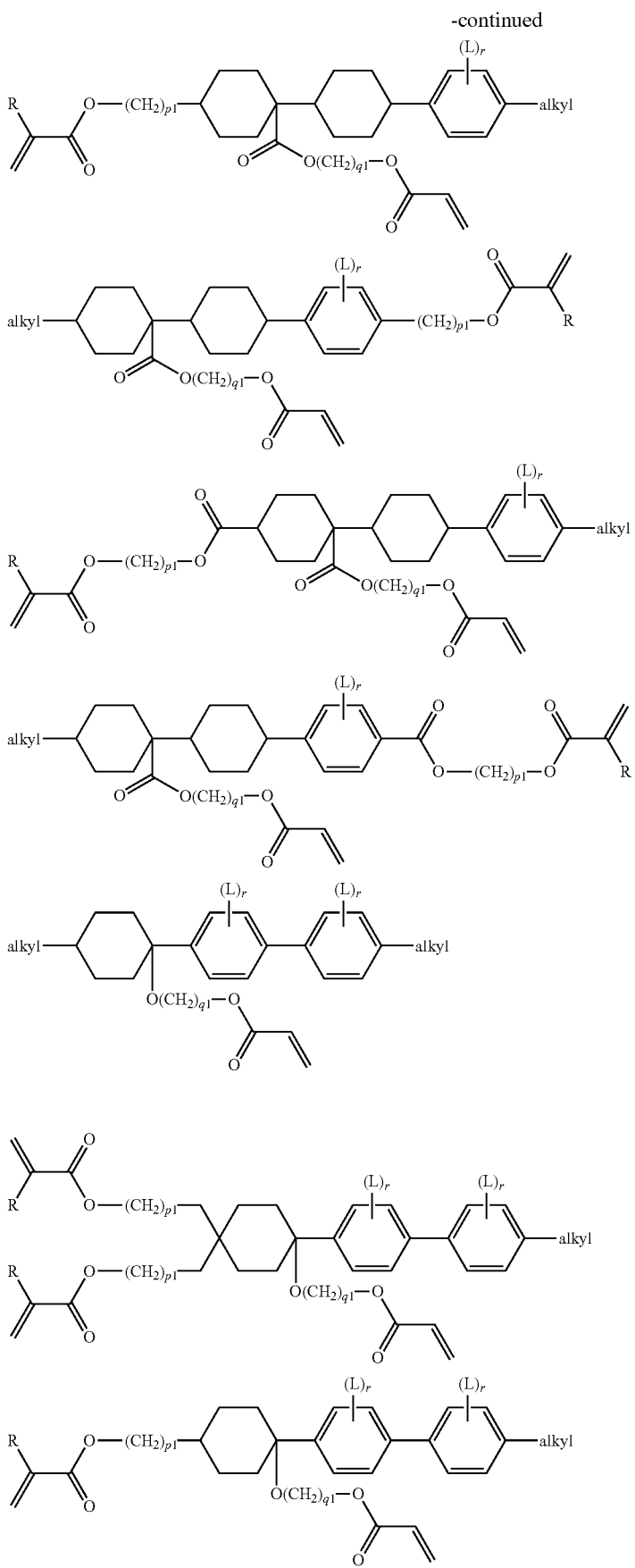

-continued
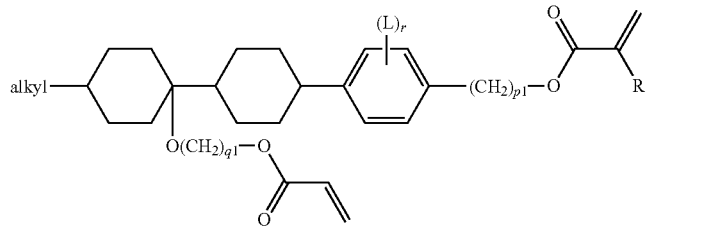
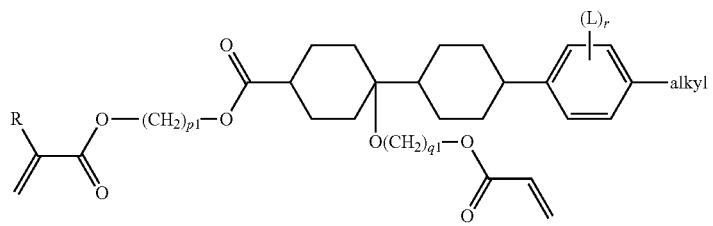
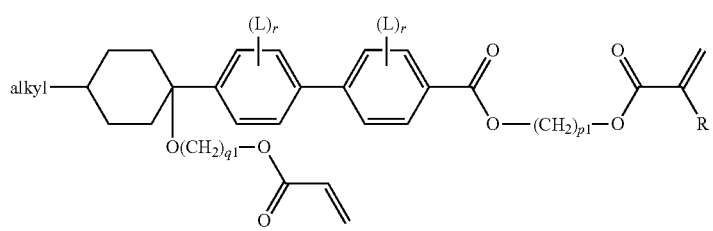
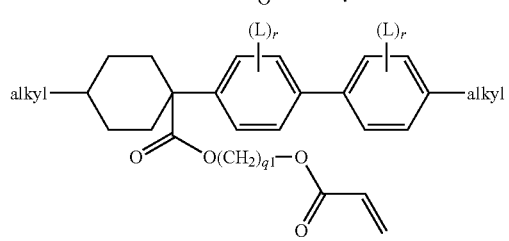
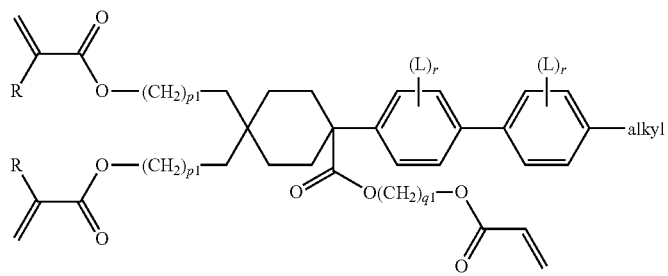
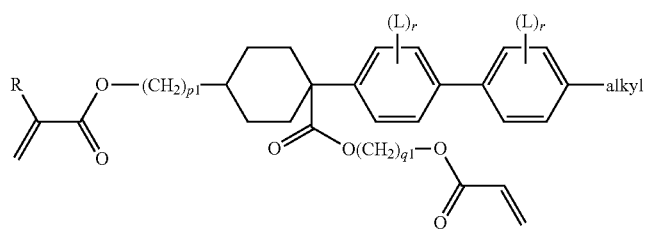
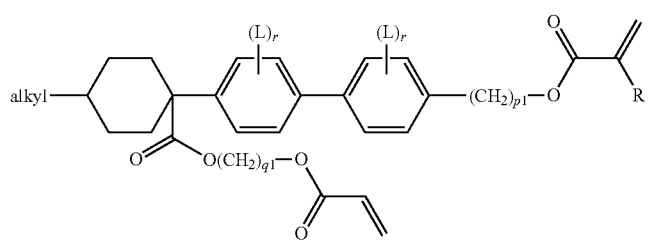

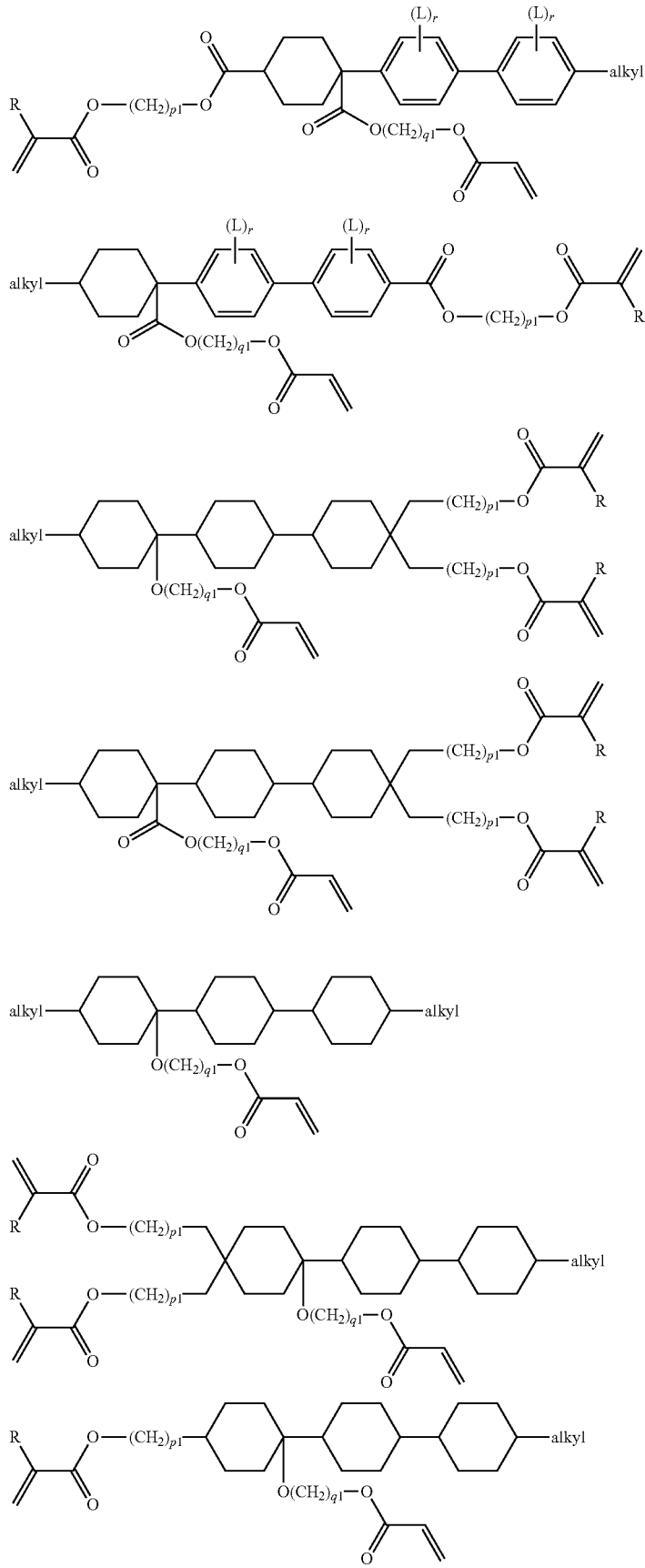

-continued
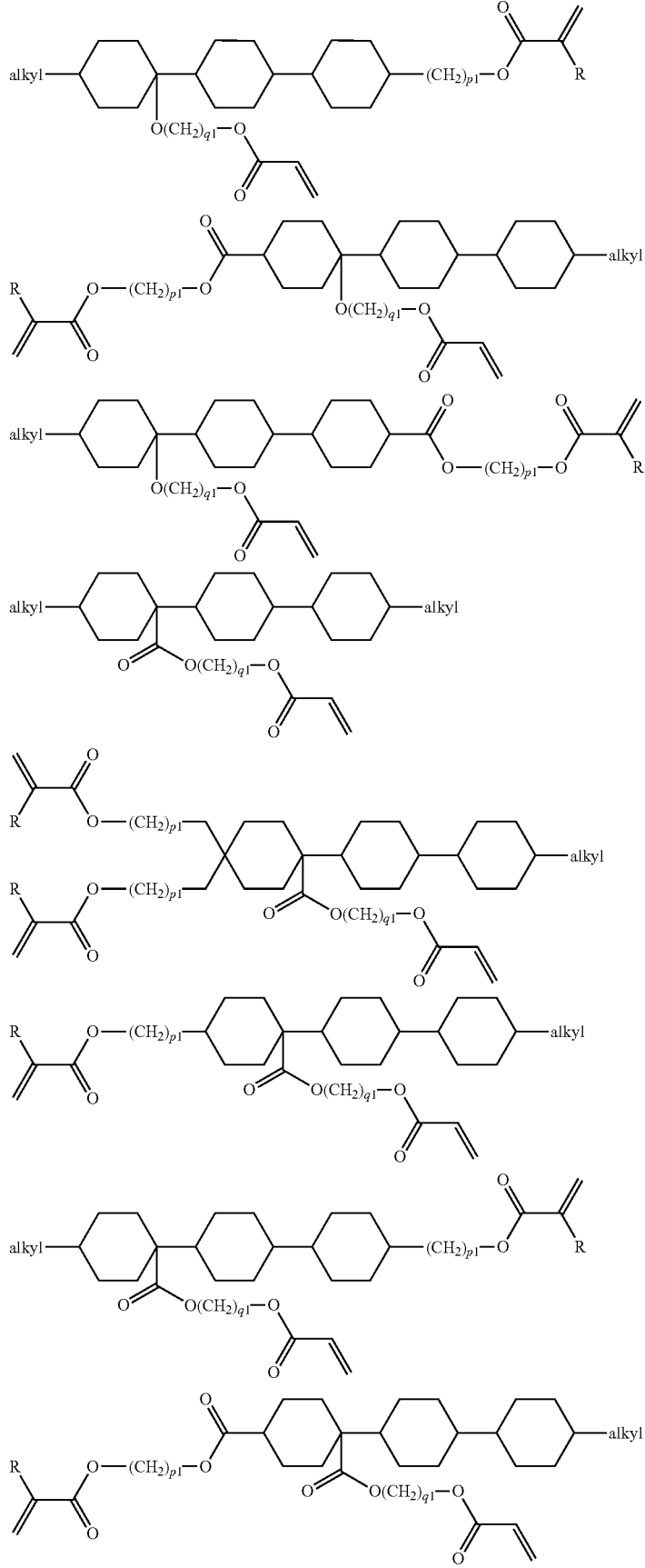

-continued
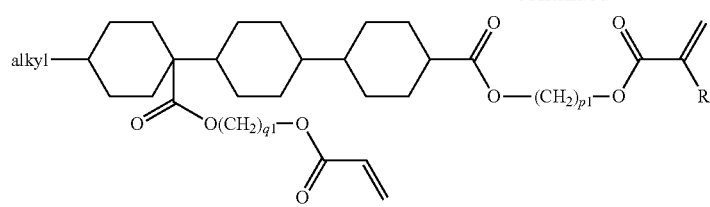
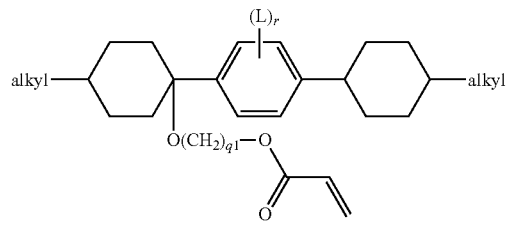
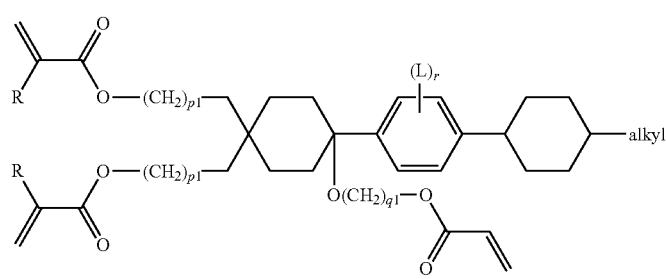
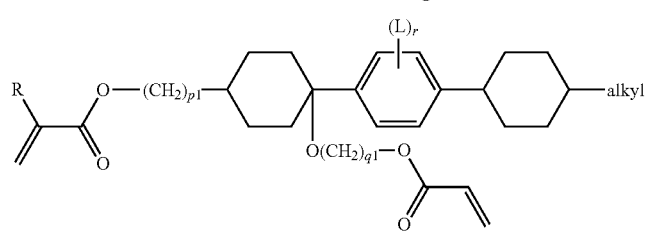
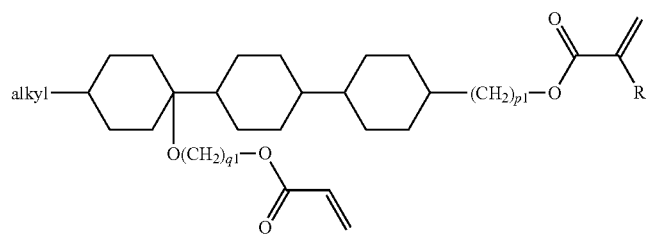
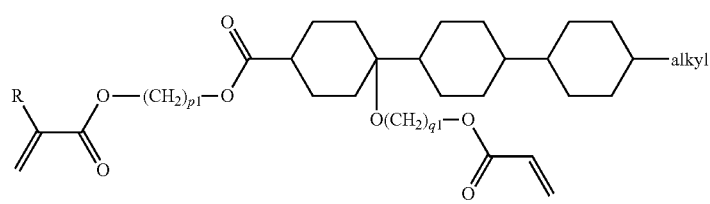
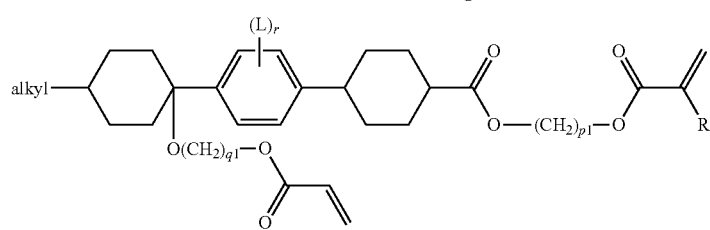

-continued
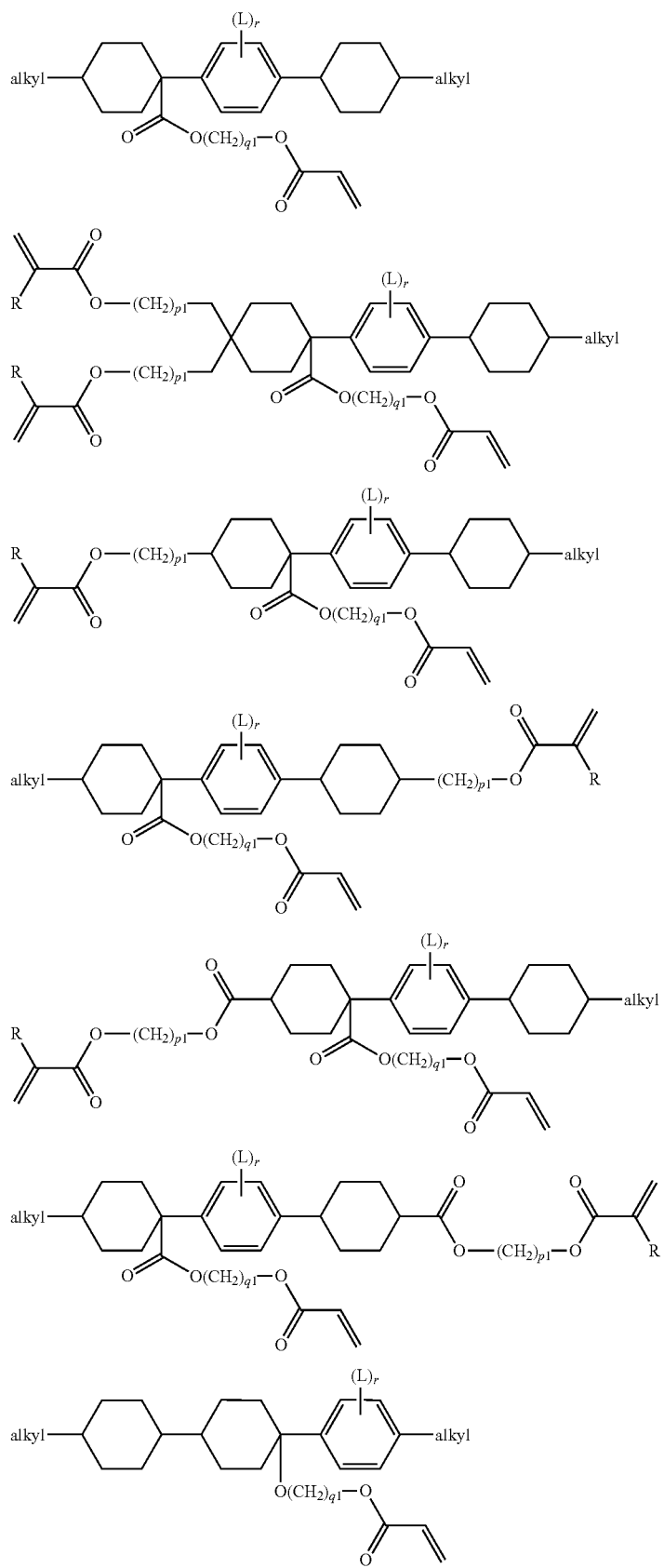

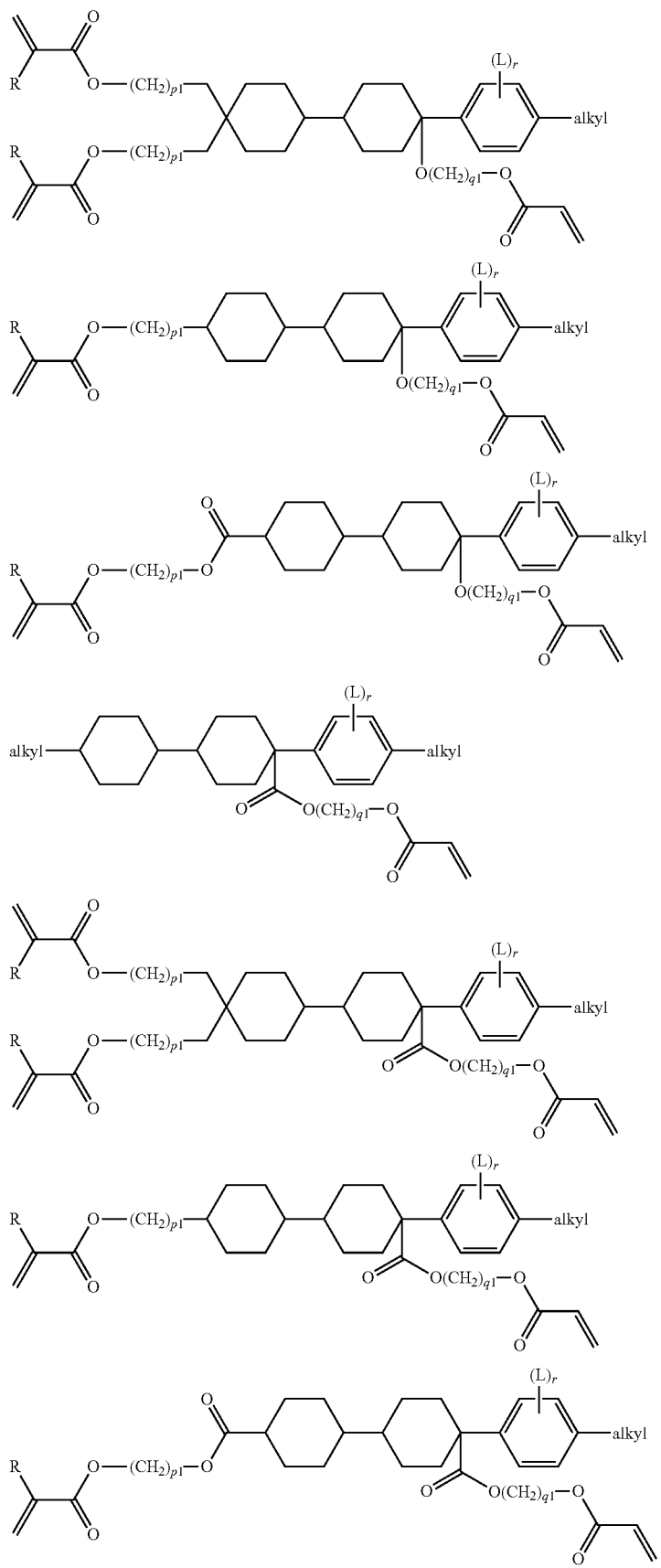

-continued
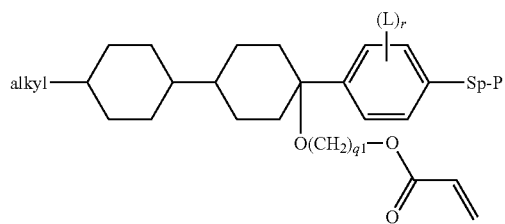
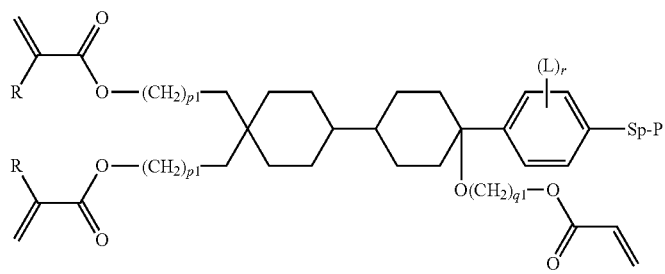
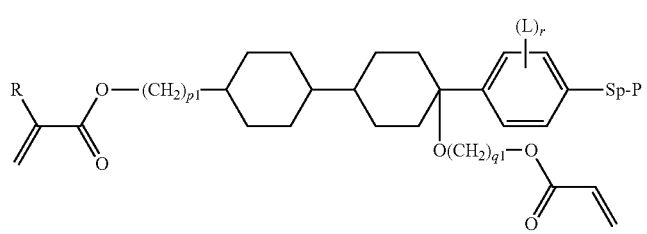
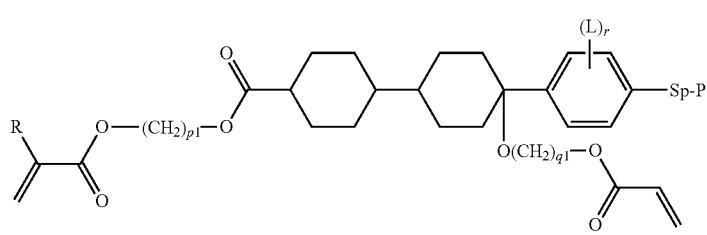
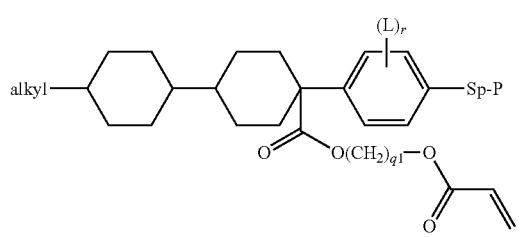
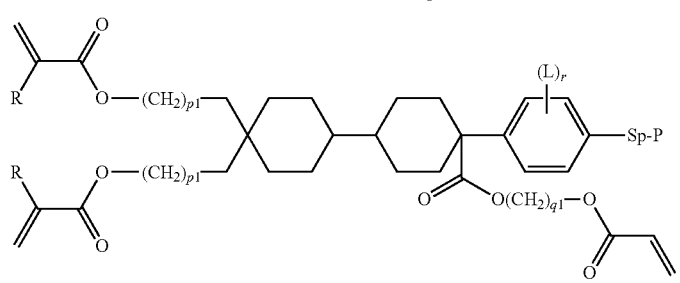
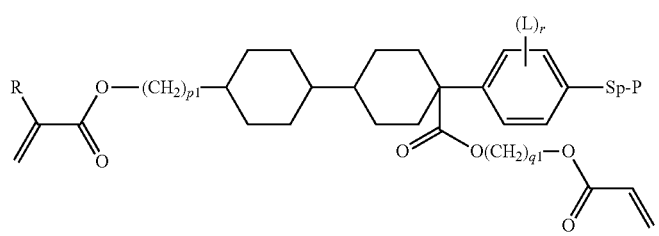

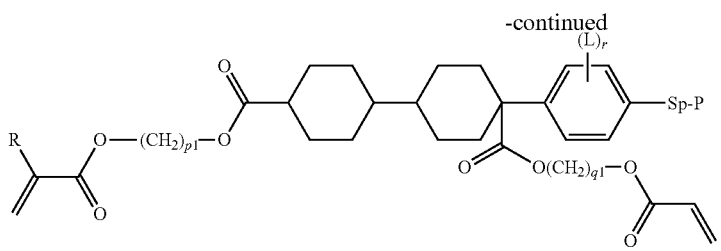

The synthesis of the compounds of the formula I according to the invention is explained below. In particular, the compounds of the formula I which contain, as preferred polymerisable group, groups of the acrylate type in which the polymerisable group P generally denotes a radical of the formula $CH_2=CW^1-COO-$, where $W^1$ is as defined above for formula I, are discussed. These very particularly preferably include acrylates ($CH_2=CH-OCO-$) and methacrylates ($CH_2=C(CH_3)-COO-$). The synthesis with other polymerisable end groups is carried out analogously using suitable methods which are familiar to the person skilled in the art. This means no difficulty in the preparation since the polymerisable groups are generally the last to be attached to the molecule.

The synthesis of the compounds I is carried out, for example, starting from dicarboxylic acids of type 3 (Scheme 1). These can be prepared from cyclohexyl ketones 1 by known processes [W. Schmidt, F. Vögtle, E. Poetsch, *Liebigs Ann.* 1995, 1319-1326].

Scheme 1: Synthesis of dicarboxylic acids of type 3

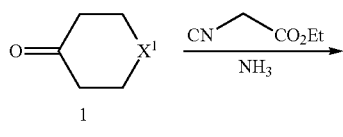

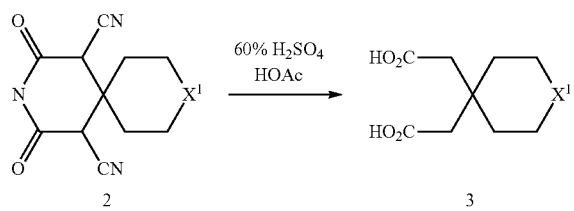

With these starting materials 3, the group $X=CH_2-(CO)-O$ is specified as part of the spacer Sp.

Esterification of the compounds 3 using haloalkanols 4 and subsequent reaction with acrylic acids 6 (R is preferably H or methyl) enables, for example, groups Sp composed of Sp'-X, where $X=-CH_2-COO-$ and $Sp'=-(CH_2)_{p1}-$, to be obtained (Scheme 2).

Scheme 2: Synthesis of compounds I where $X = -CH_2-C(O)O-$ and $Sp' = -(CH_2)_{p1}-$ (= 7). In this and following pictorial formulae, the radical $R^1$ corresponds to the radical $W^1$. R is preferably H or $CH_3$.

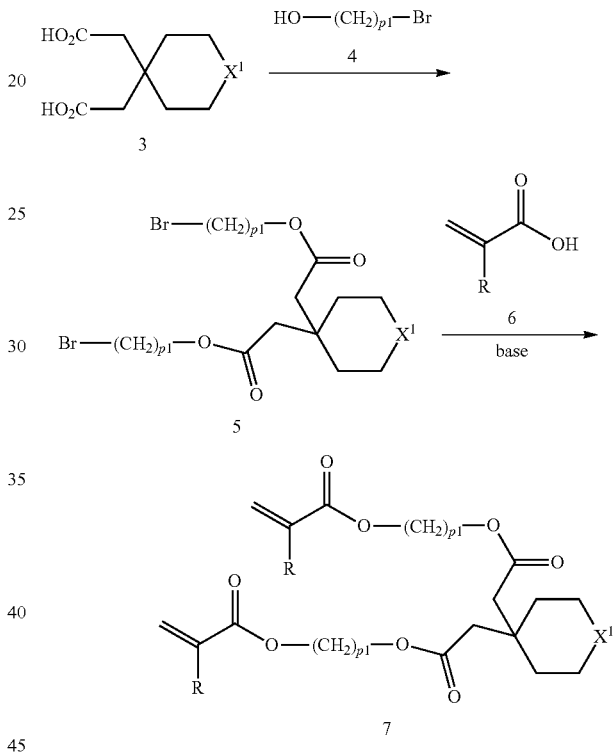

The synthesis from Scheme 2 can alternatively be carried out directly by esterification of the compounds 3 using compounds 8 (Scheme 3).

Scheme 3: Direct Synthesis of compounds I where $X = -CH_2-C(O)O-$ and $Sp' = -(CH_2)_{p1}-$ (= 7). In this pictorial formula, $W^1 = R$. R is preferably H or $CH_3$.

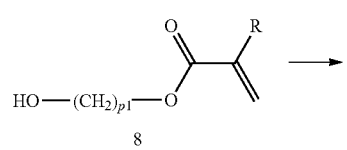

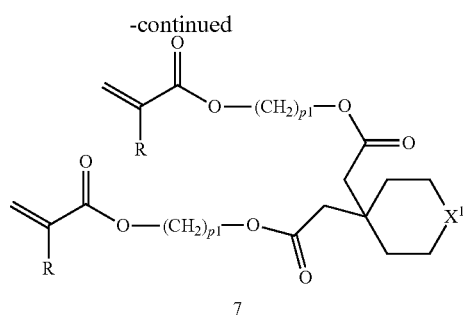

Reduction of the dicarboxylic acids 3, for example using lithium aluminium hydride, gives the diols 9 (Scheme 4).

Scheme 4: Synthesis of diols of type 9

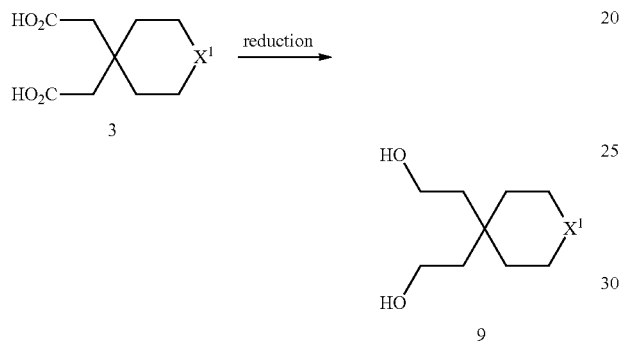

Diol compounds of type 9 can be converted into compounds of type I where Sp=—(CH$_2$)$_2$— (=compounds 11 in Scheme 5), for example directly by reaction with, for example, acryloyl chlorides 10 (R is preferably H or methyl).

Scheme 5: Synthesis of compounds I where Sp = ——(CH$_2$)$_2$—— (= 11). In this pictoral formula, W$^1$ = R. R is preferably H or CH$_3$.

The diols 9 here are also suitable starting materials for the preparation of compounds of type I where X=—(CH$_2$)$_2$—O— as part of the spacer Sp.

Esterification using haloalkylcarboxylic acids 12 to give the compounds 13 and subsequent reaction thereof with acrylic or methacrylic acid gives compounds I where Sp=—(CH$_2$)$_2$—O—(CO)—(CH$_2$)$_{p1}$— (=compounds 14 in Scheme 6).

Scheme 6: Synthesis of compounds I where Sp = ——(CH$_2$)$_2$—O——(CO)——(CH$_2$)$_{p1}$—— (= 14). In this pictoral formula, W$^1$ = R. R is preferably H or CH$_3$.

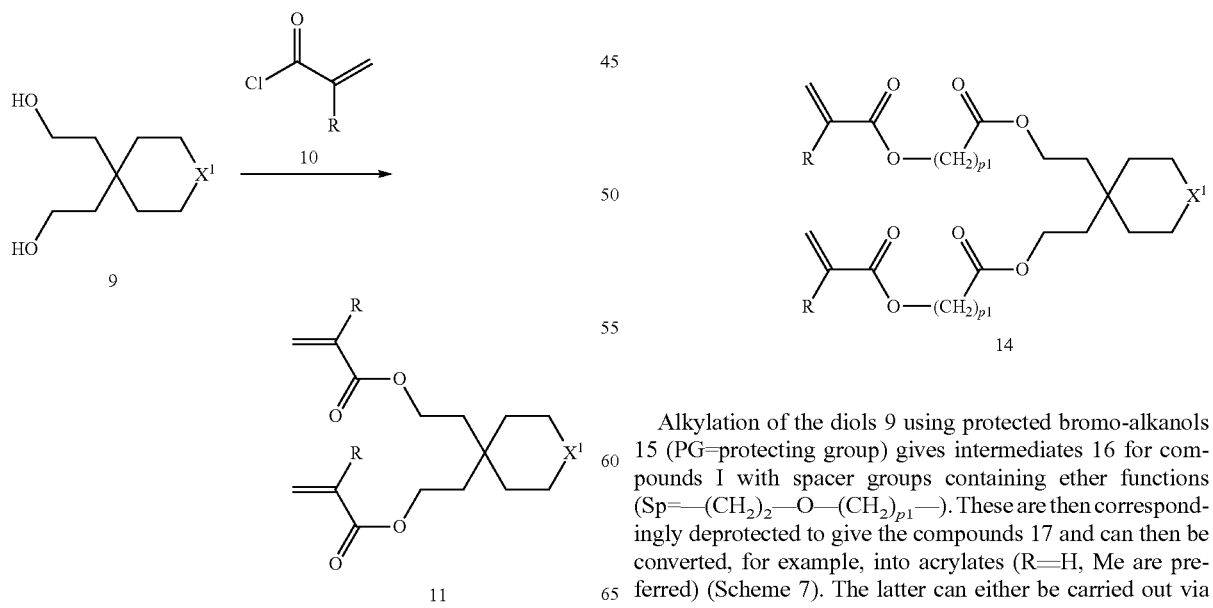

Alkylation of the diols 9 using protected bromo-alkanols 15 (PG=protecting group) gives intermediates 16 for compounds I with spacer groups containing ether functions (Sp=—(CH$_2$)$_2$—O—(CH$_2$)$_{p1}$—). These are then correspondingly deprotected to give the compounds 17 and can then be converted, for example, into acrylates (R=H, Me are preferred) (Scheme 7). The latter can either be carried out via DCC esterification using acrylic acids 6 (Method A) or by reaction with acryloyl chlorides 10 (Method B).

Scheme 7: Synthesis of compounds I where Sp = —(CH$_2$)$_2$—O—(CH$_2$)$_{p1}$— (=18). In this pictoral formula, W$^1$ = R. R is preferably H or CH$_3$.

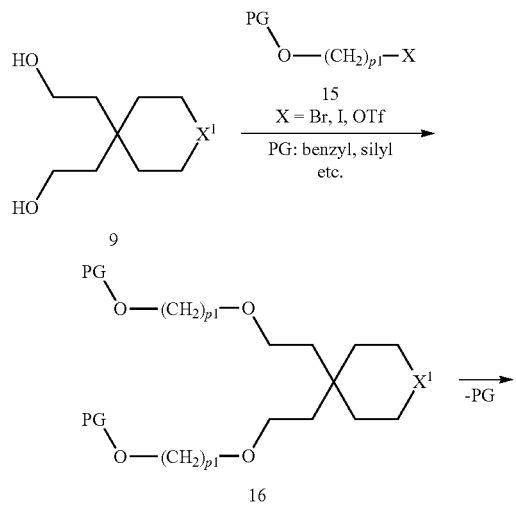

Scheme 8: Synthesis of dibromo compounds 19 and conversion thereof into compounds I where Sp = —(CH$_2$)$_2$—O—(CH$_2$)$_{p1}$— (=18). In this pictoral formula, W$^1$ = R. R is preferably H or CH$_3$.

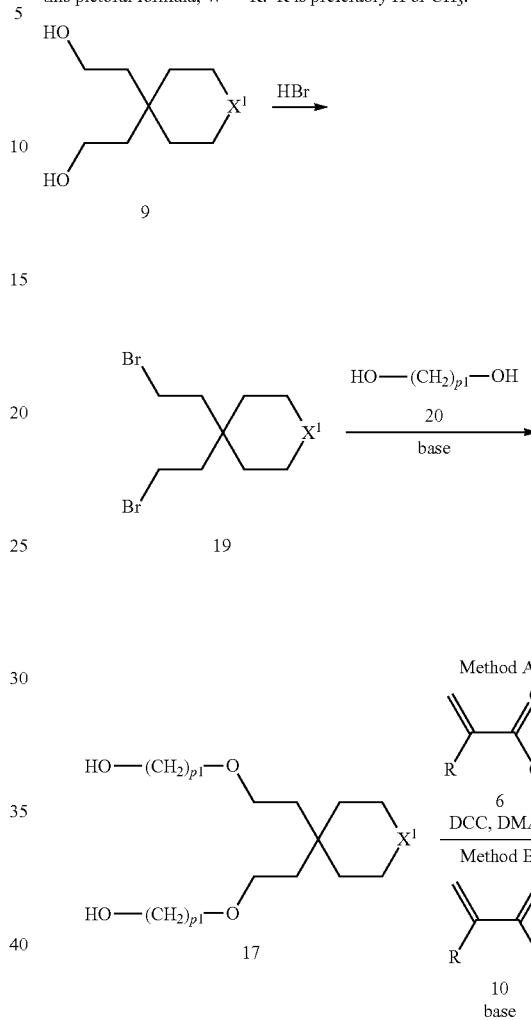

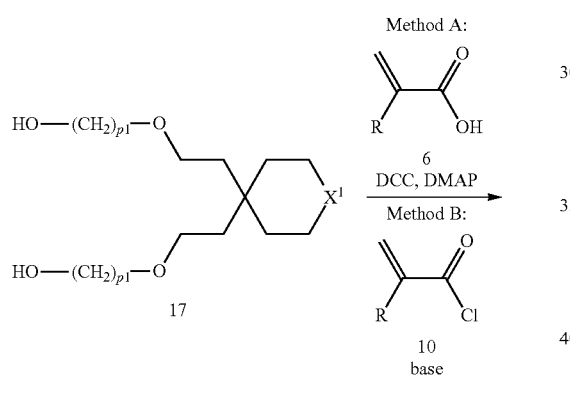

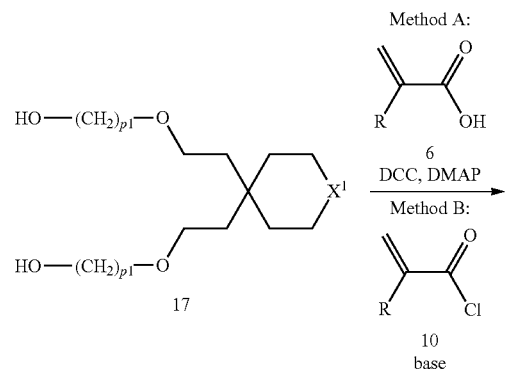

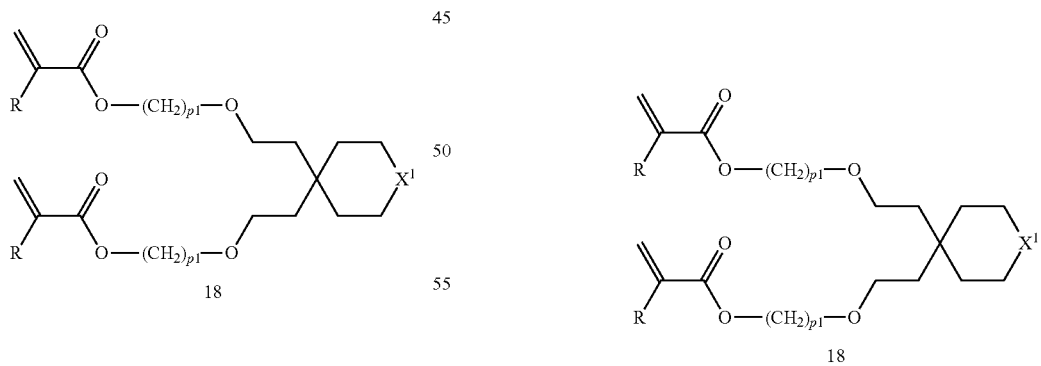

Compounds of the type of the formula 18 can also be prepared starting from the dibromides 19. These compounds are accessible from the diols 9 by reaction with, for example, hydrogen bromide [L. A. Karamysheva, T. A. Geivandova, et al. *Mol. Cryst. Liq. Cryst.* 1983, 99, 169-175]. A reaction can subsequently be carried out with suitable alcohols 20 to give the intermediates 17 (Scheme 8).

The dibromo compounds 19 can also undergo S$_N$ reactions with carbon nucleophiles, for example Grignard reagents 21. In this way, for example, the particularly preferred compounds containing alkyl spacers Sp=—(CH$_2$)$_2$—(CH$_2$)$_{p1}$— (=compounds 24 in Scheme 9) can be obtained. The requisite Grignard reagents 21 arise, for example, from the compounds 15.

Scheme 9: Synthesis of compounds I where Sp = ─(CH$_2$)$_2$(CH$_2$)$_{p1}$─ (= 24). In this pictoral formula, W$^1$ = R. R is preferably H or CH$_3$.

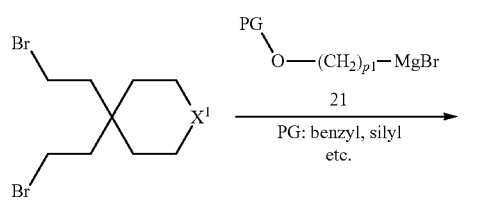

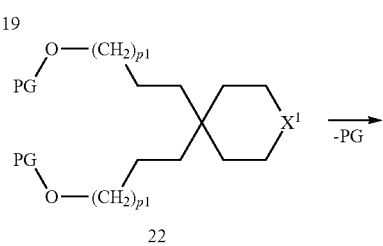

Further, multifunctionalisable intermediates are the dialdehydes 25. These can be obtained either by reduction of the diacid 3 or by oxidation of the diols 9 (Scheme 10).

Scheme 10: Syntheses of the dialdehydes 25

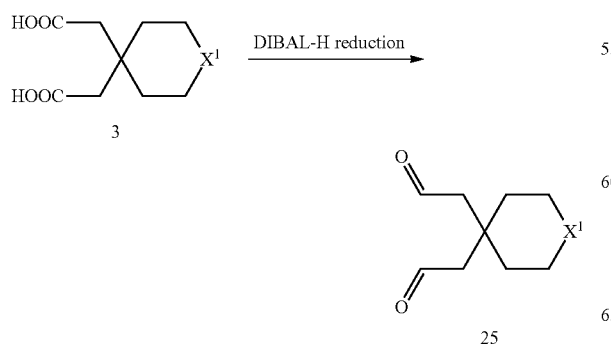

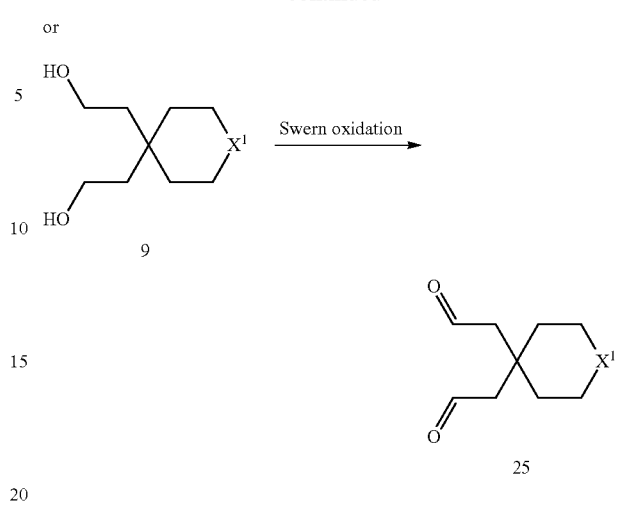

A Wittig reaction of the compounds of the formula 25, for example using reagents of type 26 (PG=protecting group, preferably silyl protecting group), then enables intermediates to be obtained for the synthesis of compounds of the formula I containing double bonds in the spacer group Sp (cf. compounds 29 in Scheme 11).

Scheme 11: Synthesis of compounds I where Sp = ─(CH$_2$)─C═C─(CH$_2$)$_{p1}$─ (= 29); PG denotes, for example, TBS, deprotection of TBS is carried out using TBAF. In this pictorial formula, W$^1$ = R. R is preferably H or CH$_3$.

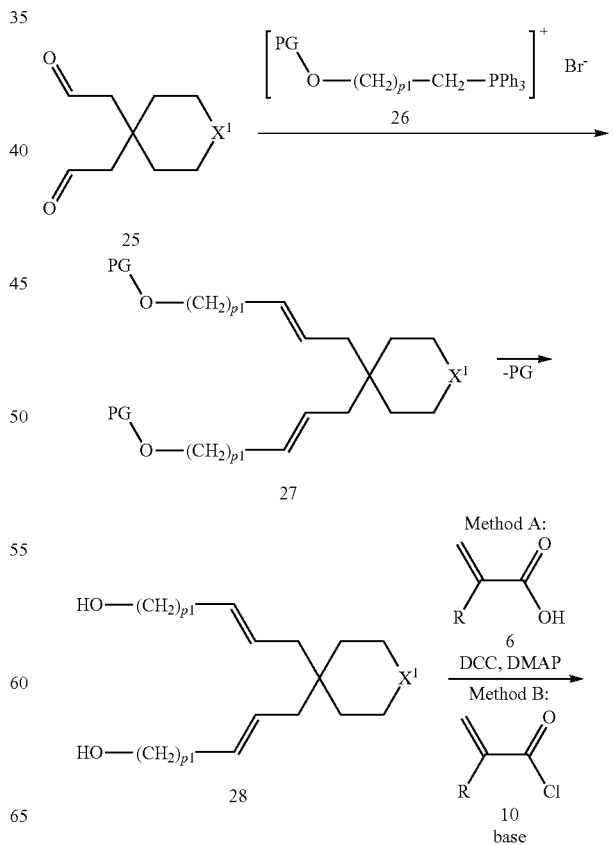

-continued

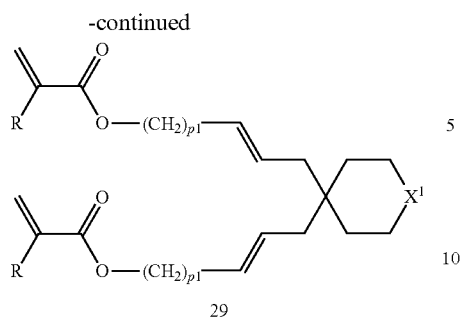

29

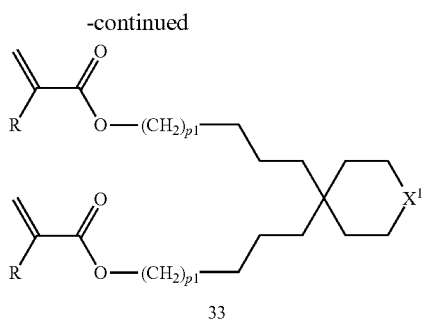

33

Wittig reagents of type 30 are particularly suitable if compounds containing alkyl spacers are to be prepared from the dialdehydes 25. The product of the Wittig reaction is hydrogenated, with the benzyl protecting group being cleaved off and the double bonds being hydrogenated. The process is outlined in Scheme 12.

In general, the use of protecting groups is not necessary for the synthesis of the intermediates 28 and 32. Wittig reagents of type 34 can also be used (Scheme 13).

Scheme 12: Synthesis of compounds I where Sp = —(CH$_2$)$_3$(CH$_2$)$_{p1}$— (= 33) from the dialdehydes 25. In this pictorial formula, W$^1$ = R. R is preferably H or CH$_3$.

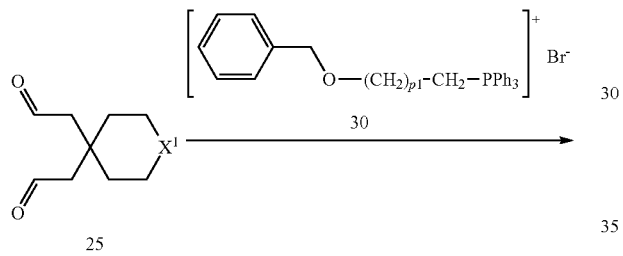

25

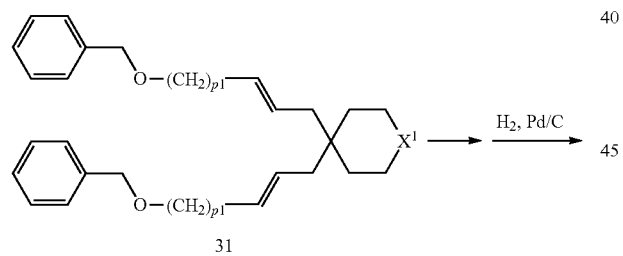

31

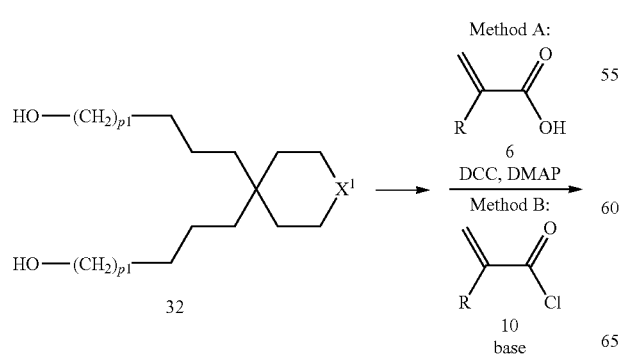

32

Scheme 13: Synthesis of the intermediates 28 and 32 from the dialdehydes 25

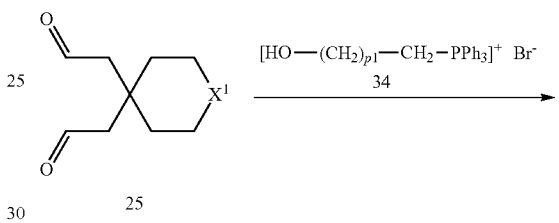

25

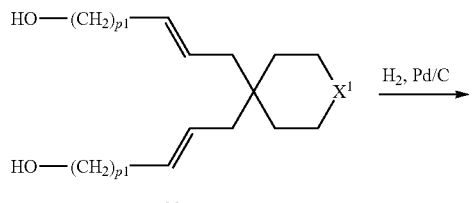

28

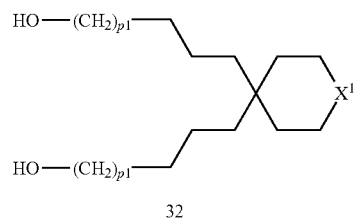

32

Further preferred reagents for the synthesis of the compounds I where Sp=—(CH$_2$)—C═C—(CH$_2$)$_{p1}$— or Sp=—(CH$_2$)$_3$(CH$_2$)$_{p1}$— are bromoalkyl Wittig salts 35. The Wittig reaction of the dialdehydes 25 gives the compounds 36, which can then be reacted, for example, with acrylic acids 6 in the presence of base to give compounds I where Sp=—(CH$_2$)—C═C—(CH$_2$)$_{p1}$— (cf. compounds 29 in Scheme 14).

Scheme 14: Synthesis of compounds I where Sp = —(CH$_2$)—C≡C—(CH$_2$)$_{p1}$— (= 29) from the dialdehydes 25 using bromoalkyl Witting salts. In this pictorial formula, W$^1$ = R. R is preferably H or CH$_3$.

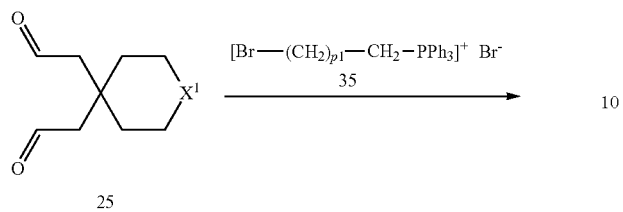

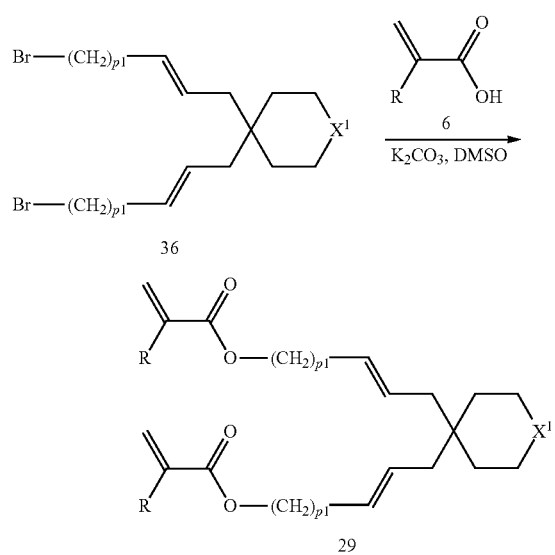

In order to obtain compounds I where Sp=—(CH$_2$)$_3$ (CH$_2$)$_{p1}$— (cf. compounds 33 in Scheme 15) in this way, the intermediates 36 are hydrogenated. This is followed by the reaction of the resultant compounds 37 with acrylic acids 6 (Scheme 15).

Scheme 15: Synthesis of compounds I where Sp = —(CH$_2$)$_3$(CH$_2$)$_{p1}$— from the intermediates 36. In this pictorial formula, W$^1$ = R. R is preferably H or CH$_3$.

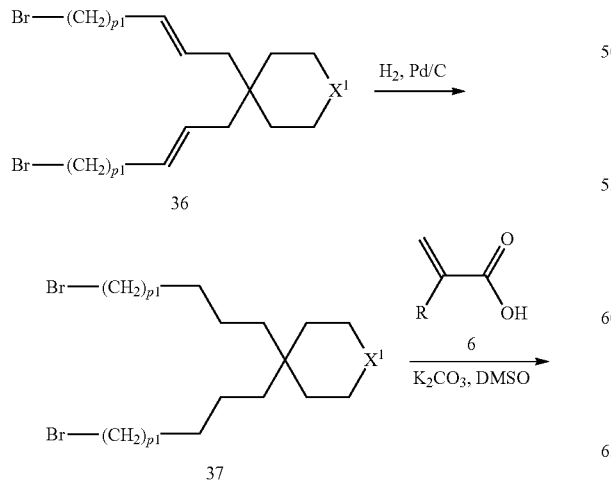

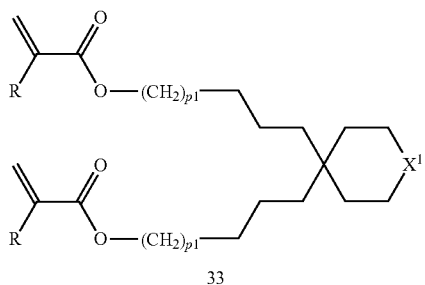

33

The syntheses depicted in Schemes 1-15 should be regarded as illustrative. The person skilled in the art will easily be able to apply the methods described to other starting materials or to vary the end groups involved. The polymerisable end groups and spacers can be replaced by other known radicals. The starting materials, reagents and methods shown can be combined or supplemented in a suitable manner and a multiplicity of possible compounds of type I can thus be obtained.

Furthermore, particularly preferred compounds containing —(CH$_2$)$_{p1}$— units are explicitly described in the schemes shown above (for example 2-3, 6-9, 11-15). The methods enable, for example, the compounds below in Scheme 16 to be obtained using corresponding reagents starting from the intermediates 3, 9, 19 and 25:

Scheme 16: Synthesis of compounds I (= especially 38-43) starting from 3, 9, 19 and 25. In this pictorial formula. W$^1$ = R. R is preferably H or CH$_3$.

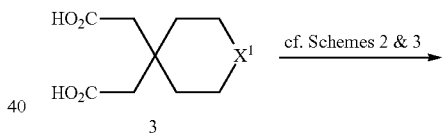

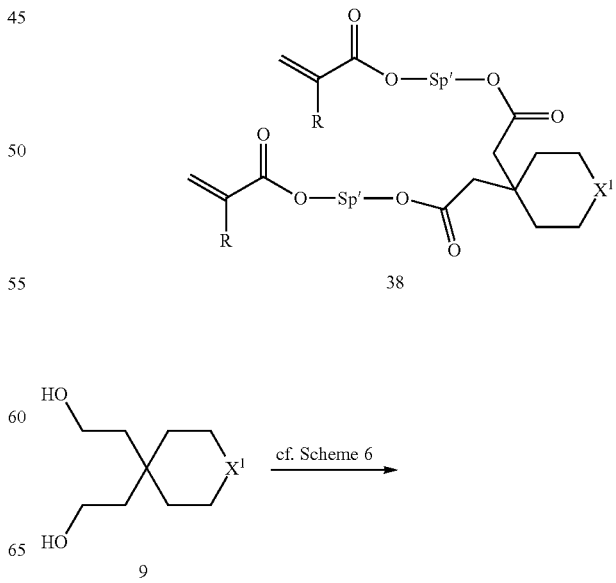

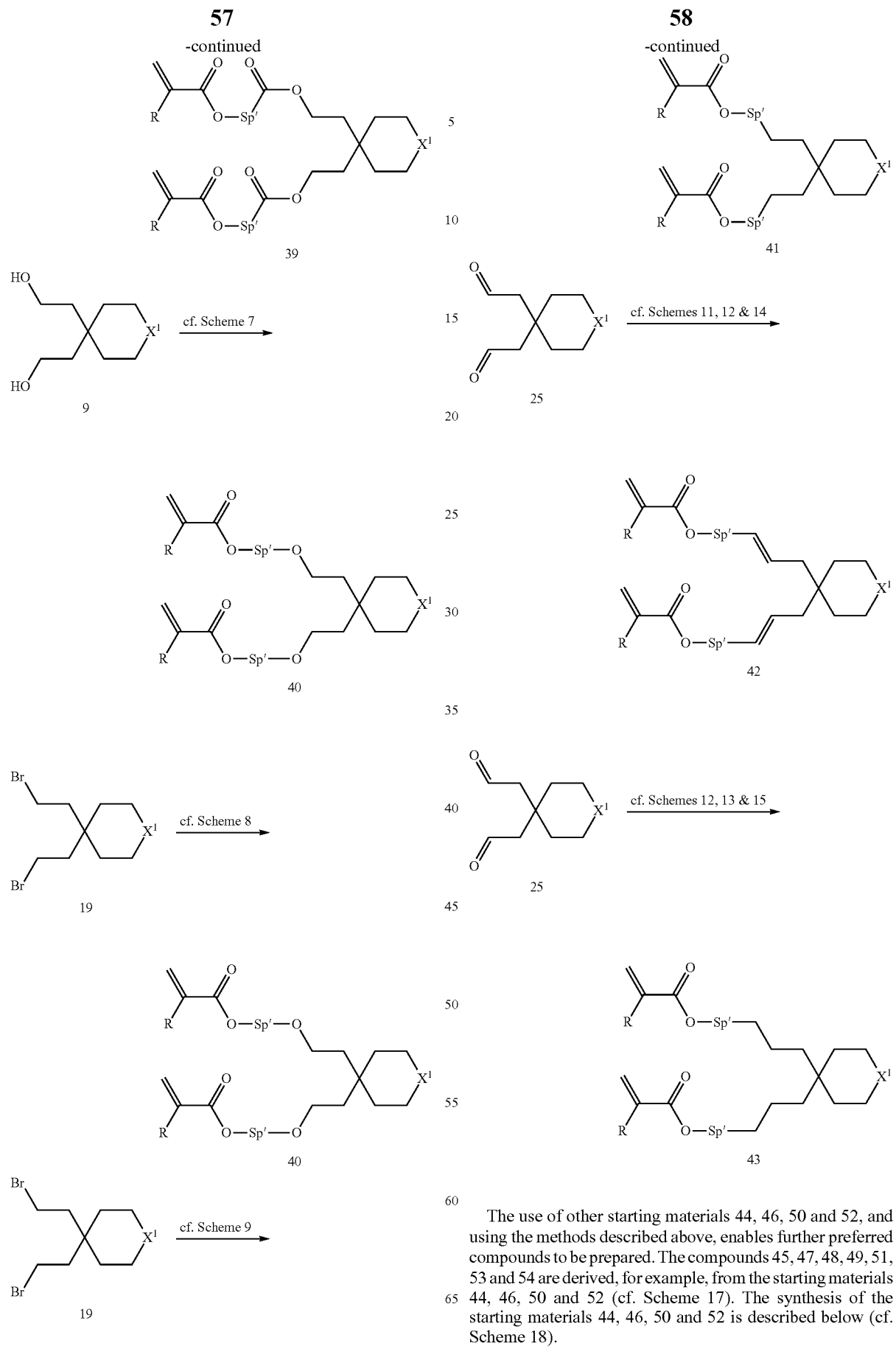
The use of other starting materials 44, 46, 50 and 52, and using the methods described above, enables further preferred compounds to be prepared. The compounds 45, 47, 48, 49, 51, 53 and 54 are derived, for example, from the starting materials 44, 46, 50 and 52 (cf. Scheme 17). The synthesis of the starting materials 44, 46, 50 and 52 is described below (cf. Scheme 18).

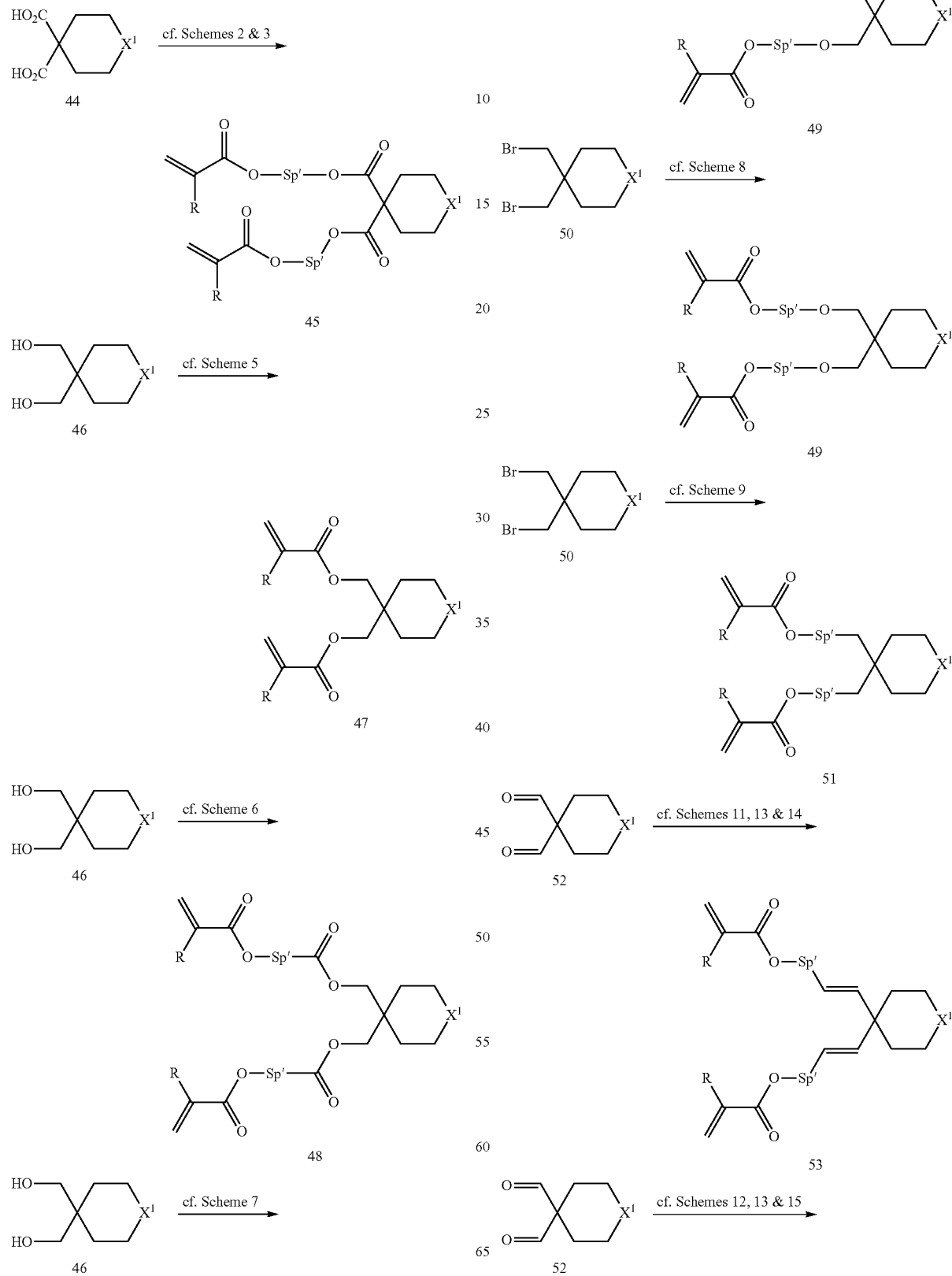

reacted with methyl chloroformate with formation of the compound 59. The latter can then be saponified to give the tetracarboxylic acid 60.

The compounds 44, 46, 50 and 52 are synthesised starting from cyclo-hexylcarboxylic acid esters 55 (cf. Scheme 18). The enolates obtained by deprotonation using LDA are reacted with $CO_2$. The resultant compounds 56 are then saponified to give the dicarboxylic acids 44.

The dicarboxylic acids 44 can then be reduced to the corresponding diols 46, for example using lithium aluminium hydride as reducing agent. The dicarboxylic acids 44 can also be starting materials for the dialdehydes 52 if DIBAL-H is used as reducing agent. However, oxidation of the diols 46, for example via a Swern oxidation, is often more advantageous. The diols 46 are then also starting materials for the synthesis of the dibromides 50.

Further preferred starting materials for the synthesis of the compounds I are described in the literature. The synthesis of tetracarboxylic acids 60 can be carried out starting from dicarboxylic acid esters 57 [C. R. Davis, D. C. Swenson, D. J. Burton, *J. Org. Chem.* 1993, 58, 6843-6850].

The dicarboxylic acid ester 57, the methyl ester is depicted here by way of example, is deprotonated using LDA, and the enolate of the compound is reacted with chloroformic acid ester (Scheme 19). An enolate is then formed from 58 through the use of LiTMP as base. The enolate formed is in turn The tetracarboxylic acid 60 can then be used as starting material for compounds I. This is depicted by way of example in Scheme 20.

Scheme 20: Synthesis of compounds I (especially 61) starting from the tetracarboxylic acid 60. In this pictoral formula, $W^1$ = R. R is preferably H or CH$_3$.

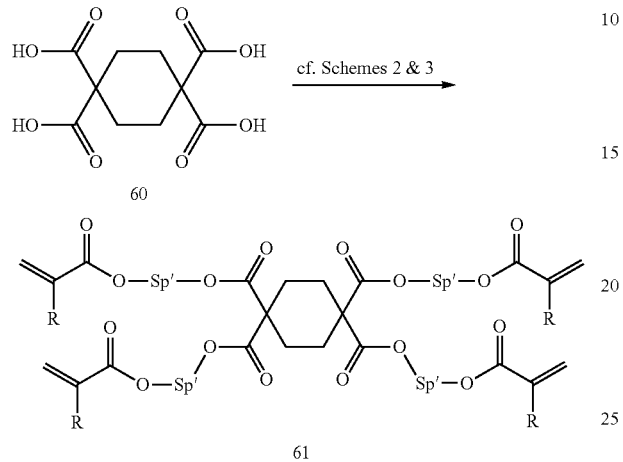

The synthesis of further intermediates for the synthesis of compounds I starts from the tetracarboxylic acid ester 59 (Scheme 21, line 1). In principle, the tetracarboxylic acid 60 is also suitable for the synthesis of the compounds 62, 63 and 64 (Scheme 21, lines 2-3). However, the tetracarboxylic acid ester 59 is easier to handle. The tetraaldehyde 63 and the tetrabromide 64 are derived, for example, from the tetraol 62.

Scheme 21: Synthesis of compounds 62, 63 and 64 derived from the tetracarboxylic acid ester 59 as starting materials for compounds of the formula I

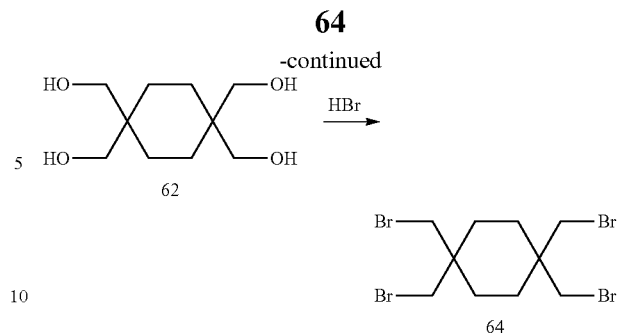

The possible uses of the compounds 62, 63 and 64 are outlined in Scheme 22.

Scheme 22: Examples of compounds I derived from the intermediates 62, 63 and 64. In this pictorial formula, $W^1$ = R. R is preferably H or CH$_3$.

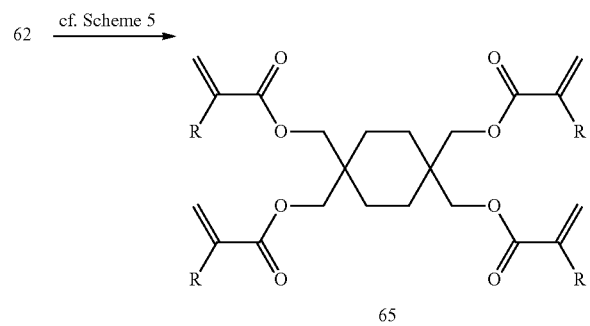

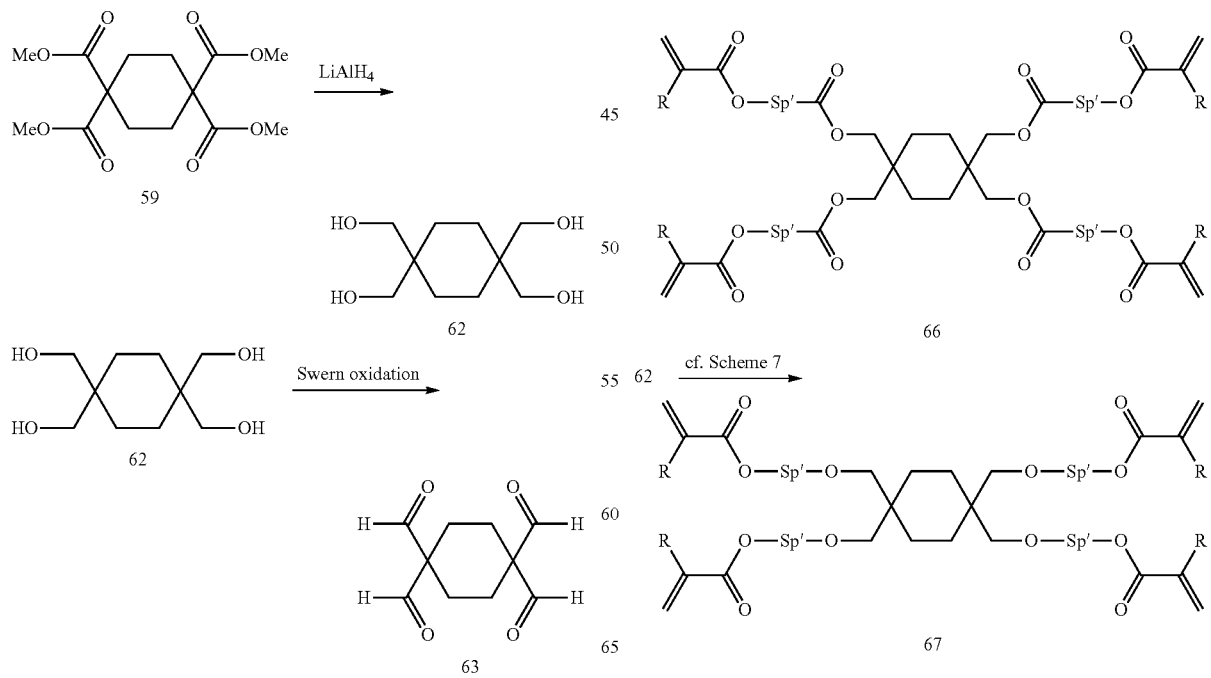

64 →(cf. Scheme 8)

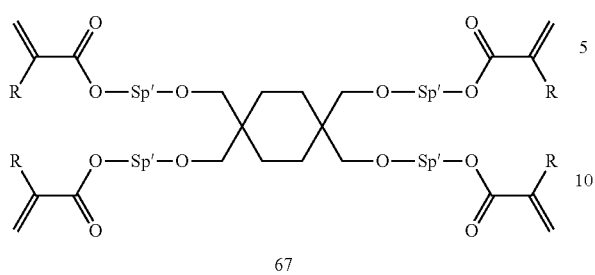

67

64 →(cf. Scheme 9)

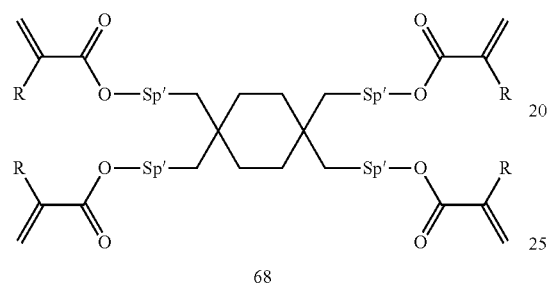

68

63 →(cf. Schemes 11, 13 & 14)

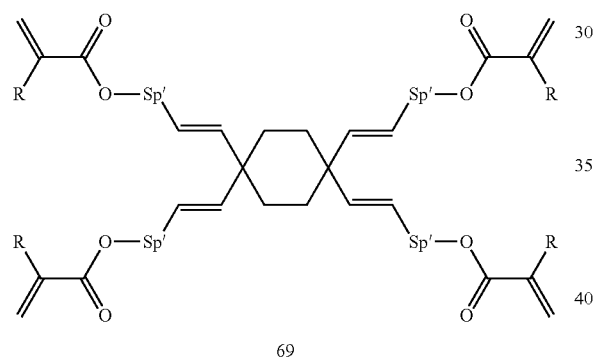

69

63 →(cf. Schemes 12, 13 & 15)

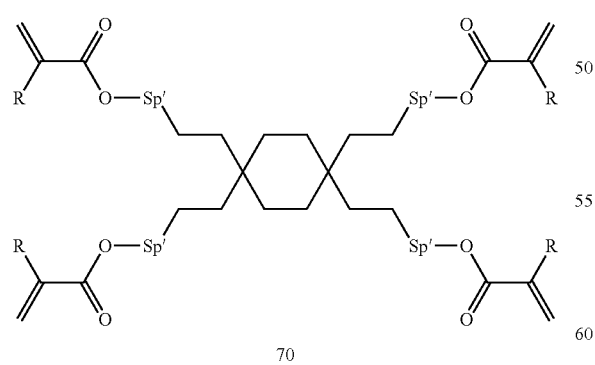

70

The reactions depicted in Schemes 18-22 should be regarded as illustrative. The syntheses can also be applied to starting materials having more than one ring element (Schemes 23-29).

Scheme 23: Synthesis of tetracarboxylic acid esters 72

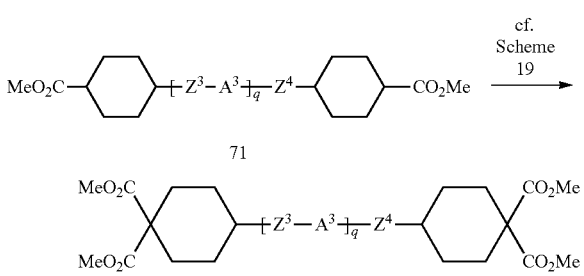

72

Scheme 24: Compounds 73, 74, 75 and 76 derived from the tetracarboxylic acid esters 72

72 →(saponification)

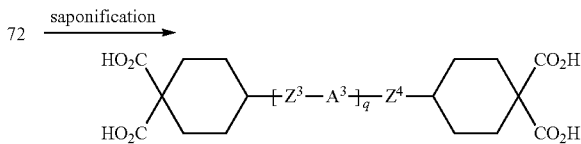

73

72 →(reduction)

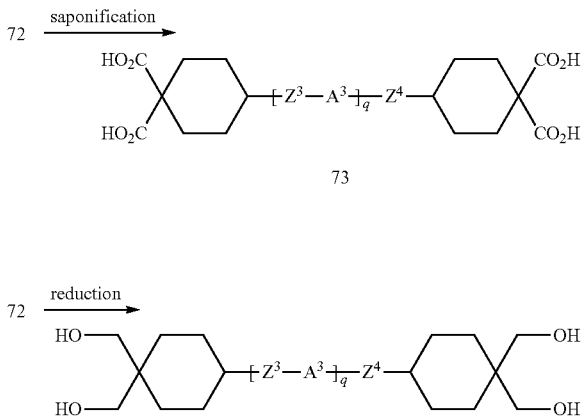

74

74 →(oxidation)

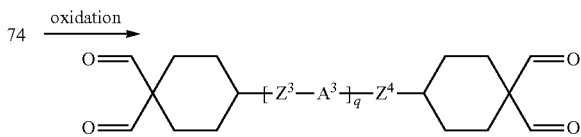

75

74 →(HBr)

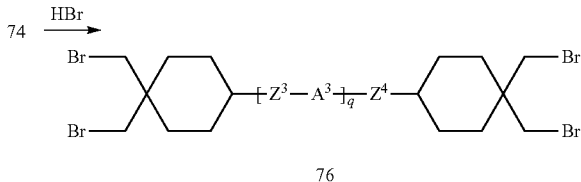

76

Particular preference is given to the use of compounds 73-76 in which $Z^2$-$A^2$ represents a single bond or a 1,4-cyclohexyl radical. These intermediates can then in turn give compounds of type I analogously to Scheme 20 and Scheme 22. This is only explained here with reference to two possible examples (cf. Scheme 25).

Schem 25: Illustrative synthesis of compounds I (especially 77 and 78) starting from the intermediates 73 and 74 respectively. In this pictorial formula, $W^1$ = R. R is preferably H or $CH_3$.

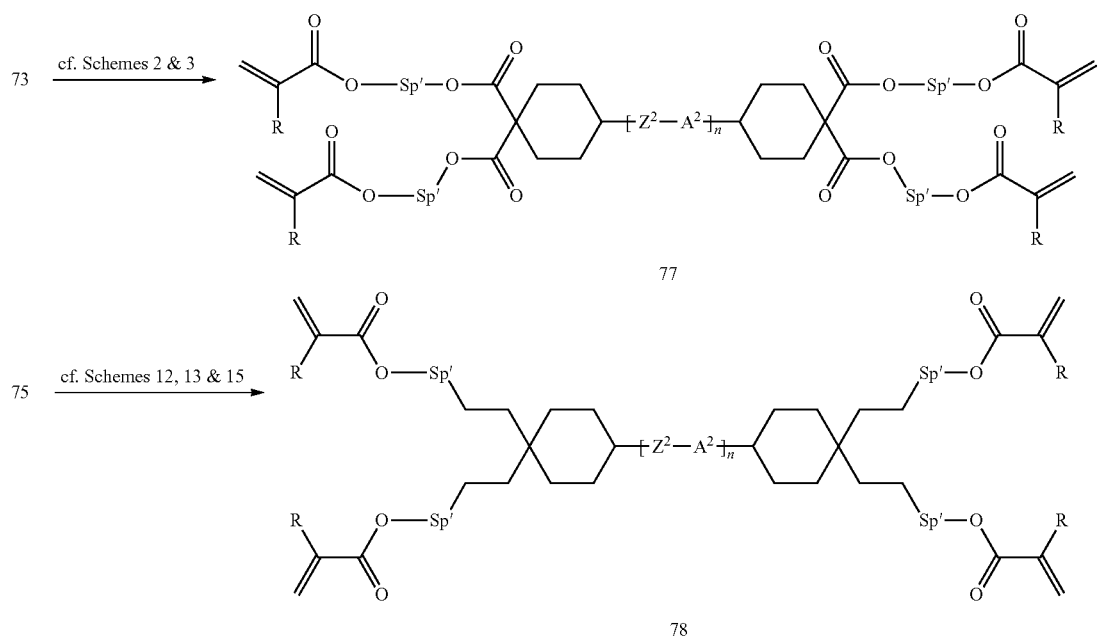

The synthesis sequences shown above allow the synthesis of compounds of type I containing two or four identical groups Sp-P. These compounds are preferred compounds in the sense of the present invention.

However, compounds containing different groups Sp-P can also be built up via the carboxylic acid esters 79. This possibility is depicted by way of example in Scheme 26.

Scheme 26: Synthesis of compounds 85. In this pictorial formula, $W^1$ = R. R is preferably H or $CH_3$.

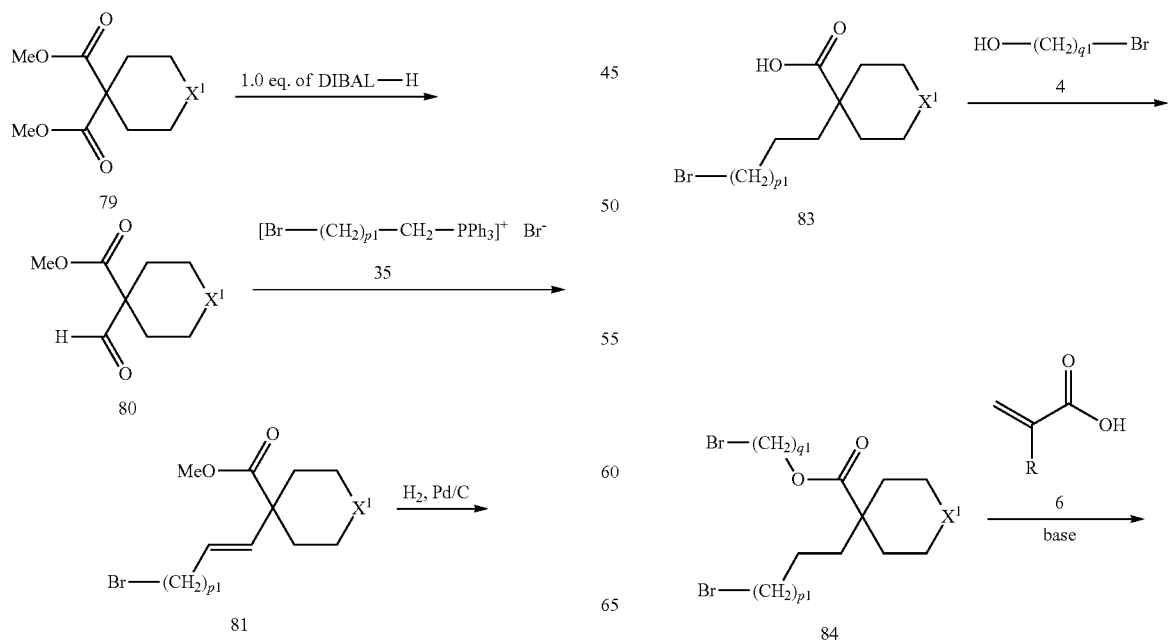

-continued

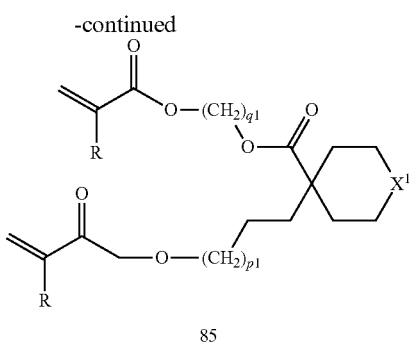

85

Reaction with DIBAL-H initially only reduces one ester group, for example, to the aldehyde. Starting from the aldehyde function, the spacer can be built up by one of the methods described above. This is depicted by way of example in Scheme 26 for a Wittig reaction with a reagent of type 35 and subsequent hydrogenation. The remaining ester function in the compounds 81 can then be converted into another spacer by one of the methods from Schemes 2-17. A spacer of the same type as above, only with, for example, a different chain length, or alternatively a completely different spacer can be selected here. The latter possibility is depicted by way of example in Scheme 26. Here, a spacer of the type Sp=—(CO)O—$(CH_2)_{q1}$— is built up by saponification and subsequent esterification using a bromo-alkanol 4. Finally, the acrylate groups are then introduced to give the compounds 85.

The person skilled in the art will be able to combine the starting materials, reagents and methods shown in a suitable manner and thus obtain a multiplicity of possible compounds of type I. At this point, the synthesis of particularly preferred starting materials 88-102 for trireactive compounds of the formula I will be depicted.

Scheme 27: Examples of starting materials for trireactive compounds I

Compounds 88

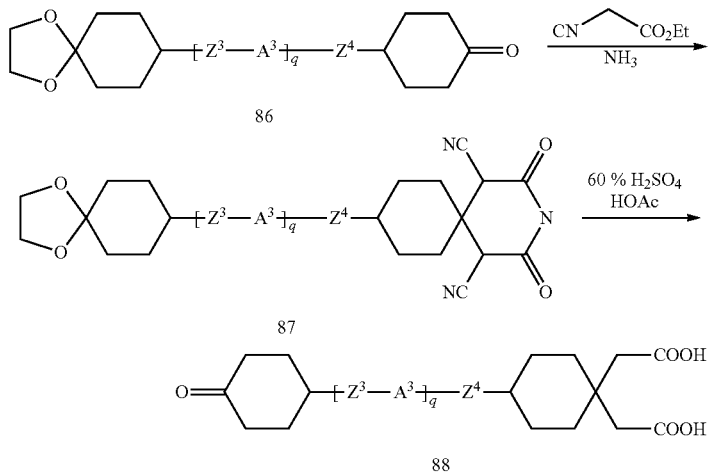

Compounds 89

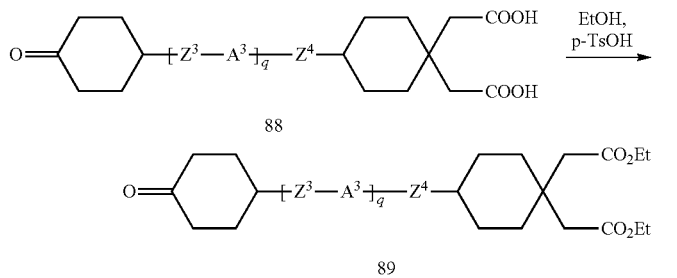

Compounds 90

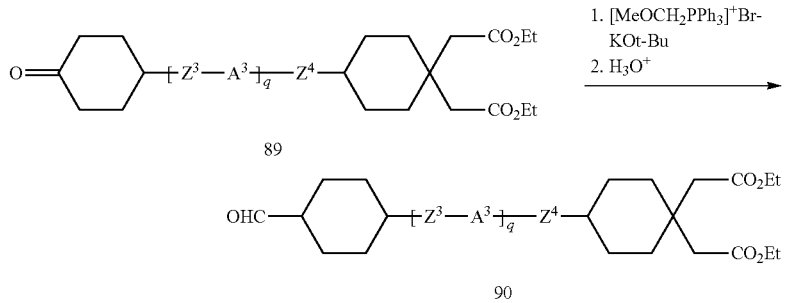

-continued
Compounds 91
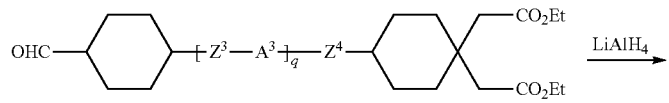
90
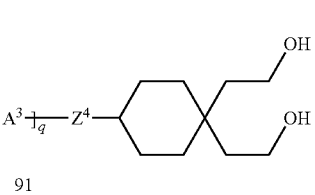
91
Compounds 92
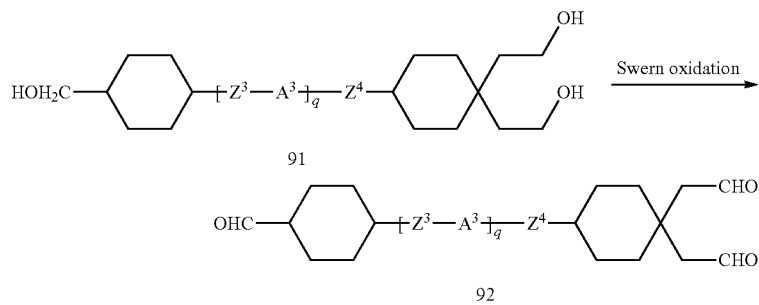
91
92
Compounds 93
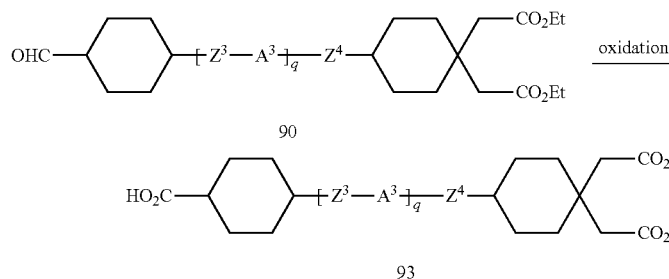
90
93
Compounds 94
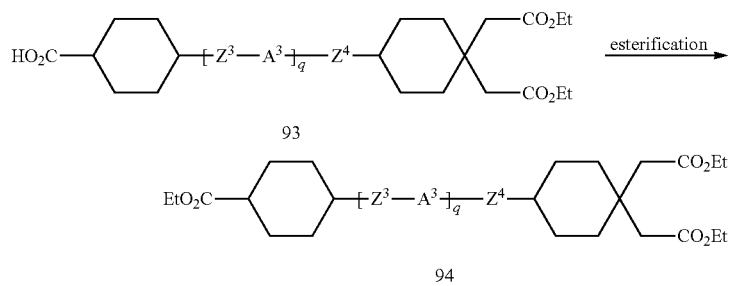
93
94
Compounds 96
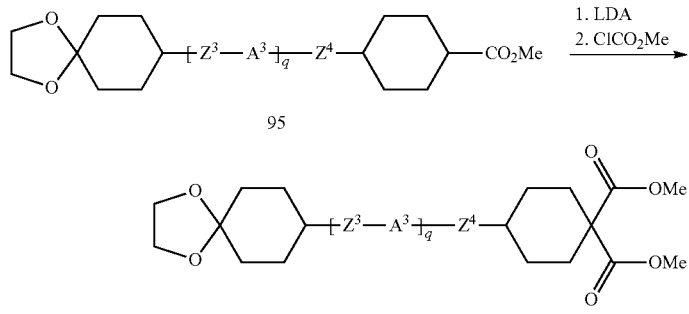
95
96

Compounds 97
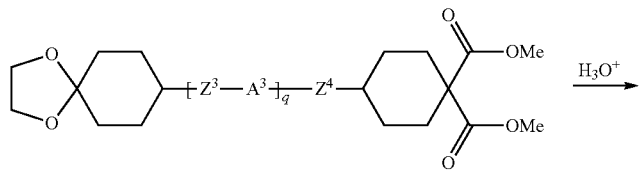
96
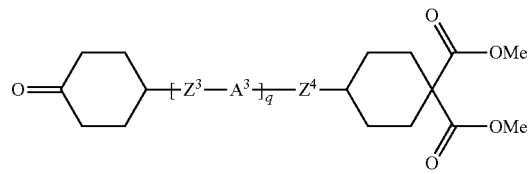
97
Compounds 98
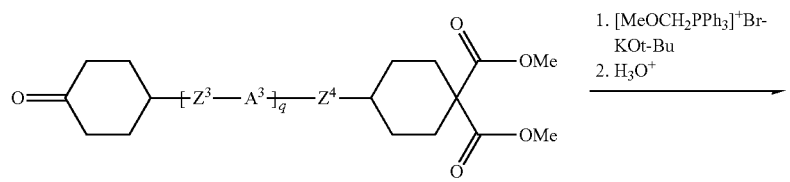
97
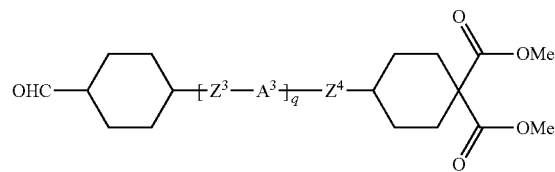
98
Compounds 99
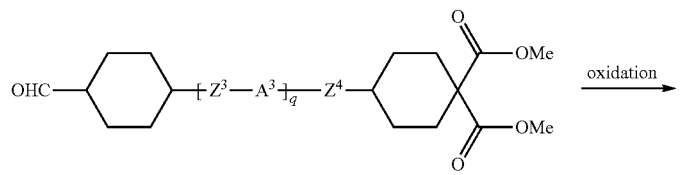
98
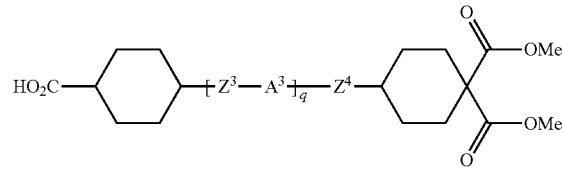
99
Compounds 100
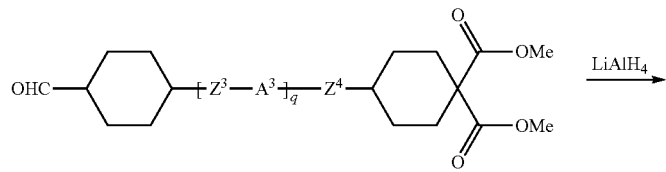
98

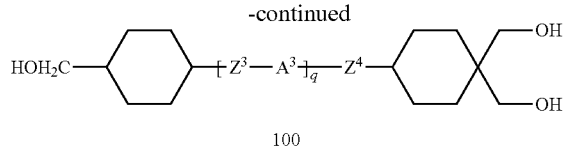
100
Compounds 101
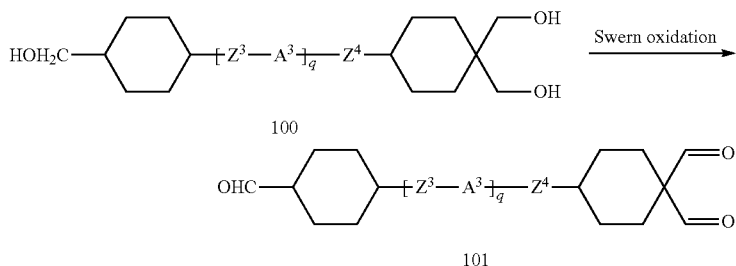
Compounds 102
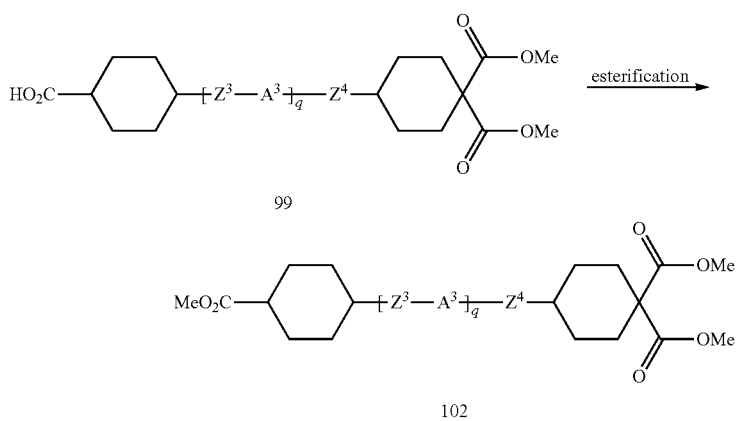
The following particularly preferred starting materials or intermediates 103-122 are obtainable in the same or a similar manner.
Scheme 28: Further examples of starting materials for trireactive compounds I
103
104
105
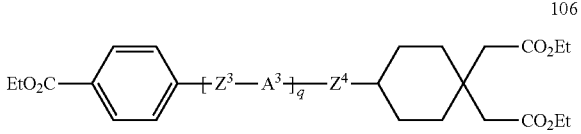
106
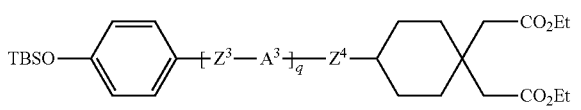
107
108
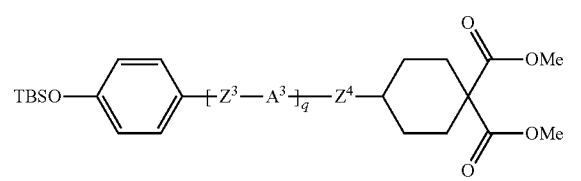
109
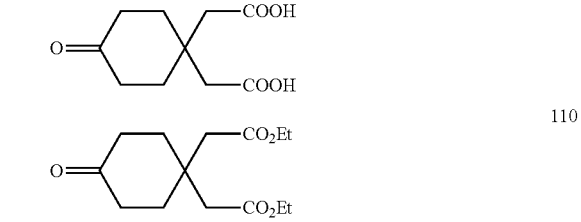
110
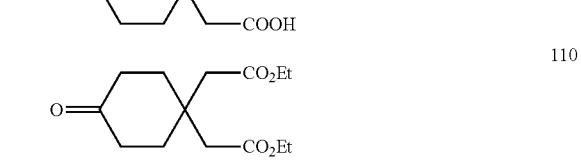

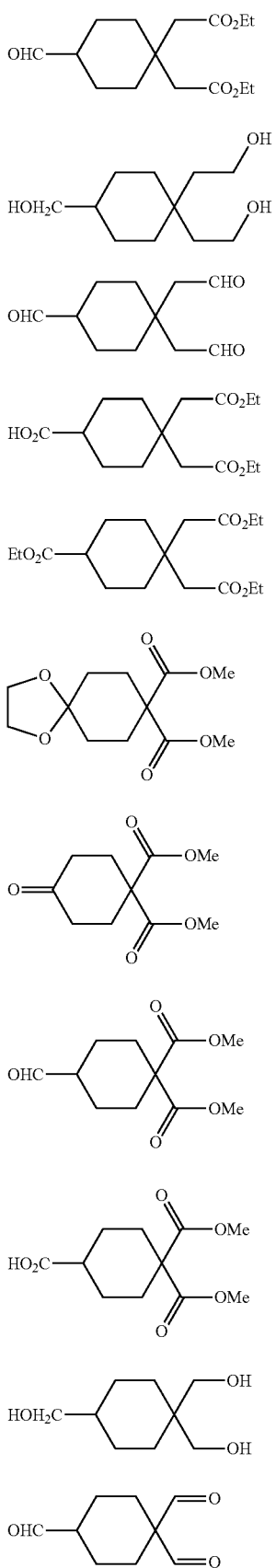

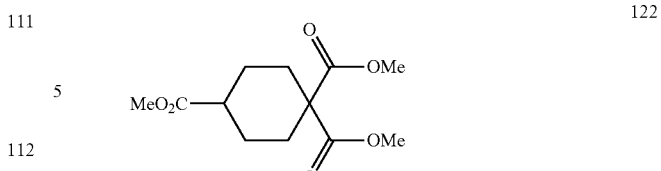

Further preferred compounds I are also obtained starting from cyclohexyl ketones. It is again possible here to introduce different spacers. As one possibility, the addition of Grignard reagents of type 21 is outlined (Scheme 29).

Scheme 29: Example of intermediates for the synthesis of the compounds I derived from cyclohexyl ketones 123

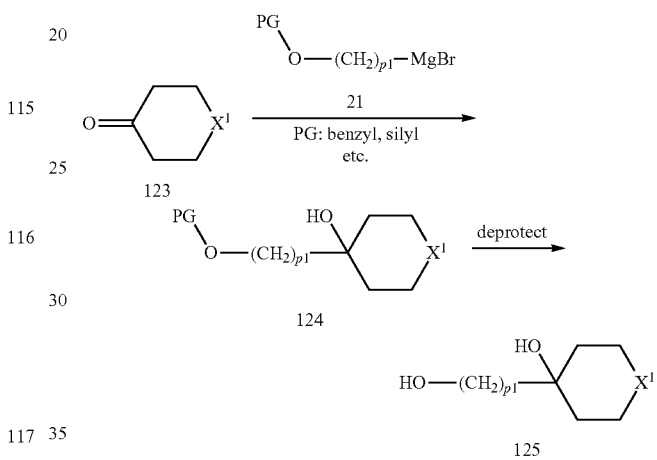

Starting from the compounds 125, the spacers can then be built up successively, for example using the methods described above. Scheme 30 illustrates this again by way of example with reference to an esterification using a bromoalkanoic acid 12.

Scheme 30: Synthesis of the compounds 127. In this pictorial formula, $W^1$ = R. R is preferably H or $CH_3$.

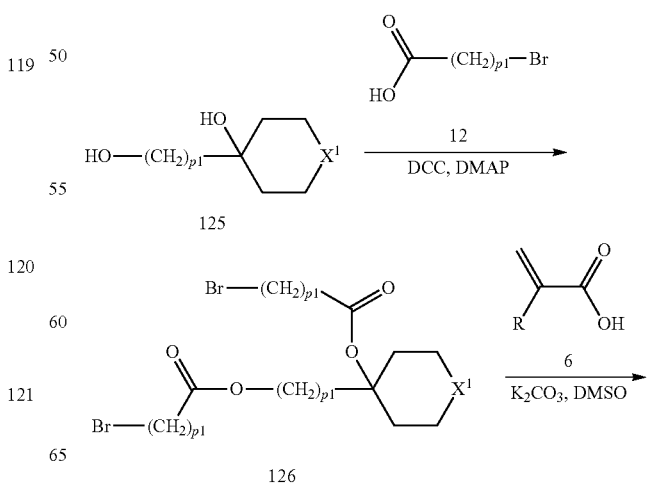

-continued
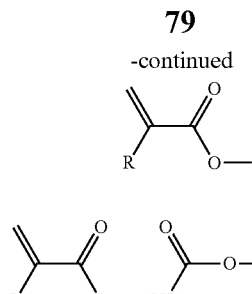
127
Diones are of course also suitable reaction partners for the above reactions (cf. Scheme 31).
Scheme 31: Synthesis of the compounds 132 and 134. In this pictorial formula, $W^1$ = R. R is preferably H or $CH_3$.
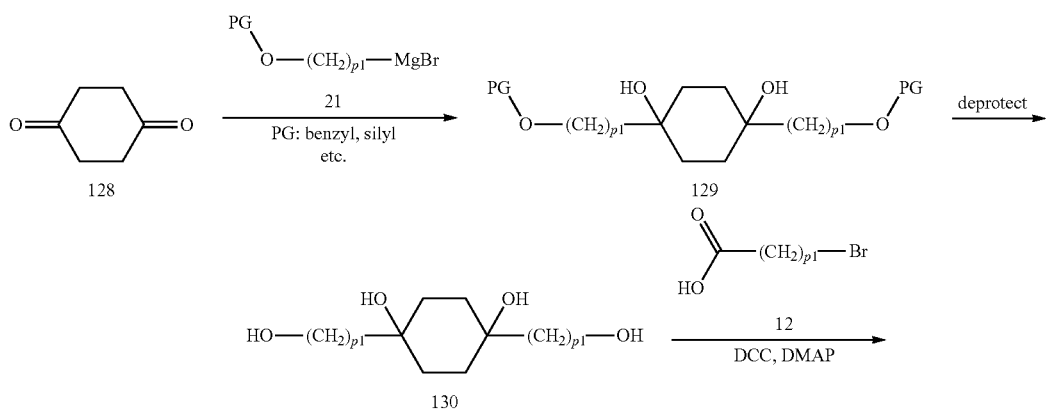
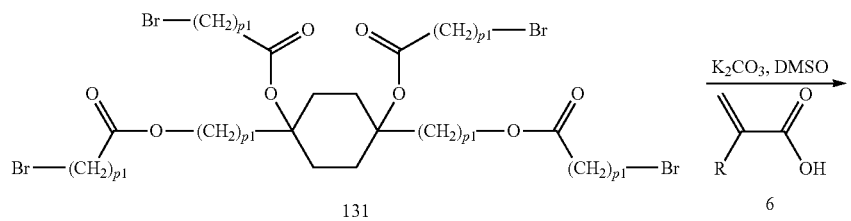
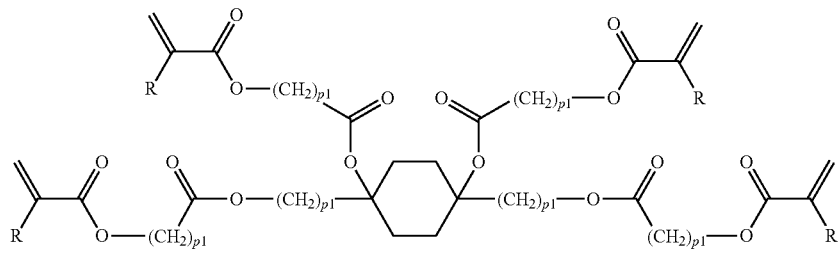
132
analogously
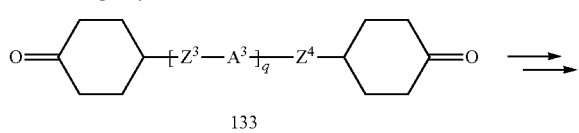
133

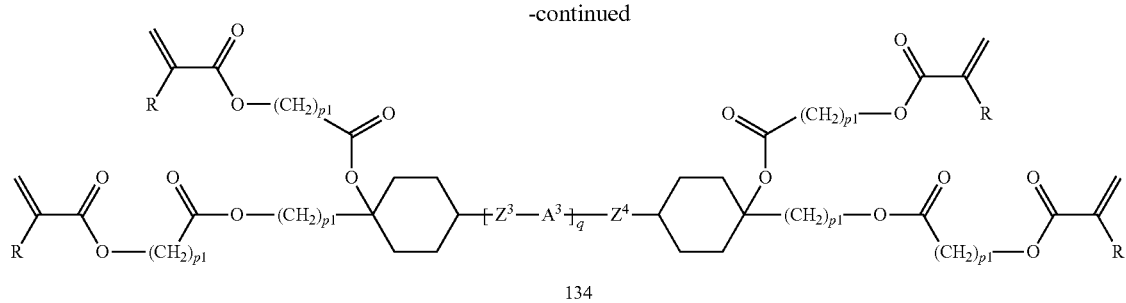

134

Compounds of the formula I

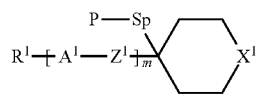

for which m is not equal to 0 and $A^1$ denotes a cyclohexyl or aryl radical are prepared, for example, as described in Schemes 32 and 33 (compounds 137 and 140). To this end, firstly a cyclohexyl Grignard reagent (or an aryl Grignard reagent) is added onto cyclohexyl ketones 123. The hydroxyl group, which is preferably in the axial orientation, of the compounds 136 and 139 is then suitably derivatised.

Scheme 32: Synthesis of the compounds 137. In this pictorial formula, $W^1$ = R. R is preferably H or $CH_3$.

Scheme 33: Synthesis of the compounds 140. In this pictorial formula, $W^1$ = R. R is preferably H or $CH_3$.

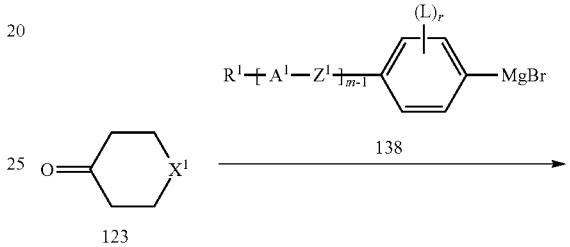

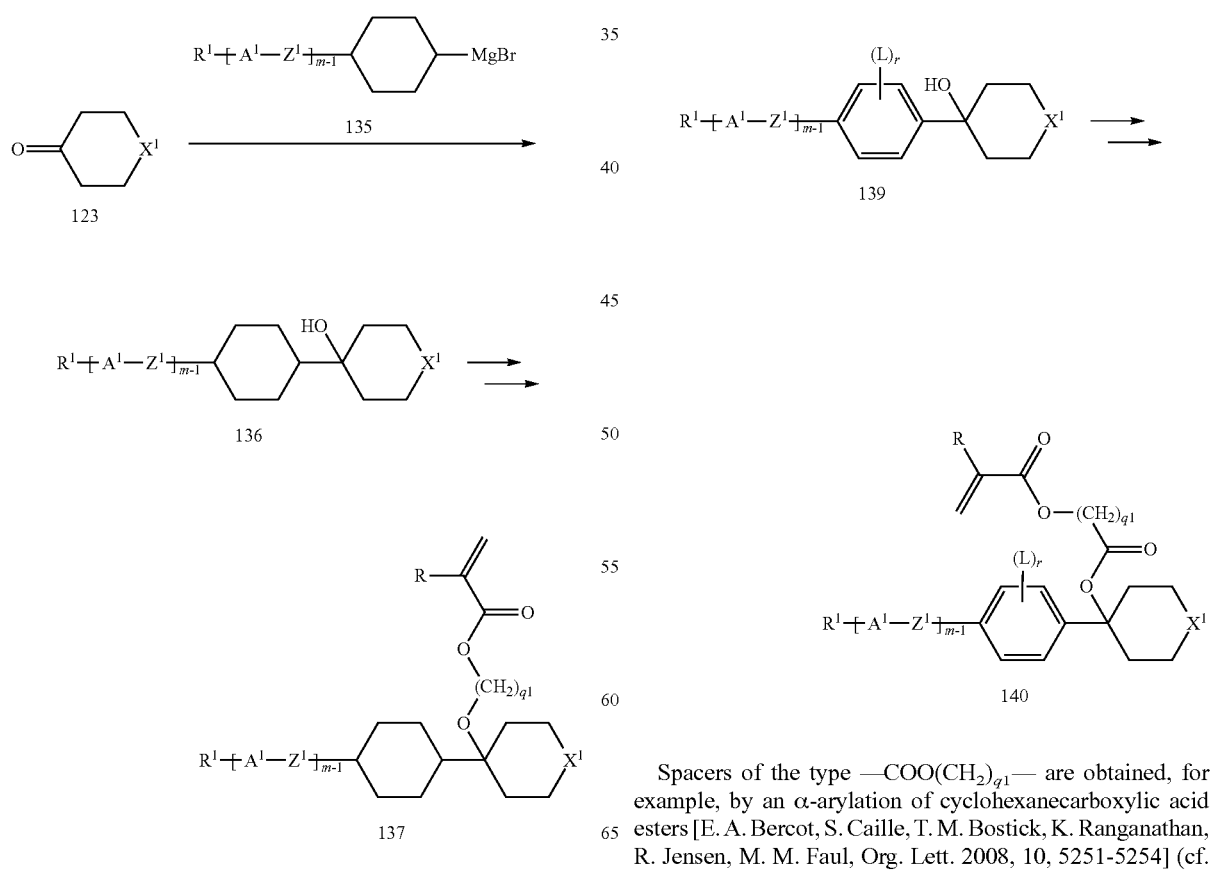

Spacers of the type —COO(CH$_2$)$_{q1}$— are obtained, for example, by an α-arylation of cyclohexanecarboxylic acid esters [E. A. Bercot, S. Caille, T. M. Bostick, K. Ranganathan, R. Jensen, M. M. Faul, Org. Lett. 2008, 10, 5251-5254] (cf. Scheme 34).

Scheme 34: α-Arylation of cyclohexanecarboxylic acids 141. Synthesis of the compounds 144. In this pictorial formula, $W^1 = R$. R is preferably H or $CH_3$.

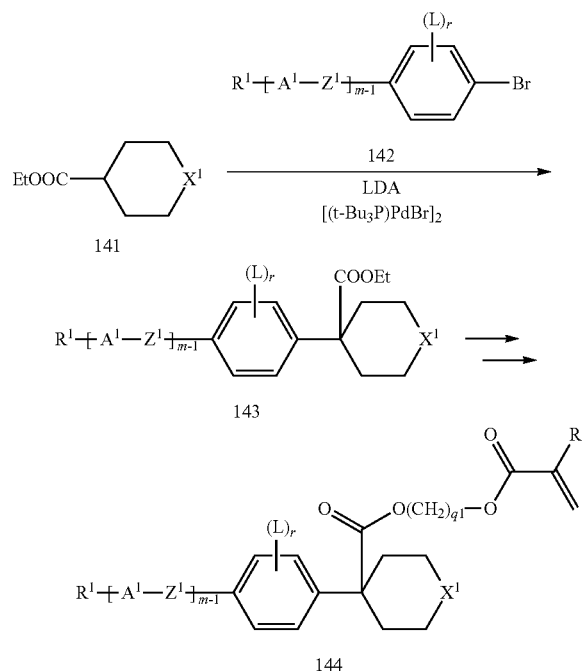

The invention thus generally furthermore relates to a process for the preparation of compounds of the formula I which is characterised in that the radicals -Sp-P or —P or parts thereof are linked to a suitable precursor. An acrylic acid derivative is preferably linked to the suitable precursor. The suitable compound here is generally an alcohol or a polyol, depending on the number of polymerisable groups. The linking preferably comprises the formation of an ester or ether. Details on these reactions can easily be obtained from the above synthesis strategies.

The invention furthermore relates to the use of the compounds of the formula I in liquid-crystalline media, in particular the use as polymerisable component and/or for a polymer in such media. The compounds are also used for the stabilisation of liquid-crystalline phases, in particular blue phases. The stabilisation is carried out by polymerisation in the mixture.

This type of use is known for other polymerisable compounds and is described specifically for the case of blue phases in the literature cited and in the example part. In general, the medium is polymerised at a temperature at which it is in the blue phase. The stability range of this phase is thus broadened. The compounds and media according to the invention are associated with a considerable improvement in the hitherto achievable properties of the polymer-stabilised media in the blue phase.

Preferred liquid-crystalline media are characterised in that they have, after stabilisation of the blue phase by polymerisation, a blue phase at least in the range from 15 to 30° C., preferably from 10 to 40° C., particularly preferably from 0 to 50° C. and very particularly preferably from −10 to 60° C.

The present invention likewise relates to liquid-crystalline media which comprise at least one unpolymerised monomer of the formula I or comprise a polymerisation product thereof, i.e. a polymer comprising at least one monomer component of the formula I, or both. Besides the compounds of the formula I, the media according to the invention preferably comprise one or more further compounds which are liquid-crystalline or mesogenic. Mesogenic in this connection means, analogously to C. Tschierske et al. in *Angew. Chem.* 2004, 116, 6340-86 or M. Barón *Pure Appl. Chem.* 2001, 73, 845-895, that the compound in suitable concentrations and at suitable temperatures contributes to the formation of the desired mesophase. In addition, further mesogenic or non-mesogenic monomers containing one or two reactive groups, chiral dopants, stabilisers, assistants or nanoparticles may be present in the media.

Particularly preferred media according to the invention are indicated below:

The medium comprises one or more monoreactive monomers or a polymer which is built up from one or more monoreactive monomers and optionally further monomers. The proportion of monoreactive monomers is preferably 1 to 15%, particularly preferably 2 to 12%.

Besides the monoreactive monomers mentioned above, the medium comprises one or more compounds which act as crosslinking agents, which are distinguished by two or more reactive groups. These may also include the compounds of the formula I.

The medium comprises one or more direactive monomers or a polymer which is built up from one or more direactive monomers and optionally further monomers. The proportion of direactive monomers is preferably 0 to 9%, particularly preferably 0 to 6%. In a preferred embodiment, all or some of the direactive monomers belong to the compounds of the formula I according to the invention containing 2 or more reactive groups.

The sum of mono- and direactive monomers is preferably 3 to 17%, particularly preferably 6-14%.

Trireactive or polyreactive (>3) monomers can also be employed. The trireactive or polyreactive (>3) monomers preferably belong in some or all cases to the compounds of the formula I.

The ratio of monoreactive monomers to crosslinking agents is preferably between 3:1 and 1:1. The ratio is dependent on the number of reactive groups of the crosslinking agents involved. In the case of the use of tetrareactive crosslinking agents, it is particularly preferably between 3:1 and 2:1, and in the case of the use of direactive crosslinking agents, it is particularly preferably between 1.5:1 and 1:1.

Monoreactive monomers which differ from compounds of the formula I have, for example, a structure of the formula $R^a$-Sp-P,
in which
P denotes a polymerisable group (cf. above for formula I),
Sp denotes a spacer group or a single bond (cf. above), and
$R^a$ denotes an organic radical having at least 3 C atoms.

The radical $R^a$ can be a so-called mesogenic radical, which generally contains one or more rings, or a simple, generally chain-shaped, non-mesogenic radical.

Non-mesogenic radicals are preferably straight-chain or branched alkyl having 1 to 30 C atoms, in which, in addition, one or more non-adjacent $CH_2$ groups may each be replaced, independently of one another, by —C($R^0$)=C($R^{00}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN.

Preferred meanings of P and Sp correspond to the meanings indicated below for formula I*.

Preferred mesogenic monomers containing one, two or more polymerisable groups which differ from compounds of the formula I are characterised by the formula I*

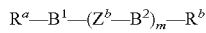  I* in which the individual radicals have the following meanings:
$R^a$ and $R^b$ each, independently of one another, denote P, P-Sp-, H, halogen, $SF_5$, $NO_2$, a carbon group or a hydrocarbon group, where at least one of the radicals $R^a$ and $R^b$ denotes or contains a group P or P-Sp-,
P on each occurrence, identically or differently, denotes a polymerisable group (cf. above for formula I),
Sp on each occurrence, identically or differently, denotes a spacer group or a single bond (cf. above),
$B^1$ and $B^2$ each, independently of one another, denote an aromatic, heteroaromatic, alicyclic or heterocyclic group, preferably having 4 to 25 ring atoms, which may also contain fused rings, and which may also be mono- or polysubstituted by L,
L denotes H, OH, $CH_2OH$, halogen, $SF_5$, $NO_2$, a carbon group or a hydrocarbon group,
$Z^b$ on each occurrence, identically or differently, denotes —O—, —S—, —CO—, —CO—O—, —COO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —C≡C—, —CH=CH—OCO—, —OCO—CH=CH—, $CR^0R^{00}$ or a single bond,
$R^0$ and $R^{00}$ each, independently of one another, denote H or alkyl having 1 to 12 C atoms,
m denotes 0, 1, 2, 3 or 4,
n1 denotes 1, 2, 3 or 4.

Particularly preferred compounds of the formula I* are those in which
$R^a$ and $R^b$ each, independently of one another, denote P, P-Sp-, H, F, Cl, Br, I, —CN, —NO$_2$, —NCO, —NCS, —OCN, —SCN, $SF_5$ or straight-chain or branched alkyl having 1 to 25 C atoms, in which, in addition, one or more non-adjacent CH$_2$ groups may each be replaced, independently of one another, by —C($R^0$)=C($R^{00}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN, P or P-Sp-, where at least one of the radicals $R^a$ and $R^b$ denotes or contains a group P or P-Sp-,
$B^1$ and $B^2$ each, independently of one another, denote 1,4-phenylene, naphthalene-1,4-diyl, naphthalene-2,6-diyl, phenanthrene-2,7-diyl, anthracene-2,7-diyl, fluorene-2,7-diyl, coumarine, flavone, where, in addition, one or more CH groups in these groups may be replaced by N, cyclohexane-1,4-diyl, in which, in addition, one or more non-adjacent CH$_2$ groups may be replaced by O and/or S, 1,4-cyclohexenylene, bicyclo[1.1.1]-pentane-1,3-diyl, bicyclo[2.2.2]octane-1,4-diyl, spiro[3.3]heptane-2,6-diyl, piperidine-1,4-diyl, decahydronaphthalene-2,6-diyl, 1,2,3,4-tetrahydronaphthalene-2,6-diyl, indane-2,5-diyl or octahydro-4,7-methanoindane-2,5-diyl, where all these groups may be unsubstituted or mono- or polysubstituted by L,
L denotes OH, CH$_2$OH, F, Cl, Br, I, —CN, —NO$_2$, —NCO, —NCS, —OCN, —SCN, —C(=O)N($R^x$)$_2$, —C(=O)Y$^1$, —C(=O)$R^x$, —N($R^x$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F, Cl, P or P-Sp-,
P and Sp have the meanings indicated above,
$Y^1$ denotes halogen,
$R^x$ denotes P, P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P or P-Sp-, an optionally substituted aryl or aryloxy group having 6 to 40 C atoms, or an optionally substituted heteroaryl or heteroaryloxy group having 2 to 40 C atoms.

The term "carbon group" denotes a mono- or polyvalent organic group containing at least one carbon atom, where this either contains no further atoms (such as, for example, —C≡C—) or optionally contains one or more further atoms, such as, for example, N, O, S, P, Si, Se, As, Te or Ge (for example carbonyl, etc.). The term "hydrocarbon group" denotes a carbon group which additionally contains one or more H atoms and optionally one or more heteroatoms, such as, for example, N, O, S, P, Si, Se, As, Te or Ge.

"Halogen" denotes F, Cl, Br or I, preferably F or Cl.

A carbon or hydrocarbon group can be a saturated or unsaturated group. Unsaturated groups are, for example, aryl, alkenyl or alkynyl groups. A carbon or hydrocarbon group having more than 3 C atoms may be straight-chain, branched and/or cyclic and may also contain spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" in accordance with the above definition, containing one or more heteroatoms.

Preferred carbon and hydrocarbon groups are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl and aryloxy having 6 to 40, preferably 6 to 25, C atoms, and optionally substituted alkylaryl, arylalkyl, alkylaryloxy, arylalkyloxy, arylcarbonyl, aryloxycarbonyl, arylcarbonyloxy and aryloxycarbonyloxy having 6 to 40, preferably 6 to 25, C atoms.

Further preferred carbon and hydrocarbon groups are $C_1$-$C_{40}$ alkyl, $C_2$-$C_{40}$ alkenyl, $C_2$-$C_{40}$ alkynyl, $C_3$-$C_{40}$ alkyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_2$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ allyl, $C_4$-$C_{22}$ alkyldienyl, $C_6$-$C_{12}$ aryl, $C_6$-$C_{20}$ arylalkyl and $C_2$-$C_{20}$ heteroaryl.

Further preferred carbon and hydrocarbon groups are straight-chain, branched or cyclic alkyl radicals having 1 to 40, preferably 1 to 25, C atoms, which are unsubstituted or mono- or polysubstituted by F, Cl, Br, I or CN, and in which one or more non-adjacent CH$_2$ groups may each be replaced, independently of one another, by —C($R^x$)=C($R^x$)—, —C≡C—, —N($R^x$)—, —O—, —S—, —CO—, —CO—O—, —O—CO—, —O—CO—O— in such a way that O and/or S atoms are not linked directly to one another.

$R^x$ preferably denotes H, halogen, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O— and in which one or more H atoms may be replaced by fluorine, an optionally substituted aryl or aryloxy group having 6 to 40 C atoms, or an optionally substituted heteroaryl or heteroaryloxy group having 2 to 40 C atoms.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, ndecoxy, n-undecoxy, n-dodecoxy, etc.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, ndecoxy, n-undecoxy, n-dodecoxy, etc.

Preferred amino groups are, for example, dimethylamino, methylamino, methylphenylamino, phenylamino, etc.

Aryl and heteroaryl groups can be monocyclic or polycyclic, i.e. they may contain one ring (such as, for example, phenyl) or two or more rings, which may also be fused (such as, for example, naphthyl) or covalently linked (such as, for example, biphenyl), or contain a combination of fused and linked rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 2 to 25 C atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1"]-terphenyl-2'-yl, naphthyl, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]-thiophene, thieno[3,2b]thiophene, dithienothiophene, isobenzothiophene, dibenzothiophene, benzothiadiazothiophene, or combinations of these groups. The heteroaryl groups may also be substituted by alkyl, alkoxy, thioalkyl, fluorine, fluoroalkyl or further aryl or heteroaryl groups.

The (non-aromatic) alicyclic and heterocyclic groups include both saturated rings, i.e. those which contain exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 3 to 25 C atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, tert-butyl or optionally substituted aryl groups.

Preferred substituents, also referred to as "L" above and below, are, for example, F, Cl, Br, I, —CN, —$NO_2$, —NCO, —NCS, —OCN, —SCN, —C(=O)N($R^x$)$_2$, —C(=O)$Y^1$, —C(=O)$R^x$, —N($R^x$)$_2$, in which $R^x$ has the meaning indicated above and $Y^1$ denotes halogen, optionally substituted silyl or aryl having 6 to 40, preferably 6 to 20, C atoms, and straight-chain or branched alkyl, alkoxy, alkylcarbonyl, alkoxycarbonyl, alkylcarbonyloxy or alkoxycarbonyloxy having 1 to 25 C atoms, in which one or more H atoms may optionally be replaced by F or Cl.

"Substituted silyl or aryl" means preferably substituted by halogen, —CN, $R^0$, —$OR^0$, —CO—$R^0$, —CO—O—$R^0$, —O—CO—$R^0$ or —O—CO—O—$R^0$, in which $R^0$ has the meaning indicated above.

Particularly preferred substituents L are, for example, F, Cl, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, furthermore phenyl.

is preferably

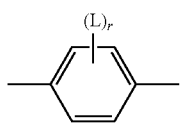

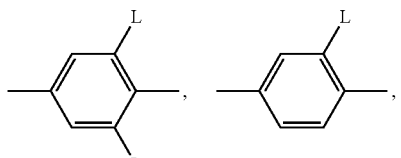

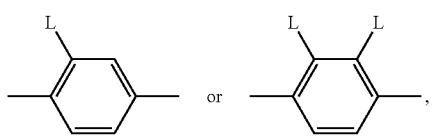

in which L has one of the meanings indicated above.

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or C≡C triple bond, and groups which are suitable for polymerisation with ring opening, such as, for example, oxetane or epoxide groups.

Preferred groups P are defined as for formula I above.

Preferred spacer groups Sp are selected from the formula Sp'-X—, as defined above for formula I.

The polymerisable compounds and RMs can be prepared analogously to the process known to the person skilled in the art and described in standard works of organic chemistry, such as, for example, in Houben-Weyl, Methoden der organischen Chemie [Methods of Organic Chemistry], Thieme-Verlag, Stuttgart. Further synthetic methods are given in the documents cited above and below. In the simplest case, RMs of this type are synthesised, for example, by esterification or etherification of 2,6-dihydroxynaphthalene or 4,4'-dihydroxybiphenyl using corresponding acids, acid derivatives or halogenated compounds containing a group P, such as, for example, (meth)acryloyl chloride or (meth)acrylic acid, in the presence of a dehydrating reagent, such as, for example, DCC (dicyclohexylcarbodiimide).

As a further component, the liquid-crystalline media preferably comprise non-polymerisable compounds which support the liquid-crystalline phase, which taken together are also known as host mixture. This proportion is typically 50 to 95% by weight, preferably 80 to 90% by weight. In the case of polymer-stabilised blue phases, the non-polymerisable fraction preferably comprises compounds selected from Table A (see example part). The fraction preferably consists of 50% by weight or more of these compounds, very particularly preferably 80% by weight or more.

The LC media which can be used in accordance with the invention are prepared in a manner customary per se, for example by mixing one or more of the above-mentioned compounds with one or more polymerisable compounds as defined above and optionally with further liquid-crystalline compounds and/or additives. In general, the desired amount of the components used in smaller amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes.

The present invention furthermore relates to the use of the media according to the invention in an electro-optical device, preferably a liquid-crystal display, and to devices of this type. The displays operate with a polymer-stabilised liquid-crystal phase, which preferably works in the region of the blue phase or is nematic. The device is preferably produced by carrying out the polymerisation of the polymerisable constituents of the medium in the device itself, i.e. in the opto-electronic cell.

The invention furthermore relates to the use of polymerisable compounds according to the invention, and to the use of LC media according to the invention, in PSA displays (frequently also called PS-VA displays), in particular to the use in PSA displays containing an LC medium, for the generation of a tilt angle in the LC medium by in situ polymerisation of the polymerisable compounds and media according to the invention in the PSA display, preferably with application of an electrical or magnetic field.

For PSA applications, the compounds according to the invention are preferably combined with the following reactive mesogens as polymerisable compounds which can easily be polymerised with little or no initiator under UV light of a suitable wavelength:

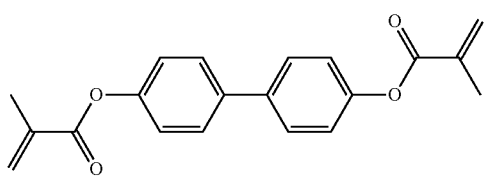

RM-1

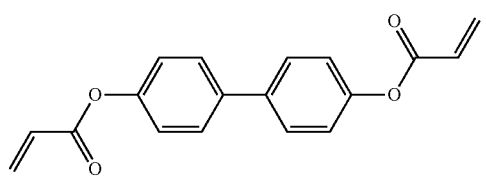

RM-2

-continued
RM-3
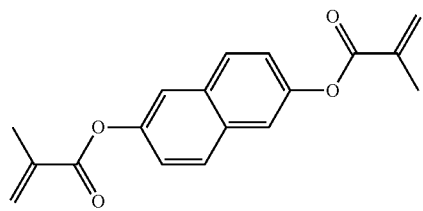
RM-4
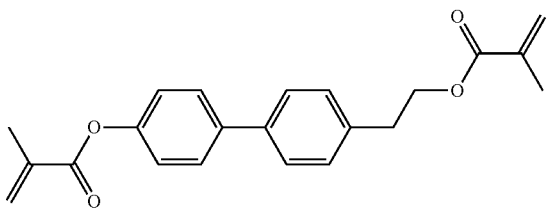
RM-5
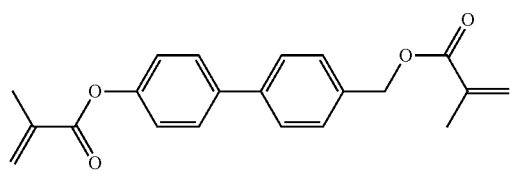
RM-6
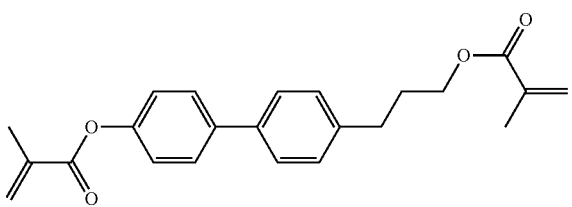
RM-7
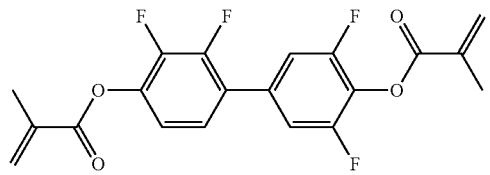
RM-8
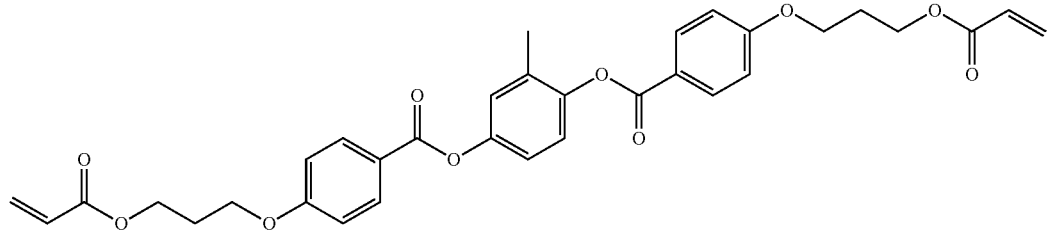
RM-9
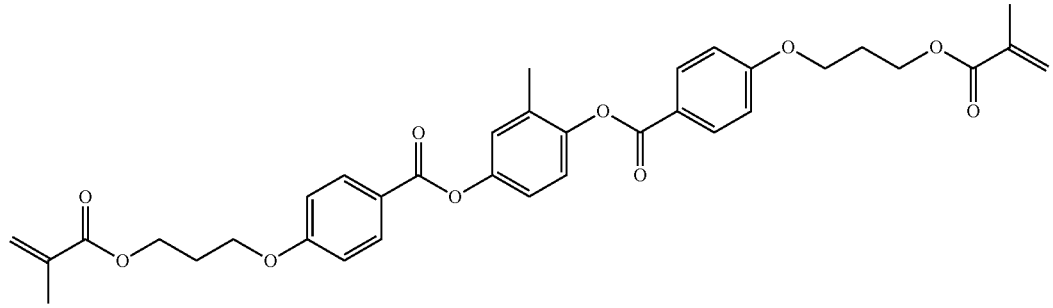
RM-10
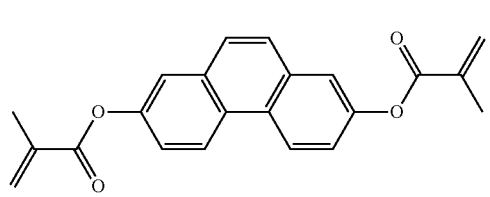
RM-11
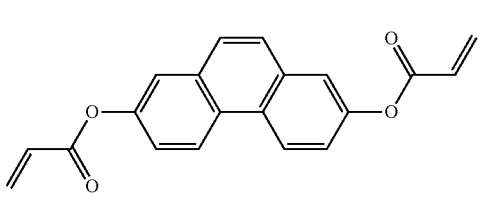
RM-12
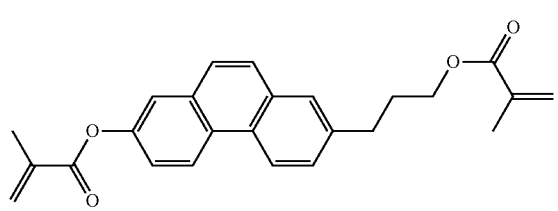
RM-13
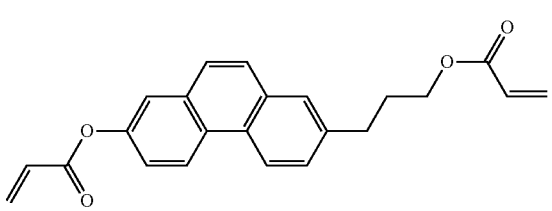

-continued

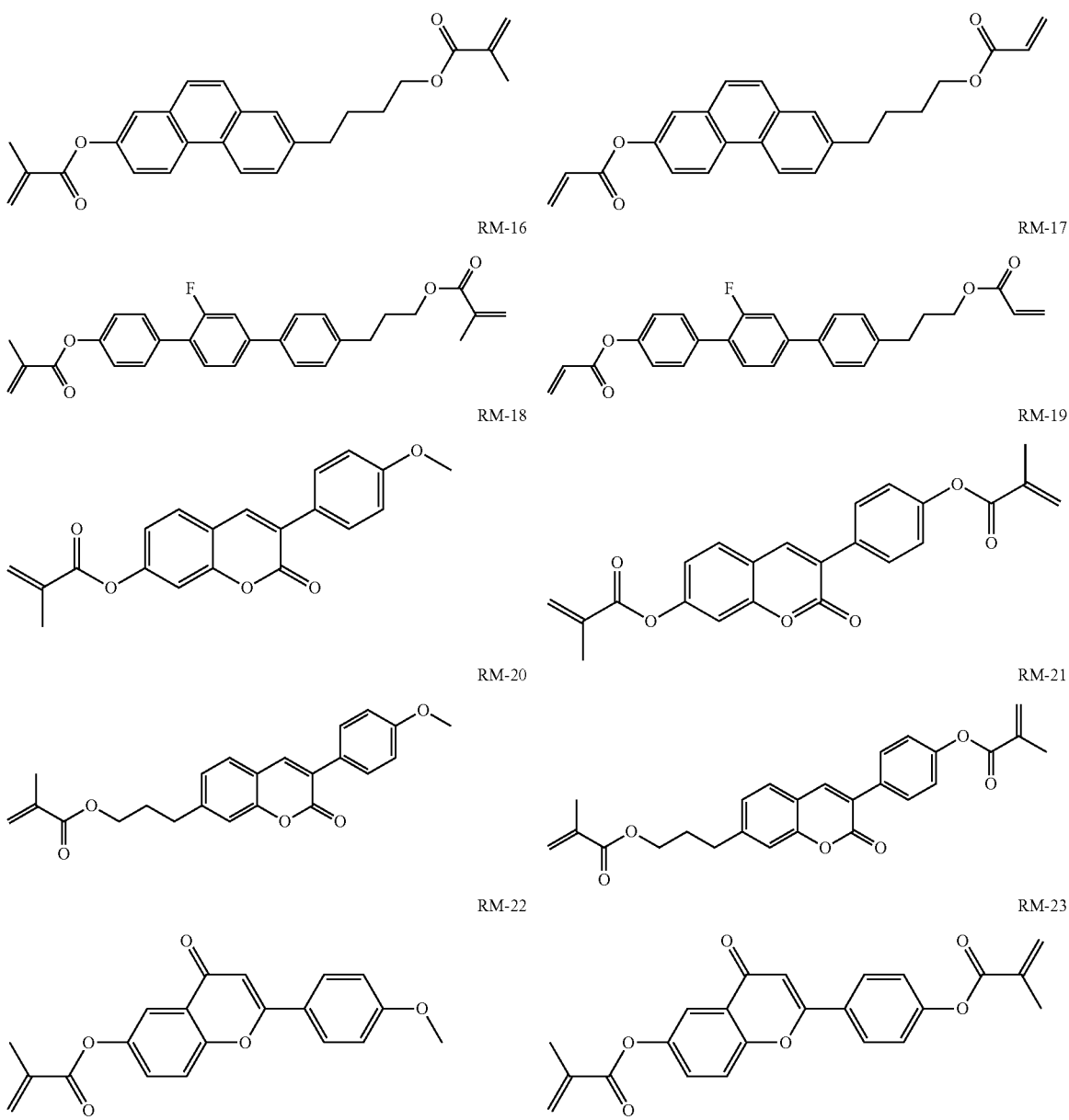

For the purposes of the present invention, the terms alkyl, alkenyl, etc., are defined as follows:

The term "alkyl" encompasses straight-chain and branched alkyl groups having 1-9 carbon atoms, in particular the straight-chain groups methyl, ethyl, propyl, butyl, pentyl, hexyl and heptyl. Groups having 2-5 carbon atoms are generally preferred.

The term "alkenyl" encompasses straight-chain and branched alkenyl groups having up to 9 carbon atoms, in particular the straight-chain groups. Particularly preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" in this application encompasses straight-chain groups containing at least one fluorine atom, preferably a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "halogenated alkyl radical" preferably encompasses mono- or polyfluorinated and/or -chlorinated radicals. Perhalogenated radicals are included. Particular preference is given to fluorinated alkyl radicals, in particular $CF_3$, $CH_2CF_3$, $CH_2CHF_2$, $CHF_2$, $CH_2F$, $CHFCF_3$ and $CF_2CHFCF_3$.

The term "alkylene" encompasses straight-chain and branched alkanediyl groups having 1-12 carbon atoms, in particular the straight-chain groups methylene, ethylene, propylene, butylene and pentylene. Groups having 2-8 carbon atoms are generally preferred.

Above and below, a 1,4-substituted cyclohexane ring, depicted in the formulae, with horizontal (=preferably equatorial) and vertical (=preferably axial) substituents preferably has the following configuration of the substituents:

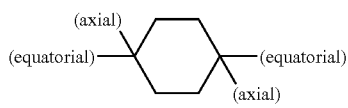

Some of the substituents drawn here can also denote H.

Further combinations of the embodiments and variants of the invention in accordance with the description also arise from the claims.

In the present application, the term compounds, unless expressly indicated otherwise, means both one compound and also a plurality of compounds.

The following examples are intended to explain the invention without limiting it. The person skilled in the art will be able to take procedure details from the examples which are not mentioned specifically in the general description, generalise these details in accordance with general expert knowledge and apply them to his specific problem.

EXAMPLES

Example 1

2-{4-[2-(2-Methylacryloyloxy)ethyl]-4'-propylbicyclohexyl-4-yl}-ethyl 2-methacrylate The compound 2-{4-[2-(2-methylacryloyloxy)ethyl]-4'-propylbicyclohexyl-4-yl}ethyl 2-methacrylate according to the invention is synthesised as described below.

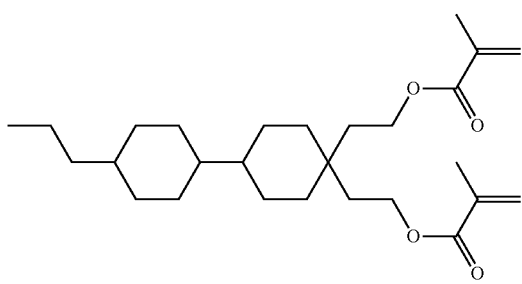 [SMILES: C=C(C)C(=O)OCCC1(CCOC(=O)C(=C)C)CCC(C2CCC(CCC)CC2)CC1]

1.1 Preparation of 2,4-dioxo-9-(4-propylcyclohexyl)-3-azaspiro[5.5]-undecane-1,5-dicarbonitrile

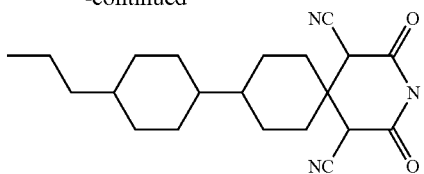

190.0 g (0.85 mol) of 4'-propylbicyclohexyl-4-one are initially introduced at 0° C. in 1000 ml (7.0 mol) of methanolic ammonia solution (7 M), and 273.5 ml (2.6 mol) of ethyl cyanoacetate are added dropwise. The mixture is left at 5° C. for 3 d, and the resultant precipitate is filtered off with suction. The filter residue is digested in diethyl ether and again filtered off with suction. The ammonium salt obtained in this way is suspended in 3 l of water, and the mixture is carefully rendered acidic using conc. HCl. The precipitate is filtered off and washed with cold water. The residue is recrystallised from ethanol, giving 2,4-dioxo-9-(4-propylcyclohexyl)-3-aza-spiro[5.5]-undecane-1,5-dicarbonitrile as a colourless solid.

1.2 Preparation of (4-carboxymethyl-4'-propylbicyclohexyl-4-yl)acetic acid

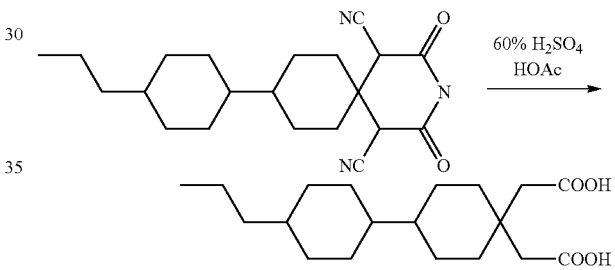

A mixture of 50 g (0.14 mol) of 2,4-dioxo-9-(4-propylcyclohexyl)-3-aza-spiro[5.5]undecane-1,5-dicarbonitrile, 800 ml of glacial acetic acid and 1.5 l of 60% sulfuric acid is stirred at 120-125° C. for 5 days. After cooling, the batch is added to ice-water and extracted a number of times with THF/MTBE (1:1). The combined organic phases are washed with saturated sodium chloride solution and dried using sodium sulfate. The solution is concentrated to dryness, and the residue is recrystallised from acetonitrile/THF (2:1), giving (4-carboxymethyl-4'-propylbicyclohexyl-4-yl)acetic acid as a beige solid.

1.3 Preparation of 2-[4-(2-hydroxyethyl)-4'-propylbicyclohexyl)-4-yl]ethanol

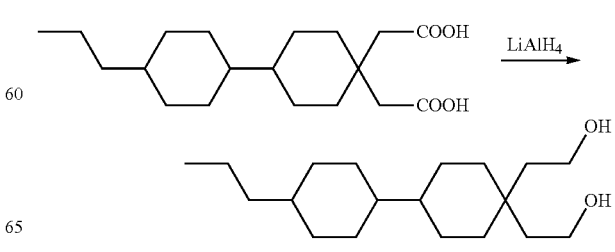

10.0 g (0.26 mol) of lithium aluminium hydride are suspended in 200 ml of THF, and a solution of 24.0 g (74.0 mmol) of (4-carboxymethyl-4'-propylbicyclohexyl-4-yl)acetic acid in 300 ml of THF is metered in. When the addition is complete, the mixture is stirred at RT for 1 h and at the reflux temperature for 3 h. The reaction mixture is hydrolysed using water and neutralised using dil. hydrochloric acid. The salts are filtered off, and the filtrate is diluted with MTBE. The solution is washed with saturated sodium chloride solution and dried using sodium sulfate. The solid remaining after removal of the solvents is recrystallised from acetonitrile, giving 2-[4-(2-hydroxyethyl)-4'-propylbicyclohexyl-4-yl]ethanol as a beige solid.

1.4 Preparation of 2-{4-[2-(2-methylacryloyloxy)ethyl]-4'-propylbicyclohexyl-4-yl}ethyl 2-methacrylate

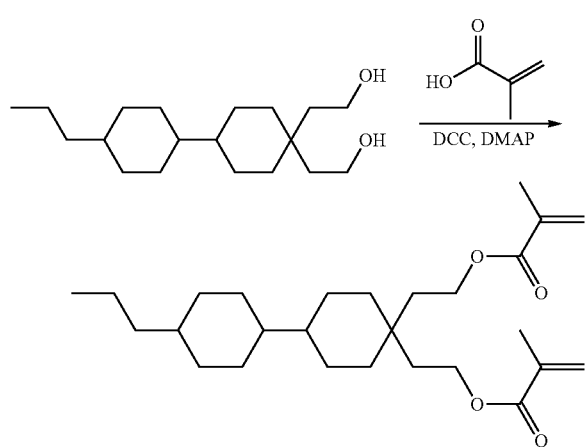

18.0 g (60.7 mmol) of 2-[4-(2-hydroxyethyl)-4'-propylbicyclohexyl-4-yl]ethanol are initially introduced together with 11.6 ml (0.14 mol) of methacrylic acid and 222 mg (1.82 mmol) of DMAP in 160 ml of THF. A solution of 28.0 g (0.14 mol) of DCC in 40 ml of THF is metered in, and the batch is stirred for 18 h. 4.0 g (31.7 mmol) of oxalic acid dihydrate are added, and the mixture is filtered. The filtrate is concentrated to dryness, and the residue is purified by column chromatography (SiO$_2$, dichloromethane). Further purification is carried out by recrystallisation from isopropanol, giving 2-{4-[2-(2-methylacryloyloxy)ethyl]-4'-propylbicyclohexyl-4-yl}ethyl 2-methacrylate as a colourless solid having a melting point of 37° C.

Phase sequence: Tg −57 C 37 I
$^1$H-NMR (300 MHz, CHCl$_3$): δ=6.09-6.06 (m, 2H, CMe=CH$_2$), 5.55-5.51 (m, 2H, CMe=CH$_2$), 4.26-4.16 (m, 4H, (O)COCH$_2$), 1.94-1.92 (m, 6H, CMe=CH$_2$), 1.80-1.48 (m, 12H, H$_{aliphat.}$), 1.36-1.08 (m, 9H, H$_{aliphat.}$), 1.06-0.76 (m, 9H, H$_{aliphat.}$).
MS (EI): m/e (%)=432 (8, M$^+$), 346 (12, [M−methacrylic acid]$^+$), 260 (62, [M−2× methacrylic acid]$^+$), 232 (100).

Example 2

6-(2-{4-[6-(2-Methylacryloyloxy)hexyloxycarbonylmethyl]-4'-propylbicyclohexyl-4-yl}acetoxy)hexyl 2-methacrylate The compound 6-(2-{4-[6-(2-methylacryloyloxy)hexyloxycarbonylmethyl]-4'-propylbicyclohexyl-4-yl}acetoxy)hexyl 2-methacrylate according to the invention is synthesised as described below.

2.1 Preparation of 6-bromohexyl [4-(6-bromohexyloxycarbonylmethyl)-4'-propylbicyclohexyl-4-yl]acetate

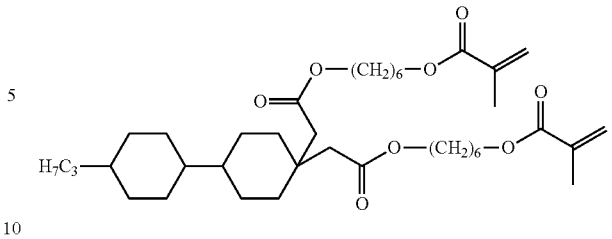

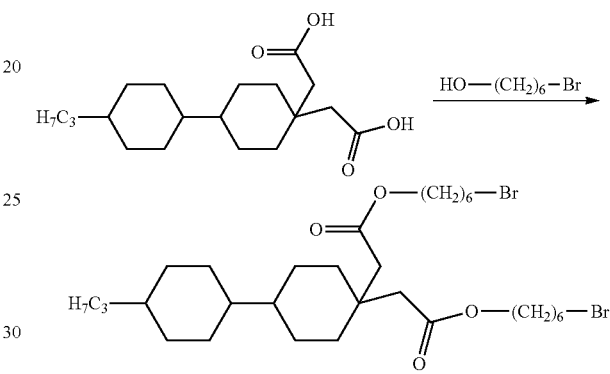

10.0 g (30.8 mmol) of (4-carboxymethyl-4'-propylbicyclohexyl-4-yl)acetic acid are heated on a water separator for 6 h together with 15.0 g (80.4 mmol) of 6-bromo-1-hexanol and 0.50 g (2.90 mmol) of paratoluenesulfonic acid monohydrate in 150 ml of toluene. After cooling, the reaction mixture is subjected to absorptive filtration (SiO$_2$, toluene), and the filtrate is concentrated to dryness. The crude product obtained in this way is used directly for the next reaction.

2.2 Preparation of 6-(2-{4-[6-(2-methylacryloyloxy)hexyloxycarbonylmethyl]-4'-propylbicyclohexyl-4-yl}acetoxy)hexyl 2-methacrylate

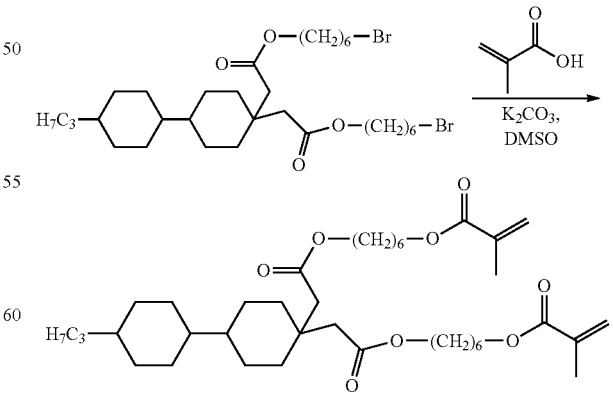

10.0 g of crude (about 15.4 mmol) 6-bromohexyl [4-(6-bromohexyloxycarbonylmethyl)-4'-propylbicyclohexyl-4-yl]acetate are stirred at 50° C. and with exclusion of light for 19 h together with 7.8 ml (92.7 mmol) of methacrylic acid and 14.9 g (0.11 mol) of potassium carbonate in 100 ml of DMSO. The suspension is diluted with MTBE and stirred into water. The organic phase is separated off, and the aqueous phase is extracted with MTBE. The combined organic phases are washed with sat. sodium chloride solution. The solution is dried using sodium sulfate and concentrated to dryness. The crude product is purified by column chromatography (SiO$_2$, dichloromethane), giving 6-(2-{4-[6-(2-methylacryloyloxy)hexyloxycarbonylmethyl]-4'-propylbicyclohexyl-4-yl}acetoxy)hexyl 2-methacrylate as a colourless oil.

Phase sequence: Tg −69 I $^1$H-NMR (300 MHz, CHCl$_3$): δ=6.09-6.06 (m, 2H, CMe=CH$_2$), 5.55-5.51 (m, 2H, CMe=CH$_2$), 4.14 (t, 4H, J=6.5 Hz, 2×OCH$_2$), 4.08-4.01 (m, 4H, J=6.5 Hz, J=2.6 Hz, 2×OCH$_2$), 2.56 (s, 2H, —CH$_2$C(O)O—), 2.44 (s, 2H, —CH$_2$C(O)O—), 1.94 (s(broad), 6H, CMe=CH$_2$), 1.81-1.51 (m, 16H, H$_{aliphat.}$), 1.46-1.08 (m, 17H, H$_{aliphat.}$), 1.06-0.76 (m, 9H, H$_{aliphat.}$).

MS (EI): m/e (%)=660 (4, M$^+$), 475 (13), 433 (50), 247 (98), 69 (100).

Example 3

6-(2-{4-[6-(2-Methylacryloyloxy)hexyloxycarbonylmethyl]-4'-propylbicyclohexyl-4-yl}acetoxy)hexyl acrylate The compound 6-(2-{4-[6-(2-methylacryloyloxy)hexyloxycarbonylmethyl]-4'-propylbicyclohexyl-4-yl}acetoxy)hexyl acrylate according to the invention is synthesised analogously to Example 2.

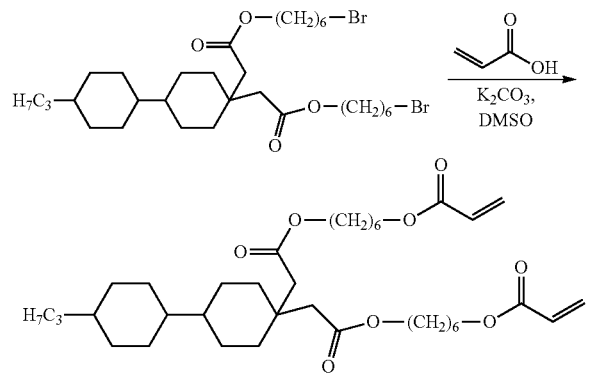

Phase sequence: Tg −72 I $^1$H-NMR (400 MHz, CHCl$_3$): δ=6.40 (dd, 2H, J=17.4 Hz, J=1.5 Hz, H$_{acrylate}$), 6.12 (dd, 2H, J=17.4 Hz, J=10.9 Hz, H$_{acrylate}$), 5.81 (ddd, 2H, J=10.9 Hz, J=1.6 Hz, H$_{acrylate}$), 4.15 (t, 4H, J=6.5 Hz, 2×OCH$_2$), 4.07-4.04 (m, 4H, 2×OCH$_2$), 2.56 (s, 2H, —CH$_2$C(O)O—), 2.44 (s, 2H, CH$_2$C(O)O—), 1.81-1.53 (m, 16H, H$_{aliphat.}$), 1.45-1.36 (m, 8H, H$_{aliphat.}$), 1.33-1.11 (m, 9H, H$_{aliphat.}$), 1.06-0.76 (m, 9H, H$_{aliphat.}$).

MS (EI): m/e (%)=632 (2, M$^+$), 461 (13), 419 (52), 247 (100), 83 (62), 55 (83).

Example 4

2-{4-[2-(2-Methylacryloyloxy)ethyl]-4'-propylbicyclohexyl-4-yl}-ethyl 2-acrylate The compound 2-{4-[2-(2-methylacryloyloxy)ethyl]-4'-propylbicyclohexyl-4-yl}ethyl 2-acrylate according to the invention is synthesised analogously to Example 1.

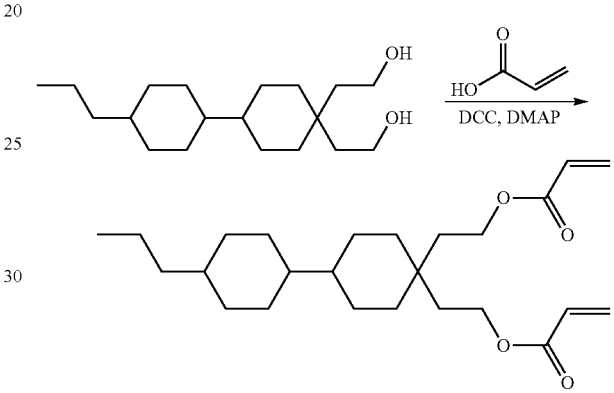

Phase sequence: Tg −63 C 34 I $^1$H-NMR (300 MHz, CHCl$_3$): δ=6.38 (ddd, 2H, J=17.3 Hz, J=2.9 Hz, J=1.6 Hz, H$_{acrylate}$), 6.12 (ddd, 2H, J=17.3 Hz, J=10.9 Hz, J=2.9 Hz, H$_{acrylate}$), 5.81 (ddd, 2H, J=10.9 Hz, J=2.9 Hz, J=1.6 Hz, H$_{acrylate}$), 4.27-4.17 (m, 4H, (O)COCH$_2$), 1.80-1.48 (m, 12H, H$_{aliphat.}$), 1.36-1.08 (m, 9H, H$_{acrylate}$), 1.06-0.76 (m, 9H, H$_{aliphat.}$).

MS (EI): m/e (%)=404 (2, M$^+$), 332 (9, [M−acrylic acid]$^+$), 260 (32, [M−2× acrylic acid]$^+$), 232 (93), 55 (100).

Use Examples

The following acronyms are used to describe the components of the liquid-crystalline base mixture (host). The index n adopts a value from 1 to 9.

TABLE A

Acronyms for LC components

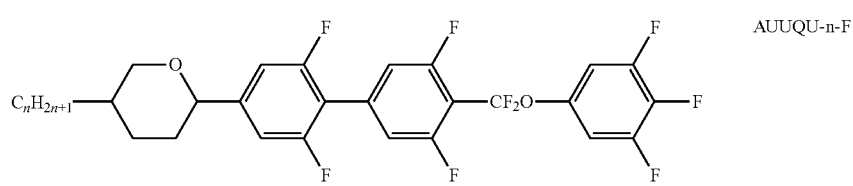

AUUQU-n-F

TABLE A-continued

Acronyms for LC components

| Structure | Acronym |
|---|---|
| (tetrahydropyran-phenyl-phenyl-CF$_2$O-phenyl-CF$_3$, fluorinated) | AUUQU-n-T |
| (tetrahydropyran-phenyl-phenyl-CF$_2$O-phenyl-OCF$_3$, fluorinated) | AUUQU-n-OT |
| (tetrahydropyran-phenyl-phenyl-CF$_2$O-phenyl-F, fluorinated) | AGUQU-n-F |
| (phenyl-phenyl-CF$_2$O-phenyl-F, fluorinated) | PUQU-n-F |
| (phenyl-phenyl-COO-phenyl-F, fluorinated) | PUZU-n-F |

The following monomers are used:

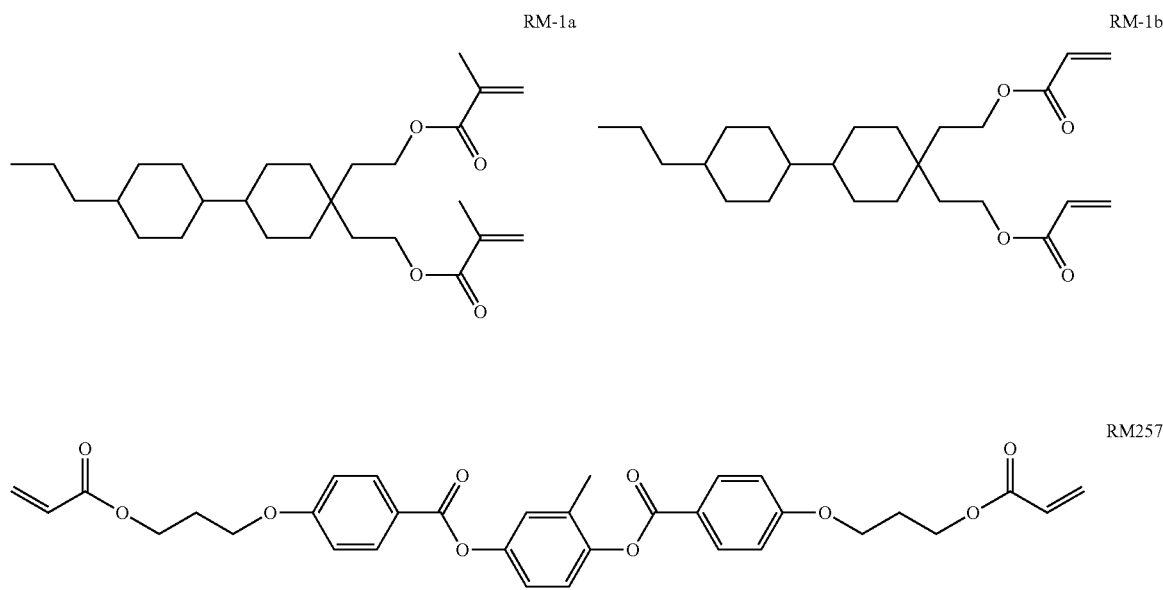

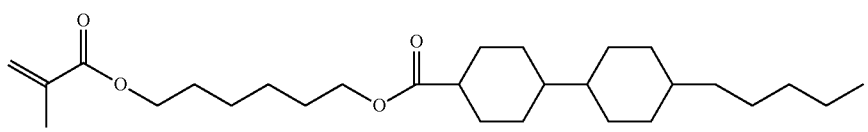
RM-2

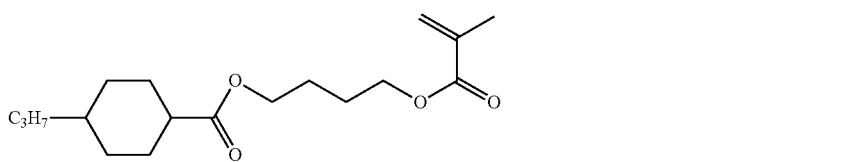
RM-3

RM220 has the phase sequence C 82.5 N 97 I.
RM257 has the phase sequence C 66 N 127 I.
The following additives are used
(DP: chiral dopant, IN: polymerisation initiator)

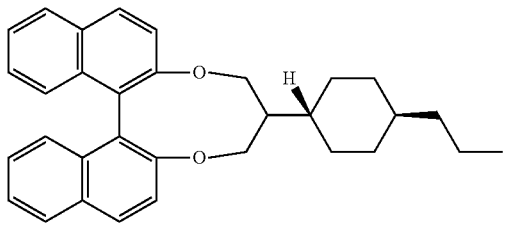
DP-1

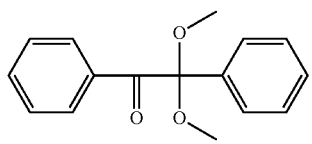
IN-1
(Ciba® Irgacure® 651)

Further chiral dopants and polymerisation initiators for LC mixtures are known to the person skilled in the art are expressly mentioned here.

TABLE

Composition of the base mixture (host) H1 before addition of the polymerisation components:

| Composition | |
| --- | --- |
| Component Acronym | Proportion % by wt. |
| PUQU-3-F | 5.00 |
| AGUQU-3-F | 13.00 |
| AUUQU-2-F | 6.00 |
| AUUQU-3-F | 10.00 |
| AUUQU-4-F | 6.00 |
| AUUQU-5-F | 9.00 |
| AUUQU-7-F | 6.00 |
| AUUQU-3-T | 8.00 |
| AUUQU-3-OT | 12.00 |
| PUZU-2-F | 6.00 |
| PUZU-3-F | 10.00 |
| PUZU-5-F | 9.00 |
| Σ | 100.00 |

TABLE-continued

Composition of the base mixture (host) H1 before addition of the polymerisation components:

| Properties | |
| --- | --- |
| T(N, I) | 66.6° C. |
| Δn (20° C., 589 nm) | 0.148 |

Description of the Polymerisation

Before the polymerisation of a sample, the phase properties of the medium are determined in a test cell with a thickness of about 10 microns and an area of 2×2.5 cm. The cell is filled by capillary action at a temperature of 75° C. The measurement is carried out under a polarising microscope with heating stage with a temperature programme of 1° C./min. The polymerisation of the media is carried out by irradiation with a UV lamp (Dr. Hönle, Bluepoint 2.1, 365 nm interference filter) having an effective power of about 1.5 mW/cm² for 180 seconds. The polymerisation is carried out directly in the electro-optical test cell. The polymerisation is carried out initially at a temperature at which the medium is in the blue phase I (BP-I). The polymerisation is carried out in a plurality of sub-steps, which gradually result in complete polymerisation. The temperature range of the blue phase generally changes during the polymerisation. Between each sub-step, the temperature is therefore modified so that the medium is still in the blue phase. In practice, this can be carried out by observing the sample under the polarising microscope after each irradiation operation of about 5 s or longer. If the sample becomes darker, this indicates a transition into the isotropic phase. The temperature for the next sub-step is reduced correspondingly. The entire irradiation time which results in maximum stabilisation is typically 180 s at the irradiation power indicated. Further polymerisations can be carried out in accordance with an optimised irradiation/temperature programme. Alternatively, the polymerisation can also be carried out in a single irradiation step, in particular if a broad blue phase is present even before the polymerisation.

Electro-Optical Characterisation

After the above-described polymerisation and stabilisation of the blue phase, the phase width of the blue phase is determined. The electro-optical characterisation is subsequently carried out at various temperatures within and if desired also outside this range.

The test cells used are fitted with interdigital electrodes on the cell surface on one side. The cell gap, the electrode separation and the electrode width are typically each 1 to 10 microns. This uniform dimension is referred to below as the gap width. The area covered by electrodes is about 0.4 cm². The test cells do not have an alignment layer. For the electro-optical characterisation, the cell is located between crossed polarising filters, with the longitudinal direction of the electrodes adopting an angle of 45° to the axes of the polarising filter. The measuring is carried out using a DMS301 (Autronic-Melchers) at right angles to the cell plane. In the voltage-free state, the arrangement described produces an essentially dark picture (definition 0% transmission).

Firstly, the characteristic operating voltages and then the response times are measured on the test cell. The operating voltage is applied to the cell electrodes in the form of a rectangular voltage with alternating sign (frequency 100 Hz) and variable amplitude, as described below.

The transmission in the voltage-free state is set as 0%. The transmission is measured while the operating voltage is increased. The achievement of the maximum value of about 100% intensity defines the characteristic quantity of the operating voltage $V_{100}$. Equally, the characteristic voltage $V_{10}$ is determined at 10% of the maximum transmission. These values are optionally measured at various temperatures in the range of the blue phase, in any case at room temperature (20° C.).

At the lower end of the temperature range of the blue phase, relatively high characteristic operating voltages $V_{100}$ are observed. At the upper end of the temperature range (close to the clearing point), the value of $V_{100}$ increases considerably. In the region of the minimum operating voltage, $V_{100}$ generally only increases slowly with temperature. This temperature range, delimited by $T_1$ and $T_2$, is referred to as the usable, flat temperature range (FR). The width of this "flat range" (FR) is $(T_2-T_1)$ and is referred to as the width of the flat range (WFR). The precise values of $T_1$ and $T_2$ are determined by the intersections of tangents at the flat curve section FR and the adjacent steep curve sections in the $V_{100}$/temperature diagram. In the second part of the measurement, the response times during switching on and off ($\tau_{on}$, $\tau_{off}$) are determined. The response time $\tau_{on}$ is defined by the time taken to achieve 90% intensity after application of a voltage at the level of $V_{100}$ at the selected temperature. The response time $\tau_{off}$ is defined by the time taken to decrease by 90% starting from the maximum intensity at $V_{100}$ after the voltage has been reduced to 0 V. The response time is also determined at various temperatures in the range of the blue phase. As further characterisation, the transmission for a continuously varied operating voltage between 0 V and $V_{100}$ can be measured at a temperature within FR. Comparison of the curves for increasing and decreasing operating voltage can give rise to a hysteresis. The difference between the transmissions at $0.5 \cdot V_{100}$ and the difference between the voltages at 50% transmission are, for example, characteristic hysteresis values and are referred to as $\Delta T_{50}$ and $\Delta V_{50}$ respectively.

As a further parameter, the ratio of the transmission in the voltage-free state before and after passing through a switching cycle can be measured. This transmission ratio is known as the "memory effect". The value of the memory effect in the ideal state is 1.0. Values above 1 mean that a certain memory effect is present in the form of excessively high residual transmission after the cell has been switched on and off. This value is also determined in the working range of the blue phase (FB).

The measurement values, unless indicated otherwise, are determined at 20° C.

Use Examples M1 and M2 and Comparative Examples C1 and C2

The following polymerisable media are assembled and measured:

| Component | M1 | M2 | C1 | C2 |
|---|---|---|---|---|
| | Proportion [% by weight] | | | |
| H1 | 86.3 | 86.3 | 86.3 | 86.3 |
| DP-1 | 2.5 | 2.5 | 2.5 | 2.5 |
| IN-1 | 0.2 | 0.2 | 0.2 | 0.2 |
| RM-1a | 6 | | | |
| RM-1b | | 6 | | |
| RM-257 | | | 6 | 6 |
| RM-2 | 5 | 5 | 5 | |
| RM-3 | | | | 5 |
| Measurement values (polymerised) | | | | |
| Blue phase at 20° C. | yes | yes | yes | yes |
| $V_{100}$ [V] | 52 | 46 | 46 | 59 |
| Memory effect | 1.4 | 1.3 | 7.8 | 1.0 |
| Gap width | 10 μm | 10 μm | 10 μm | 10 μm |

M1 and M2 comprise compounds RM-1a/b according to the invention.

The media are characterised as described before the polymerisation. The RM components are then polymerised in the blue phase by irradiation once (180 s), and the media obtained are re-characterised.

The polymer-stabilised liquid-crystalline media exhibit blue phases over a broad temperature range. Compared with Comparative Example C2, lower values are observed for the operating voltage $V_{100}$ for M1 and M2 with a comparable memory effect.

Compared with Comparative Example C1, comparable values are achieved for the operating voltage $V_{100}$ with an advantageously lower memory effect.

Further combinations of the embodiments and variants of the invention arise from the following claims.

The invention claimed is:
1. A compound of formula I

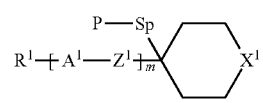

in which
$X^1$ denotes

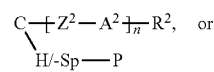

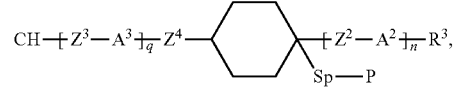

$R^1$ denotes a group -Sp-P,
$R^2$ denotes a radical -Sp-P, a halogenated or unsubstituted alkyl radical having 1 to 15 C atoms, in which one or more $CH_2$ groups are each optionally replaced, independently of one another, by —C≡C—, —CH═CH—, —(CO)O—, —O(CO)—, —(CO)— or —O— in such a way that 0 atoms are not linked directly to one another, F, Cl, Br, CN, SCN, NCS or $SF_5$,
where if m=0, $X^1$ does not contain a group -Sp-P,
$R^3$ independently is defined like $R^2$ or denotes H, $A^1$, $A^2$ and $A^3$ each, independently of one another, denote:
a) trans-1,4-cyclohexylene or cyclohexenylene, in which one or more non-adjacent $CH_2$ groups are optionally replaced by —O— and/or —S— and in which H is optionally replaced by F,
b) 1,4-phenylene, in which one or two CH groups are optionally replaced by N and in which one or more H atoms are optionally replaced by Br, Cl, F, CN, methyl, methoxy or a mono- or polyfluorinated methyl or methoxy group, or
c) bicyclo[1.1.1]pentane-1,3-diyl, bicyclo[2.2.2]octane-1,4-diyl, spiro[3.3]heptane-2,6-diyl, tetrahydropyran-2,5-diyl, 1,3-dioxane-2,5-diyl, tetrahydrofuran-2,5-diyl, cyclobut-1,3-diyl, piperidine-1,4-diyl, thiophene-2,5-diyl, selenophene-2,5-diyl,

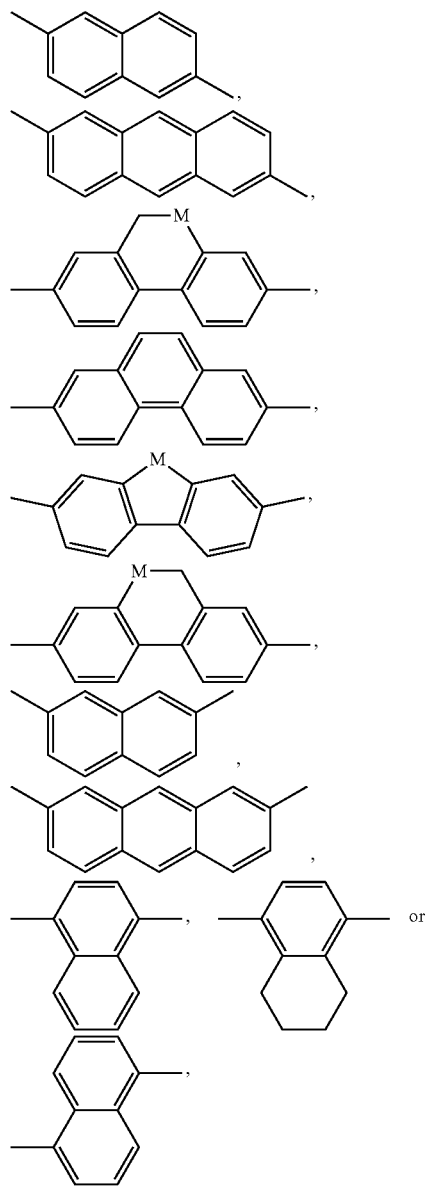

in which one or more hydrogen atoms are optionally substituted by F, CN, SCN, NCS, $SF_5$, $CH_2F$, $CHF_2$, $CF_3$, $OCH_2F$, $OCHF_2$ or $OCF_3$, one or more double bonds are optionally replaced by single bonds, one or more CH groups are optionally replaced by N, M denotes —O—, —S—, —$CH_2$—, —CHY— or —$CYY^1$—,
Y and $Y^1$ denote Cl, F, CN, $OCF_3$ or $CF_3$,
$Z^1$, $Z^2$, $Z^3$ and $Z^4$ each, independently of one another, denote a single bond, —O—, —$CH_2$—, —$O(CO)CH_2$—, —$CH_2O$—, —$CH_2OCH_2$—, —(CO)O—, —$CF_2O$—, —CH2CH2CF2O—, —$CF_2CF_2$—, —CH2CF2-, —CH2CH2-, —$(CH_2)_4$—, —CH=CH—, —CH=CF—, —CF=CF— or —C≡C—, where asymmetrical groups may be oriented in either direction,
m denotes 0, 1, 2 or 3,
n denotes 0, 1, 2 or 3,
q denotes 0, 1, 2 or 3,
P denotes $CH_2$=$CW^1$—COO—, $CH_2$=$CW^1$—CO—,

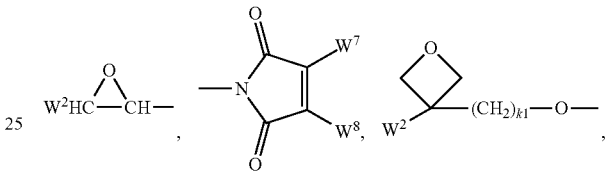

$CH_2$=$CW^2$—$(O)_{k3}$—, $CH_2$=$CW^1$—CO—NH—, $CH_3$—CH=CH—O—, $(CH_2=CH)_2CH$—OCO—, $(CH_2=CH$—$CH_2)_2CH$—OCO—, $(CH_2=CH)_2CH$—O—, $(CH_2=CH$—$CH_2)_2N$—, $(CH_2=CH$—$CH_2)_2N$—CO—, HS—$CW^2W^3$—, HO—$CW^2W^3$—NH—, $CH_2$=CH—$(COO)_{k1}$-Phe-$(O)_{k2}$—, $CH_2$=CH—$(CO)_{k1}$-Phe-$(O)_{k2}$—, Phe-CH=CH—, OCN— or $W^4W^5W^6Si$—, $W^1$ denotes H, F, Cl, CN, $CF_3$, phenyl or alkyl having 1 to 5 C atoms,
$W^2$ and $W^3$ each, independently of one another, denote H or alkyl having 1 to 5 C atoms, $W^4$, $W^5$ and $W^6$ each, independently of one another, denote Cl, oxaalkyl or oxacarbonylalkyl having 1 to 5 C atoms,
$W^7$ and $W^8$ each, independently of one another, denote H, Cl or alkyl having 1 to 5 C atoms,
Phe denotes 1,4-phenylene, which is optionally substituted by one or more radicals L,
L denotes F, Cl, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$ or phenyl,
$k_1$ and $k_2$ each, independently of one another, denote 0 or 1,
$k_3$ denotes 1,
Sp denotes Sp'-X,
Sp' denotes alkylene having 1 to 24 C atoms, which is optionally mono- or poly-substituted by F, Cl, Br, I or CN and in which one or more non-adjacent $CH_2$ groups are each optionally replaced, independently of one another, by —O—, —S—, —NH—, —$NR^0$—, —$SiR^{00}R^{000}$—, —CO—, —(CO)O—, —O(CO)—, —O(CO)O—, —S(CO)—, —(CO)S—, —$NR^{00}$—CO—O—, —O—CO—$NR^{00}$—, —$NR^{00}$—CO—$NR^{00}$—, —CH=CH— or —C≡C— in such a way that O and/or S atoms are not linked directly to one another,
X denotes —O—, —S—, —CO—, —(CO)O—, —O(CO)—, —O(CO)O—, —CO—$NR^{00}$—, —$NR^{00}$—CO—, —$NR^{00}$—CO—$NR^{00}$—, —$OCH_2$—, —$CH_2O$—, —$(CH_2)_2$—O—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=CR⁰—, —CY²=CY³—, —C≡C—, —CH=CH—(CO)O—, —O(CO)—CH=CH— or a single bond, R⁰, R⁰⁰ and R⁰⁰⁰ each, independently of one another, denote H or alkyl having 1 to 12 C atoms, and Y² and Y³ each, independently of one another, denote H, F, Cl or CN.

2. A compound according to claim 1, wherein
P denotes a radical of the formula $CH_2=CW^1-COO-$, in which $W^1$ is H, F, Cl, CN, $CF_3$, phenyl or alkyl having 1 to 5 C atoms.

3. A compound according to claim 1, wherein m=0.

4. A compound according to claim 1, wherein $X^1$ denotes

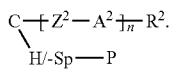

5. A compound according to claim 1, in which
Sp' denotes alkylene having 1 to 12 C atoms, which is optionally mono- or polysubstituted by F, Cl, Br, I or CN and in which one or more non-adjacent $CH_2$ groups are each optionally replaced, independently of one another, by —O—, —S—, —NH—, —NR⁰—, —SiR⁰⁰R⁰⁰—, —CO—, —(CO)O—, —O(CO)—, —O(CO)O—, —S(CO)—, —(CO)S—, —NR⁰⁰—CO—O—, —O—CO—NR⁰⁰—, —NR⁰⁰—CO—NR⁰⁰—, CH=CH— or —C≡C— in such a way that O and/or S atoms are not linked directly to one another, and X denotes a single bond, —O—, —O(CO)—, —(CH₂)₂—O—, —CH₂(CO)O— or —OCH₂—.

6. A compound according to claim 1, wherein the number of P groups is 2, 3 or 4.

7. A process for preparing a compound of formula I according to claim 2, comprising linking the group -Sp-P, —P or parts thereof to a precursor alcohol or a polyol compound.

8. A liquid-crystalline medium, comprising one or more compounds of formula I of claim 1 or a polymerisation product thereof.

9. A process for preparing an electro-optical device comprising a liquid-crystalline, polymer-stabilised medium, comprising polymerizing a liquid-crystalline medium comprising one or more compounds of formula I according to claim 1.

10. A liquid-crystalline medium or a polymer in a liquid-crystalline medium, comprising one or more compounds of the formula I according to claim 1 or a polymerisation product thereof.

11. A method for the stabilisation of the liquid-crystalline phase in a liquid-crystalline medium or for the stabilisation of the alignment of a liquid-crystalline medium, comprising adding to said medium one or more compounds of the formula I according to claim 1.

12. A liquid-crystalline medium according to claim 8, which, after stabilisation of the blue phase by polymerisation, has a blue phase at least in the range from 20 to 25° C.

13. A method for achieving an electro-optical effect, comprising producing said effect by a liquid-crystalline medium according to claim 8.

14. An electro-optical liquid-crystal display containing a liquid-crystalline medium according to claim 8.

15. A compound according to claim 1, wherein Phe denotes 1,4-phenylene, which is not substituted.

16. A liquid-crystalline medium, comprising one or more compounds of formula I or a polymerisation product thereof

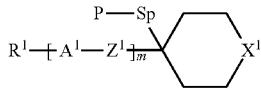

in which
$X^1$ denotes

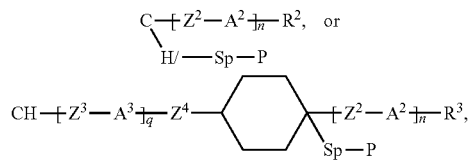

$R^1$ and $R^2$ each, independently of one another, denote a radical -Sp-P, a halogenated or unsubstituted alkyl radical having 1 to 15 C atoms, in which one or more $CH_2$ groups are each optionally replaced, independently of one another, by —C≡C—, —CH=CH—, —(CO)O—, —O(CO)—, —(CO)— or —O— in such a way that O atoms are not linked directly to one another, F, Cl, Br, CN, SCN, NCS or $SF_5$, where $R^1$ denotes a group -Sp-P if m=0 and $X^1$ does not contain a group -Sp-P, $R^3$ independently is defined like $R^2$ or denotes H, $A^1$, $A^2$ and $A^3$ each, independently of one another, denote:

a) trans-1,4-cyclohexylene or cyclohexenylene, in which one or more non-adjacent $CH_2$ groups are optionally replaced by —O— and/or —S— and in which H is optionally replaced by F, b) 1,4-phenylene, in which one or two CH groups are optionally replaced by N and in which one or more H atoms are optionally replaced by Br, Cl, F, CN, methyl, methoxy or a mono- or polyfluorinated methyl or methoxy group, or c) bicyclo[1.1.1]pentane-1,3-diyl, bicyclo[2.2.2]octane-1,4-diyl, spiro[3.3]heptane-2,6-diyl, tetrahydropyran-2,5-diyl, 1,3-dioxane-2,5-diyl, tetrahydrofuran-2,5-diyl, cyclobut-1,3-diyl, piperidine-1,4-diyl, thiophene-2,5-diyl, selenophene-2,5-diyl,

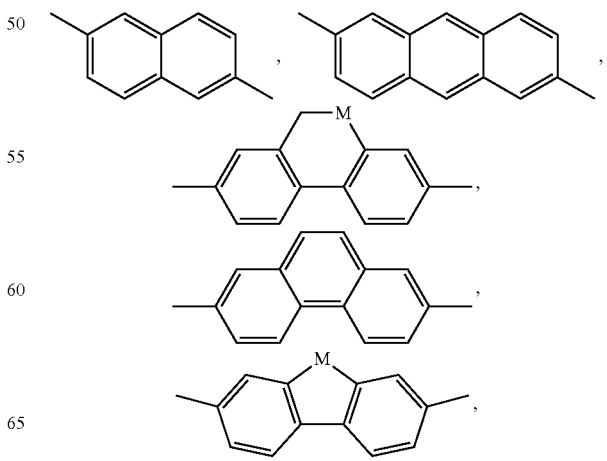

-continued

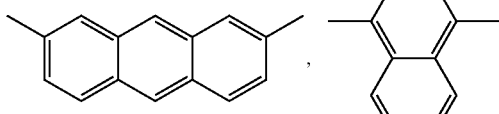
,
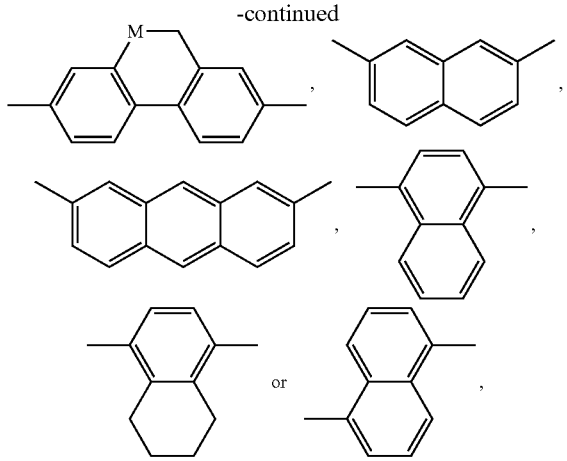

in which one or more hydrogen atoms are optionally substituted by F, CN, SCN, NCS, SF$_5$, CH$_2$F, CHF$_2$, CF$_3$, OCH$_2$F, OCHF$_2$ or OCF$_3$,
one or more double bonds are optionally replaced by single bonds,
one or more CH groups are optionally replaced by N,
M denotes —O—, —S—, —CH$_2$—, —CHY— or —CYY$^1$—,
Y and Y$^1$ denote Cl, F, CN, OCF$_3$ or CF$_3$,
Z$^1$, Z$^2$, Z$^3$ and Z$^4$ each, independently of one another, denote
  a single bond, —O—, —CH$_2$—, —O(CO)CH$_2$—, —CH$_2$O—, —CH$_2$OCH$_2$—, —(CO)O—, —CF$_2$O—, —CH2CH2CF$_2$O—, —CF$_2$CF$_2$—, —CH2CF2-, —CH2CH2-, —(CH$_2$)$_4$—, —CH=CH—, —CH=CF—, —CF=CF— or —C≡C—, where asymmetrical groups may be oriented in either direction,
m denotes 0, 1, 2 or 3,
n denotes 0, 1, 2 or 3,
q denotes 0, 1, 2 or 3,
P denotes a polymerisable group, and
Sp denotes a spacer group or a single bond.

17. A liquid-crystalline medium according to claim 16, which, after stabilisation of the blue phase by polymerisation, has a blue phase at least in the range from 20 to 25° C.

18. An electro-optical liquid-crystal display containing a liquid-crystalline medium according to claim 16.

19. A process for preparing an electro-optical device comprising a liquid-crystalline, polymer-stabilised medium, comprising polymerizing a liquid-crystalline medium comprising one or more compounds of formula I

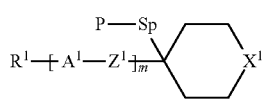
                                                              I in which
X$^1$ denotes

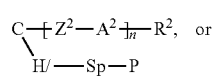
, or

-continued

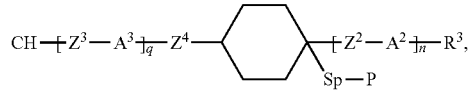

R$^1$ and R$^2$ each, independently of one another, denote a radical -Sp-P, a halogenated or unsubstituted alkyl radical having 1 to 15 C atoms, in which one or more CH$_2$ groups are each optionally replaced, independently of one another, by —C≡C—, —CH=CH—, —(CO)O—, —O(CO)—, —(CO)— or —O— in such a way that O atoms are not linked directly to one another,
F, Cl, Br, CN, SCN, NCS or SF$_5$,
where R$^1$ denotes a group -Sp-P if m=0 and X$^1$ does not contain a group -Sp-P,
R$^3$ independently is defined like R$^2$ or denotes H,
A$^1$, A$^2$ and A$^3$ each, independently of one another, denote:
a) trans-1,4-cyclohexylene or cyclohexenylene, in which one or more non-adjacent CH$_2$ groups are optionally replaced by —O— and/or —S— and in which H is optionally replaced by F,
b) 1,4-phenylene, in which one or two CH groups are optionally replaced by N and in which one or more H atoms are optionally replaced by Br, Cl, F, CN, methyl, methoxy or a mono- or polyfluorinated methyl or methoxy group, or
c) bicyclo[1.1.1]pentane-1,3-diyl, bicyclo[2.2.2]octane-1,4-diyl, spiro[3.3]heptane-2,6-diyl, tetrahydropyran-2,5-diyl, 1,3-dioxane-2,5-diyl, tetrahydrofuran-2,5-diyl, cyclobut-1,3-diyl, piperidine-1,4-diyl, thiophene-2,5-diyl, selenophene-2,5-diyl,

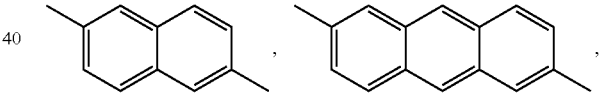

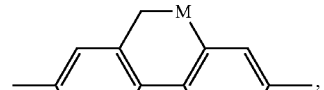

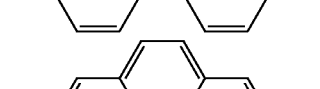

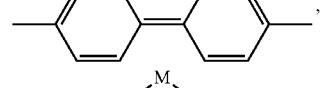

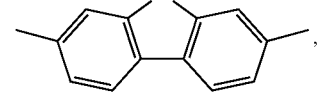

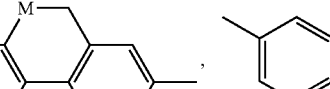

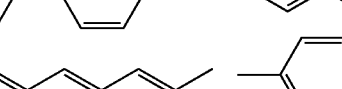

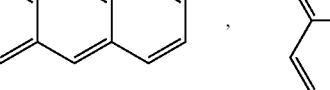

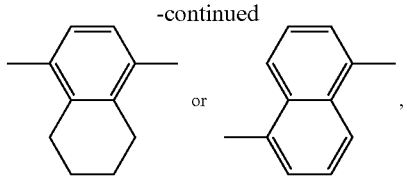

in which one or more hydrogen atoms are optionally substituted by F, CN, SCN, NCS, $SF_5$, $CH_2F$, $CHF_2$, $CF_3$, $OCH_2F$, $OCHF_2$ or $OCF_3$, one or more double bonds are optionally replaced by single bonds, one or more CH groups are optionally replaced by N, M denotes —O—, —S—, —$CH_2$—, —CHY— or —$CYY^1$—, Y and $Y^1$ denote Cl, F, CN, $OCF_3$ or $CF_3$, $Z^1$, $Z^2$, $Z^3$ and $Z^4$ each, independently of one another, denote a single bond, —O—, —$CH_2$—, —O(CO)$CH_2$, —$CH_2O$—, —$CH_2OCH_2$—, —(CO)O—, —$CF_2O$—, —$CH2CH2CF_2O$—, —$CF_2CF_2$—, —CH2CF2-, —CH2CH2-, —$(CH_2)_4$—, —CH=CH—, —CH=CF—, —CF=CF— or —C≡C—, where asymmetrical groups may be oriented in either direction, m denotes 0, 1, 2 or 3,
n denotes 0, 1, 2 or 3,
q denotes 0, 1, 2 or 3,
P denotes a polymerisable group, and
Sp denotes a spacer group or a single bond.

20. A liquid-crystalline medium according to claim 16, wherein

P denotes $CH_2$=$CW^1$—COO—, $CH_2$=$CW^1$—CO—,

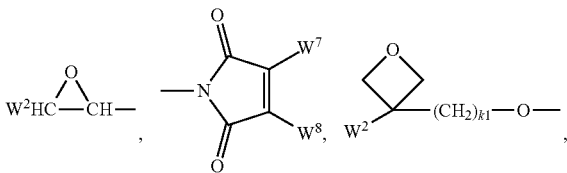

$CH_2$=$CW^2$—(O)$_{k3}$—, $CH_2$=$CW^1$—CO—NH—, $CH_3$—CH=CH—O—, ($CH_2$=CH)$_2$CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, HS—$CW^2W^3$—, HO—$CW^2W^3$—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH—, OCN— or $W^4W^5W^6Si$—.

* * * * *